(12) United States Patent
Chen et al.

(10) Patent No.: US 8,467,874 B2
(45) Date of Patent: Jun. 18, 2013

(54) GASTROINTESTINAL ELECTRICAL STIMULATION

(75) Inventors: Jiande Chen, Houston, TX (US); Pankaj Jay Pasricha, Cupertino, CA (US)

(73) Assignee: The Board of Regents of the University of Texas System, Austin, TX (US)

( * ) Notice: Subject to any disclaimer, the term of this patent is extended or adjusted under 35 U.S.C. 154(b) by 267 days.

(21) Appl. No.: 12/839,117

(22) Filed: Jul. 19, 2010

(65) Prior Publication Data

US 2011/0034967 A1 Feb. 10, 2011

Related U.S. Application Data

(60) Continuation-in-part of application No. 10/922,133, filed on Aug. 19, 2004, which is a division of application No. 09/913,556, filed as application No. PCT/US00/28128 on Oct. 11, 2000, now Pat. No. 6,826,428.

(60) Provisional application No. 60/195,977, filed on Apr. 11, 2000.

(51) Int. Cl.
*A61N 1/36* (2006.01)

(52) U.S. Cl.
USPC .............................................. 607/40; 607/133

(58) Field of Classification Search
USPC ...................................................... 607/40, 133
See application file for complete search history.

(56) References Cited

U.S. PATENT DOCUMENTS

| | | |
|---|---|---|
| 3,909,883 A | 10/1975 | Fagen |
| 4,414,986 A | 11/1983 | Dickhudt |
| 5,188,104 A * | 2/1993 | Wernicke et al. ............... 607/40 |
| 5,193,539 A | 3/1993 | Schulman |
| 5,197,491 A | 3/1993 | Anderson |
| 5,263,480 A | 11/1993 | Wernicke |
| 5,292,344 A | 3/1994 | Douglas |

(Continued)

FOREIGN PATENT DOCUMENTS

| | | |
|---|---|---|
| WO | 99/03532 A2 | 1/1999 |
| WO | 99/30776 A1 | 6/1999 |
| WO | 02/089655 A1 | 11/2002 |
| WO | 2009/009276 A2 | 1/2009 |

OTHER PUBLICATIONS

Bellahsene et al., IEEE/Ninth Annual Conf. of Eng. in Med. and Biol. Soc. (1987).
Bellahsene et al., American Physiology Society, (1992).

(Continued)

*Primary Examiner* — Joseph Stoklosa

(57) ABSTRACT

The disclosure provides a method of treatment for obesity, in an individual in need thereof, by administering electrical stimulation at dual sites in the gastrointestinal tract. The electrical stimulations are administered by positioning bipolar stimulatory electrodes in contact with the gastric and dudenol cavities, along afferent vagal neural pathways, in the gastrointestinal tract. The electrical stimulations thus administered, activate the vagal afferents associated with the gastric and dudenol sites in the gastrointestinal tract. The activation of vagal afferents modulates the gastrointestinal peptide satiety hormones. Further, the disclosure provides a method of treatment for eating disorders, in an individual in need thereof, by administering electrical stimulation at dual sites, along afferent vagal neural pathways, in the gastrointestinal tract. Also, provided is a method of regulating the appetite of an individual in need thereof, by administering electrical stimulation at dual sites in the gastrointestinal tract.

9 Claims, 21 Drawing Sheets

U.S. PATENT DOCUMENTS

| | | | |
|---|---|---|---|
| 5,423,872 A | 6/1995 | Cigaina | |
| 5,540,730 A | 7/1996 | Terry, Jr. | |
| 5,556,425 A | 9/1996 | Hewson | |
| 5,649,902 A | 7/1997 | Yoon | |
| 5,690,691 A * | 11/1997 | Chen et al. | 607/40 |
| 5,716,392 A | 2/1998 | Bourgeois | |
| 5,836,994 A | 11/1998 | Bourgeois | |
| 5,861,014 A | 1/1999 | Familoni | |
| 5,882,340 A | 3/1999 | Yoon | |
| 5,935,126 A | 8/1999 | Riza | |
| 5,995,872 A | 11/1999 | Bourgeois | |
| 6,006,755 A | 12/1999 | Edwards | |
| 6,026,326 A | 2/2000 | Bardy | |
| 6,051,017 A | 4/2000 | Loeb | |
| 6,091,992 A | 7/2000 | Bourgeois | |
| 6,243,607 B1 | 6/2001 | Mintchev | |
| 6,542,776 B1 | 4/2003 | Gordon | |
| 6,571,127 B1 | 5/2003 | Ben-Haim | |
| 6,684,104 B2 | 1/2004 | Gordon | |
| 6,826,428 B1 | 11/2004 | Chen | |
| 6,853,862 B1 | 2/2005 | Marchal | |
| 7,016,735 B2 | 3/2006 | Imran et al. | |
| 7,076,306 B2 | 7/2006 | Marchal | |
| 7,177,693 B2 | 2/2007 | Starkebaum | |
| 7,203,551 B2 | 4/2007 | Houben et al. | |
| 7,310,557 B2 | 12/2007 | Maschino et al. | |
| 7,363,084 B2 | 4/2008 | Kurokawa et al. | |
| 7,477,994 B2 | 1/2009 | Sunshine et al. | |
| 7,519,431 B2 | 4/2009 | Goetz | |
| 7,599,736 B2 | 10/2009 | DiLorenzo | |
| 7,676,270 B2 | 3/2010 | Imran | |
| 7,711,437 B1 | 5/2010 | Bornzin | |
| 7,720,539 B2 | 5/2010 | Mintchev | |
| 2003/0055463 A1 | 3/2003 | Gordon | |
| 2005/0222638 A1 | 10/2005 | Foley | |
| 2005/0251219 A1 | 11/2005 | Evans | |
| 2006/0074456 A1 | 4/2006 | Pyles | |
| 2007/0049793 A1 | 3/2007 | Ignagni et al. | |
| 2008/0183238 A1 | 7/2008 | Chen | |
| 2010/0228313 A1 | 9/2010 | Starkebaum | |

OTHER PUBLICATIONS

Jiande Chen, Identifying No. 1R43DK55437-01 (1999).
Jiande Chen, Identifying No. 121442 (1998).
Chen et al., Gastroenterology & Hepatology, 13:S232-236 (Suppl) (1998).
Chen et al., IEEE-EMBC & CMBEC :1691-1692 (1995).
Kuwahara, Jap. J. Phys., 33:29-40 (1983).
Lin et al., AJP-Gastroenterology & Liver Physiology, 274(1):G186 (1998).
Lin et al., Am. J. Gastroenterology, 92(9):1527-1530 (1997).
McCallum et al., Gastroenterology, 114:456-461 (1998).
Mintchev et al., Gastroenterology, 118:258-263 (2000).
Mintchev et al., Annuls of biomedical Engineering, 25:726-730 (1997).
Mintchev et al., Gut, 43:607-611 (1998).
Mintchev et al., J. Med. Eng. (1999).
Office Action dated Jun. 24, 2010; U.S. Appl. No. 11/681,237.
Borovikova et al., 2000, Autonomic Neuroscience: Basic and Clinical 85:141-7.
Mintchev et al., 2000, Gastroenterology 118:258-263.
Schwartz, 2006, Cell Metabolism 4(2):103-105.

* cited by examiner

GASTROINTESTINAL ELECTRICAL STIMULATION

RELATED APPLICATIONS

This application claims priority of U.S. Provisional Patent Application No. 60/195,977, filed Apr. 11, 2000. This application is a continuation in part of U.S. patent application Ser. No. 10/922,133 filed on Aug. 19, 2004, which is a division of U.S. patent application Ser. No. 09/913,556 filed on Mar. 27, 2002, now U.S. Pat. No. 6,826,428 filed as a national stage of PCT/US00/28128 which was filed on Oct. 11, 2000.

FIELD

The present disclosure relates generally to gastrointestinal electrical stimulation, and more particularly to methods for regulating gastrointestinal action, reducing weight, providing electrical field stimulation to a gastrointestinal organ, providing electrical potential gradient in a gastrointestinal organ, stimulating the vagus nerve, and placing a device in the gastrointestinal tract or wall.

BACKGROUND

Obesity is a complex, multifactorial and chronic condition characterized by excess body fat. Obesity results from an imbalance between energy expenditure and caloric intake. Although the causes of this imbalance are not completely understood, genetic and/or acquired physiologic events and environmental factors are important. Recent studies have shown that approximately a third of the variance in adult body weights results from genetic influences (Stunkard 1996). In this regard, much attention has been paid to leptin, an adipocyte- and placenta-derived circulating protein that communicates the magnitude of fat stores to the brain. A deficiency of leptin (ob/ob) or a defective leptin receptor (db/db) seems responsible for obesity in ob/ob and ob/db mice and obese Zucker rats (Frederich et al., 1995).

Various gastrointestinal peptides, such as cholecystokinin, enterostatin and glucagon and neurotransmitters (serotonin) that provide communication between the brain, gastrointestinal tract and adipose tissue also may have an etiologic role in obesity (Bandini et al., 1990). Gastrointestinal (GI) peptide hormones are integral contributors to the numerous peripheral signals that regulate food intake and energy balance. GI peptide hormones such as ghrelin, obstatin, cholecystokinin-8 (CCK-8) and peptide YY (PYY), that are synthesized and released from the GI tract have multi-potential capabilities through a complex interplay from mechanoreceptor and chemoreceptor, signaling events, to regulate satiety and appetite. They can interact locally with specific receptors on vagal afferent axons passing to the brain. These gut peptides can also be released directly into the blood stream allowing their delivery to distant sites of action to relay information regarding nutritional status. These GI peptide hormones that control appetite and satiety have enormous potential as novel therapeutic targets in the treatment of human obesity and its long-term management.

Possible environmental mechanisms for obesity involve pharmacologic agents (such as antipsychotic drugs and certain antidepressants), cultural and ethnic factors (Morley 1987), hyperphagia and high fat intake (Sobal and Stunkard 1989), inactivity, and psychological factors, such as overeating resulting from emotional distress, including poor mood or depression and low self-esteem (Namnoum 1993).

Obesity is one of the most prevalent public health problems in the United States. In a National Health and Nutrition Examination Survey for 1999-2002 conducted by the Center for Disease Control and Prevention, it is estimated that approximately 30 percent of U.S. adults, or about 60 million people, ages 20 or higher, are obese, i.e., having a body mass index of 30 or higher. "Overweight" typically means a body mass index or BMI=25.0-29.9 kg/m². Even a decade ago, "Morbid obesity" or clinically severe obesity, which is defined as having a BMI≧40 or >100 lbs over normal weight, affected more than 15 million Americans (Kuczmarski et al., 1994; Troiano et al., 1995; Flegal et al., 1998; Kuczmarski et al., 1997). Obesity is associated with an increased prevalence of socioeconomic hardship due to a higher rate of disability, early retirement, and widespread discrimination (Enzi 1994; Gortmaker et al., 1993).

Obesity is a major risk factor for many chronic diseases, including diabetes mellitus type II, cardiovascular diseases, reproductive disorders, certain cancers, gallbladder disease, respiratory disease and other comorbidities, such as osteoarthritis, edema, gastroesophageal reflux, urinary stress incontinence, idiopathic intracranial hypertension, or venous stasis disease of the lower extremities (AACE/ACE Position 1998). Although patients with type II diabetes are not necessarily obese, weight gain before the development of type II diabetes is common (Despres 1993). Obesity is the most powerful environmental risk factor for diabetes mellitus type II (Kissebah et al., 1989) and the prevalence of diabetes is 2.9 times higher in overweight (BMI≧27.8 in men and ≧27.3 in women) than in non-overweight subjects 20 to 75 years of age (NIH 1985). When this age range is narrowed to between 20 and 45 years, this risk is 3.8 times higher (Van Itallie 1985). Mortality due to cardiovascular disease is almost 50% higher in obese patients than in those of average weight and is 90% higher in those with severe obesity (Namnoum 1993). Sixty percent of obese patients have hypertension (Alpert and Hashimi 1993). Fatty infiltration of the myocardium, right hypertrophy, excess epicardial fat, abnormalities of ventricular function, and increased left ventricular filling pressure all seem closely related to the duration of obesity (Nakajima et al., 1985). Obesity has a detrimental effect on female reproductive function (Thompson 1997). In comparison with normal-weight women, obese female patients have a higher mortality rate from cancer of the gallbladder, biliary passages, breast, uterus and ovaries (NIH 1985). Obese men have a higher rate of mortality from rectal and prostate cancer than non-obese men (NIH 1985). Both obese men and women have an increased risk of colon cancer. Obesity is a common cause of sleep apnea and about 50% to 70% of patients diagnosed with sleep apnea are obese (Douglas 1995). Sleep apnea is associated with an increased risk of vehicular accidents and cardiovascular and cerebrovascular incidents (Douglas 1995).

In the past, the success of treatment modalities for obesity was measured by the rate and amount of weight loss. More recently, success is being measured by the ability to achieve and maintain a clinically helpful and significant weight loss and by the salutary effects of weight loss on comorbidities of obesity. The treatment of obesity can be classified into three categories: general measures, pharmacotherapy and surgical treatment.

Typically, an obese patient is first counseled about adopting some general measures such as caloric restriction, behavior therapy and physical activity. The goal of this program is to integrate positive eating and physical activity behaviors into the patient's life. Although an acceptable weight loss may be achieved with such measures, maintaining weight loss seems to be more difficult, particularly for patients who were treated with caloric restriction. About 50% of patients regain weight within one year after the treatment and almost all patients regain weight within 5 years (AACE/ACE Position 1998).

One common treatment for obesity is pharmacotherapy. Amphetamine derivatives such as fenfluramine and dexfenfluramine were commonly used until their withdrawal from the market due to the-long-term risk of cardiovascular effects (Bray and Greenway 1999). A number of other FDA-approved drugs are currently available for the medical treatment of obesity. These include sibutramine, diethylpropion, mazindol, phentermine, phenylpropanolamine, orlistat etc. (Bray and Greenway 1999; Hvizdos et al., 1999).

Sibutramine, a centrally acting antiobesity agent, was approved by the FDA for use up to 1 year. Its clinical efficacy has been evaluated in about 4,600 patients worldwide (Smith 1997). Its adverse events include dry mouth, anorexia and constipation. However, it may have several drug interactions and may be problematic in patients with poorly controlled or uncontrolled hypertension, severe renal impairment, severe hepatic dysfunction, congestive heart failure, coronary artery disease, and etc.

Diethylpropion, an anorexic agent, is typically approved for only short term use. A clinical trial indicated a weigh loss ranging from 6.6 kg to 11.3 kg but 82% of the 200 patients did not complete the trial (Le Riche and Csima 1967).

Mazindol, which is structurally related to the tricyclic antidepressant agents, may act by blocking norepinephrine reuptake and synaptically release dopamine. It is effective as an appetite suppressant. Loss of weight of 12 to 14 kg was reported in a one-year study. However, the placebo group also showed a weight loss of 10 kg (Enzi et al., 1976).

Phenylpropanolamine acts on the $\alpha_1$-receptor and is used systemically as an appetite suppressant. In a comprehensive obesity-management program, it was shown an increased weight loss by 0.25 to 0.5 pound weekly in comparison with placebo. However, its effect diminishes after 4 weeks (Lasagna 1988; Greenway 1992).

Another commonly known treatment of obesity is gastric bypass surgery. The surgery divides the stomach into smaller portions and one section, known as the gastric pouch, is then connected to the small intestines. Due to the size of the pouch, food intake is limited, resulting in a reduction in calorie intake and weight loss. Typically gastric bypass surgery is reserved for patients with morbid obesity (BMI>40) (Consensus Development 1991). Two options are generally available. The first is a restrictive operation designed to make the stomach smaller, such as vertical banded gastroplasty (also called gastric stapling) which can be done laparoscopically (Doldi et al., 2000; Balsiger et al., 2000). Vertical banded gastroplasty results in a weight loss for at least 2 years (Sagar 1995) but some of the weight lost may be regained within 5 years (Nightengale et al., 1991). Longer follow-up studies are not available (Sagar 1995). The second kind of surgery is a gastric bypass operation that promotes mal-digestion of ingested nutrients. This includes procedures such as Roux-en-Y gastric bypass or extensive gastric bypass (biliopancreatic diversion) (Institute of Medicine 1995; Benotti and Forse 1995; Fried and Peskova 1997; Scorpinaro et al., 1996; Scopinaro et al., 1981). Roux-en-Y gastric bypass produces more substantial weight loss than vertical banded gastroplasty (Brolin et al., 1992; Sugerman et al., 1992). This procedure is a more complicated gastric bypass that successfully promotes weight loss. Other surgical approaches include intestinal bypass (effective but associated with major complications), jaw wiring (effective while used), and liposuction (cosmetic procedure).

The risks involved with surgical treatment of morbid obesity are substantial. While the immediate operative mortality rate for both vertical banded gastroplasty and Roux-en-Y gastric bypass has been relative low, morbidity in the early postoperative period (wound infections, dehiscence, leaks from staple-line breakdown, stomal stenosis, marginal ulcers, various pulmonary problems and deep thrombophlebitis in the aggregate) may be as high as 10% or more. In the later postoperative period, other problems may arise and may require reoperative surgery. Such problems include pouch and distal esophageal dilation, persistent vomiting (with or without stomal obstruction), cholecystitis or failure to lose weight. Moreover, mortality and mobidity associated with reoperative surgery are higher than those associated with primary operations. In the long term, micronutrient deficiencies, particularly of vitamin $B_{12}$, folate and iron, are common after gastric bypass and must be sought and treated. Another potential result of this operation is the so-called "dumping syndrome" which is characterized by gastrointestinal distress and other symptoms.

Another possibility associated with reduction in obesity is gastrointestinal electrical stimulation for the treatment of gastrointestinal motility disorders. Electrical stimulation of the gastrointestinal (GI) tract is analogous to pacing of the human heart. Organs of the GI tract have their own natural pacemakers, and the electrical signals they generate can be altered by externally delivering certain types of electric currents via intraluminal or serosal electrodes to certain areas of the GI tract. Abnormalities in gastric slow waves lead to gastric motor disorders and have been frequently observed in patients with functional disorders of the gut, such as gastroparesis, functional dyspepsia, anorexia and etc. Therefore, electrical stimulation of GI organs is a valuable alternative to medication and surgical approaches in the treatment of GI dysfunctions.

The success of this technique has been reported in both dogs and humans (U.S. Pat. Nos. 5,423,872, 5,690,691, and 5,836,994; PCT No. PCT/US1998/026506; Bellahsene et al., 1992; Mintchev et al., 1998; Mintchev et al., 1999; Mintchev et al., 2000; Chen et al. 1998; Chen et al. 1995c). These disorders are characterized by poor contractility and delayed emptying (by contrast with obesity) and the aim of electrical stimulation in this setting is to normalize the underlying electrical rhythm and improve these parameters. In general, this is done by antegrade or forward gastric (or intestinal) stimulation.

Motility is one of the most critical physiological functions of the human gut. Without coordinated motility, digestion and absorption of dietary nutrients could not take place. To accomplish its functions effectively, the gut needs to generate not just simple contractions but contractions that are coordinated to produce transit of luminal contents (peristalsis). Thus, coordinated gastric contractions are necessary for the emptying of the stomach. The patterns of gastric motility are different in the fed state and the fasting state (Yamada et al. 1995). In the fed state, the stomach contracts at its maximum frequency, 3 cycles/min (cpm) in humans and 5 cpm in dogs. The contraction originates in the proximal stomach and propagates distally toward the pylorus. In healthy humans, the ingested food is usually emptied by 50% or more at 2 hours after the meal and by 95% or more at 4 hours after the meal (Tougas et al. 2000). The pattern of gastric motility changes when the stomach is emptied. The gastric motility pattern in the fasting state undergoes a cycle of periodic fluctuation divided into three phases: phase I (no contractions, 40-60 minutes), phase II (intermittent contractions, 20-40 minutes) and phase III (regular rhythmic contractions, 2-10 minutes).

Gastric motility (contractile activity) is in turn regulated by myoelectrical activity of the stomach. Gastric myoelectrical activity consists of two components, slow waves and spike potentials (Chen and McCallum 1995). The slow wave is omnipresent and occurs at regular intervals whether or not the stomach contracts. It originates in the proximal stomach and propagates distally toward the pylorus. The gastric slow wave determines the maximum frequency, propagation velocity and propagation direction of gastric contractions. When a spike potential (similar to an action potential), is superimposed on the gastric slow wave a strong lumen-occluded contraction occurs. The normal frequency of the gastric slow wave is about 3 cpm in humans and 5 cpm in dogs. A noninvasive method similar to electrocardiography, called electrogastrography, has been developed and applied to detect gastric slow waves using abdominal surface electrodes (Chen and McCallum 1995).

Abnormalities in gastric slow waves lead to gastric motor disorders and have been observed in patients with functional disorders of the gut, such as gastroparesis, functional dyspepsia, anorexia, etc. (Chen and McCallum 1995). Gastric myoelectrical abnormalities include uncoupling and gastric dysrhythmia and can lead to significant impairment in gastric emptying (Lin et al., 1998; Chen et al., 1995a; Telander et al., 1978; You and Chey 1985; Chen and McCallum 1993). Tachygastria (an abnormally high frequency of the gastric slow wave) is known to cause gastric hypomotility (Lin et al., 1998; Chen et al. 1995a; Telander et al., 1978; You and Chey 1985; Chen and McCallum 1993).

Gastric emptying plays an important role in regulating food intake. Several studies have shown that gastric distention acts as a satiety signal to inhibit food intake (Phillips and Powley 1996) and rapid gastric emptying is closely related to overeating and obesity (Duggan and Booth 1986). In a study of 77 subjects composed of 46 obese and 31 age-, sex-, and race-matched nonobese individuals, obese subjects were found to have a more rapid emptying rate than nonobese subjects (Wright et al. 1983). Obese men were found to empty much more rapidly than their nonobese counterparts. It was concluded that the rate of solid gastric emptying in the obese subjects is abnormally rapid. Although the significance and cause of this change in gastric emptying remains to be definitively established, it has been shown that several peptides, including cholecystokinin (CCK) and corticotropin-releasing factor (CRF), suppress feeding and decrease gastric transit. The inhibitory effect of peripherally administered CCK-8 on the rate of gastric emptying contributes to its ability to inhibit food intake in various species (Moran and McHugh 1982). CRF is also known to decrease food intake and the rate of gastric emptying by peripheral injection (Sheldon et al., 1990). More recently, it was shown that in ob/ob mice (a genetic model of obesity), the rate of gastric emptying was accelerated compared with that in lean mice (Asakawa et al., 1999). Urocortin, a 40-amino acid peptide member of the CRF family, dose-dependently and potently decreased food intake and body weight gain as well as the rate of gastric emptying, in ob/ob mice. This suggests that rapid gastric emptying may contribute to hyperphagia and obesity in ob/ob mice and opens new possibilities for the treatment of obesity.

Previous work on antegrade gastrointestinal stimulation has been focused on its effects on a) gastric myoelectrical activity, b) gastric motility, c) gastric emptying, and d) gastrointestinal symptoms (Lin et al., 1998; Eagon and Kelly 1993; Hocking et al., 1992; Lin et al., 2000a; McCallum et al., 1998; Miedema et al., 1992; Qian et al., 1999; Abo et al., 2000; Bellahsene et al., 1992). These studies have conclusively shown that entrainment of gastric slow waves is possible using an artificial pacemaker. Recent studies have indicated that such entrainment is dependent on certain critical parameters, including the width and frequency of the stimulation pulse (Lin et al., 1998). It has also been shown that antegrade intestinal electrical stimulation can entrain intestinal slow waves using either serosal electrodes (Lin et al., 2000a) or intraluminal ring electrodes (Bellahsene et al., 1992).

A need continues to exist for additional feasible and suitable means to treat obesity. Likewise, a need continues to exist for additional feasible and suitable means to treat other gastrointestinal tract disorders.

SUMMARY

To this end, the subject disclosure provides a method of regulating gastrointestinal action in a subject. The method comprises determining an optimum level of total gastrointestinal action in a subject, the total gastrointestinal action including naturally occurring gastrointestinal action and non-naturally occurring gastrointestinal action; positioning a stimulatory electrode relative to the subject so that the stimulatory electrode can generate non-naturally occurring gastrointestinal action; positioning a sensor relative to the subject so that the sensor senses the level of total gastrointestinal action, the sensor being operatively connected to the stimulatory electrode; periodically detecting the level of total gastrointestinal action with the sensor; and periodically generating non-naturally occurring gastrointestinal action with the stimulatory electrode when the detected level of total gastrointestinal action differs from the optimum level until the detected level of total gastrointestinal action substantially equals the optimum level.

The disclosure further provides a method for reducing weight in a subject having a stomach. The method comprises determining an optimum level of total stomach electrical activity in a subject which reduces weight in the subject, the total stomach electrical activity including naturally occurring stomach electrical activity and non-naturally occurring stomach electrical activity; positioning a stimulatory electrode relative to the subject so that the stimulatory electrode can generate non-naturally occurring stomach electrical activity; positioning an electrical activity sensor relative to the subject so that the electrical activity sensor senses the level of total stomach electrical activity, the electrical activity sensor being operatively connected to the stimulatory electrode; periodically detecting the level of total stomach electrical activity with the electrical activity sensor; and periodically generating non-naturally occurring stomach electrical activity with the stimulatory electrode when the detected level of total stomach electrical activity differs from the optimum level until the detected level of total stomach electrical activity substantially equals the optimum level.

Also provided is a method of providing electrical field stimulation to a gastrointestinal organ. The method comprises positioning a first stimulatory electrode in a gastrointestinal organ; positioning a second stimulatory electrode in the gastrointestinal organ, the second stimulatory electrode being positioned at least about two centimeters from the first stimulatory electrode; and electrically stimulating the gastrointestinal organ simultaneously through the first and the second stimulatory electrodes, wherein one of the first and the second stimulatory electrodes has a positive polarity and wherein the other one of the first and the second stimulatory electrodes has a negative polarity, thereby providing electrical field stimulation to the gastrointestinal organ between the first and the second stimulatory electrodes.

Additionally provided is a method of providing electrical potential gradient in a gastrointestinal organ. The method comprises positioning a first stimulatory electrode in a gastrointestinal organ; positioning a second stimulatory electrode in the gastrointestinal organ, the second stimulatory electrode being positioned at least about two centimeters from the first stimulatory electrode; and electrically stimulating the gastrointestinal organ simultaneously through the first and the second stimulatory electrodes, wherein voltage generated by the first stimulatory electrode differs from voltage generated by the second stimulatory electrode, thereby providing an electrical potential gradient in the gastrointestinal organ between the first and the second stimulatory electrodes.

The disclosure further provides a method of stimulating the vagus nerve of a subject. The method comprises positioning a stimulatory electrode in a gastrointestinal organ of a subject; and generating electrical current in the gastrointestinal organ of the subject with the stimulating electrode, wherein the electrical current in the gastrointestinal organ of the subject stimulates the vagus nerve of the subject.

The disclosure also provides a method of placing a device in the gastrointestinal tract of a subject from the exterior of the subject. The method comprises inserting an end of a needle having an interior bore from the exterior of a subject into the gastrointestinal tract of the subject, the gastrointestinal tract of the subject having a center defined by a wall, the wall having a thickness defining an interior wall adjacent to the center and an exterior wall, and the end of the needle being inserted through the wall into the center of the gastrointestinal tract; inserting a device through the interior bore of the needle, wherein the device has an interior wall engaging means and wherein the device is inserted at least until the interior wall engaging means extends beyond the interior bore of the needle; removing the needle; and retracting the device until the interior wall engaging means engages the interior wall of the gastrointestinal tract of the subject, thereby placing the device in the gastrointestinal tract of the subject. Alternatively, the disclosure provides a method of placing a device in the gastrointestinal wall of a subject from the exterior of the subject. This method comprises inserting an end of a needle having an interior bore from the exterior of a subject into the gastrointestinal wall of the subject, the gastrointestinal wall defining a center of a gastrointestinal tract of the subject, the gastrointestinal wall having a thickness defining an interior wall adjacent to the center and an exterior wall, and the needle being inserted until the end of the needle is positioned in the thickness of the wall between the interior wall and the exterior wall; inserting a device through the interior bore of the needle, wherein the device has an engaging means and wherein the device is inserted until the engaging means extends beyond the interior bore of the needle into the thickness of the wall; removing the needle; and -retracting the device until the engaging means engages the thickness of the wall, thereby placing the device in the gastrointestinal wall of the subject.

Additionally, provided herein is a method of treatment for obesity in an individual in need of such treatment comprising positioning a first pair of bipolar stimulatory electrodes in contact with the gastric cavity positioning a second pair of bipolar stimulatory electrodes in contact with the intestinal cavity; and administering electrical stimulation, where the electrical stimulation is effective, at least in part, in activating vagal afferents to modulate gastrointestinal peptide satiety hormones in the individual.

Further provided herein is a method of treatment for an eating disorder, in an individual in need of such treatment, comprising positioning a first pair of bipolar stimulatory electrodes in contact with the gastric cavity; positioning a second pair of bipolar stimulatory electrodes in contact with the intestinal cavity; and administering electrical stimulation, where the electrical stimulation is effective, at least in part, in activating vagal afferents to modulate gastrointestinal peptide satiety hormones in the individual.

Also, provided is a method of regulating the appetite of an individual, in need thereof comprising positioning bipolar stimulatory electrodes in contact with dual sites in the gastrointestinal tract; and administering electrical stimulation, wherein said electrical stimulation is effective, at least in part, in activating vagal afferents to modulate gastrointestinal peptide satiety hormones in said individual.

Certain aspects of the disclosure contemplate method of placing devices in or through a gastrointestinal wall of a subject comprising: inserting a plurality of needles, each comprising a hollow bore, from the exterior of the subject and into or through the gastrointestinal wall; inserting an electrode lead with an insertion axis comprising a plurality of radially spaced arms into the bore of each needle so that the electrode lead comprising a plurality of radially spaced arms is inside the needle; pushing the electrode lead through the bore of each needle into or through the wall of the gastrointestinal tract; and removing the needles; wherein the radially spaced arms are at an angle more acute to the insertion axis of the electrode when inside each needle than when the needles are removed.

Optionally, such methods further comprise inserting the needles at the same time. Optionally, such methods may comprise inserting the needles at different times. Optionally, the electrode leads are inserted into the needles prior to inserting the needles into or through the wall of the gastrointestinal tract from the exterior of the subject. Optionally, the electrode leads are inserted into the needles after inserting the needles into or through the wall of the gastrointestinal tract from the exterior of the subject.

The methods of the disclosure also concern a plurality of needles for insertion into or through the wall of the gastrointestinal tract wherein the needles are physically connected to each other through a bridge. Alternatively or optionally, the disclosure also concerns methods where at least one needle is physically to an insertion rod through a bridge. In methods wherein at least one needle is physically connected to an insertion rod through a bridge, it is contemplated that another needle is present. The other needle may not have an insertion rod. The insertion rod may be placed into the hollow bore needle without an insertion rod. The placement of the insertion rod may take place after the needle without an insertion rod is already inserted through the exterior of the subject into or through the wall of the gastrointestinal tract. The methods involving a needle with an insertion rod further contemplate the steps of: inserting one electrode lead into the hollow bore of the needle physically connected to the insertion rod; pushing the electrode lead through the hollow bore of the needle physically connected to the insertion rod into or through the wall of the gastrointestinal tract; removing the needle physically connected to the insertion rod from the hollow bore of the needle without an insertion rod; inserting one electrode lead into the hollow bore of the needle without an insertion rod; pushing the electrode lead through the hollow bore of the needle without an insertion rod into or through the wall of the gastrointestinal tract; and removing the needle without an insertion rod.

Other aspects of the disclosure contemplate a method of regulating the appetite of an individual, in need thereof comprising: positioning bipolar stimulatory electrodes in contact with dual sites in the gastrointestinal tract along the afferent vagus neural pathway; and administering electrical stimulation, wherein said electrical stimulation is effective, at least in part, in activating the vagal afferents to modulate gastrointestinal peptide satiety hormones in said individual. Optionally, such a method may further comprise administering a phased pulse regimentation of said electrical stimulation which progresses from said first pair of electrodes to said second pair of electrodes. Optionally the dual sites in the gastrointestinal tract are the gastric cavity and a dudenol cavity. Optionally, the peptide hormones are selected from the group consisting of ghrelin, obestatin, CCK-8 and PYY. Optionally, the method may be used in individuals suffering from obesity, compulsive eating, anorexia or bulimia.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

A) pulse trains (IGS-3 ms): 40 Hz, 3 ms, 6 mA, 2 seconds on and 3 seconds off; B) long pulses: 9 cpm, 300 ms and 6 mA.

Figure 19A:
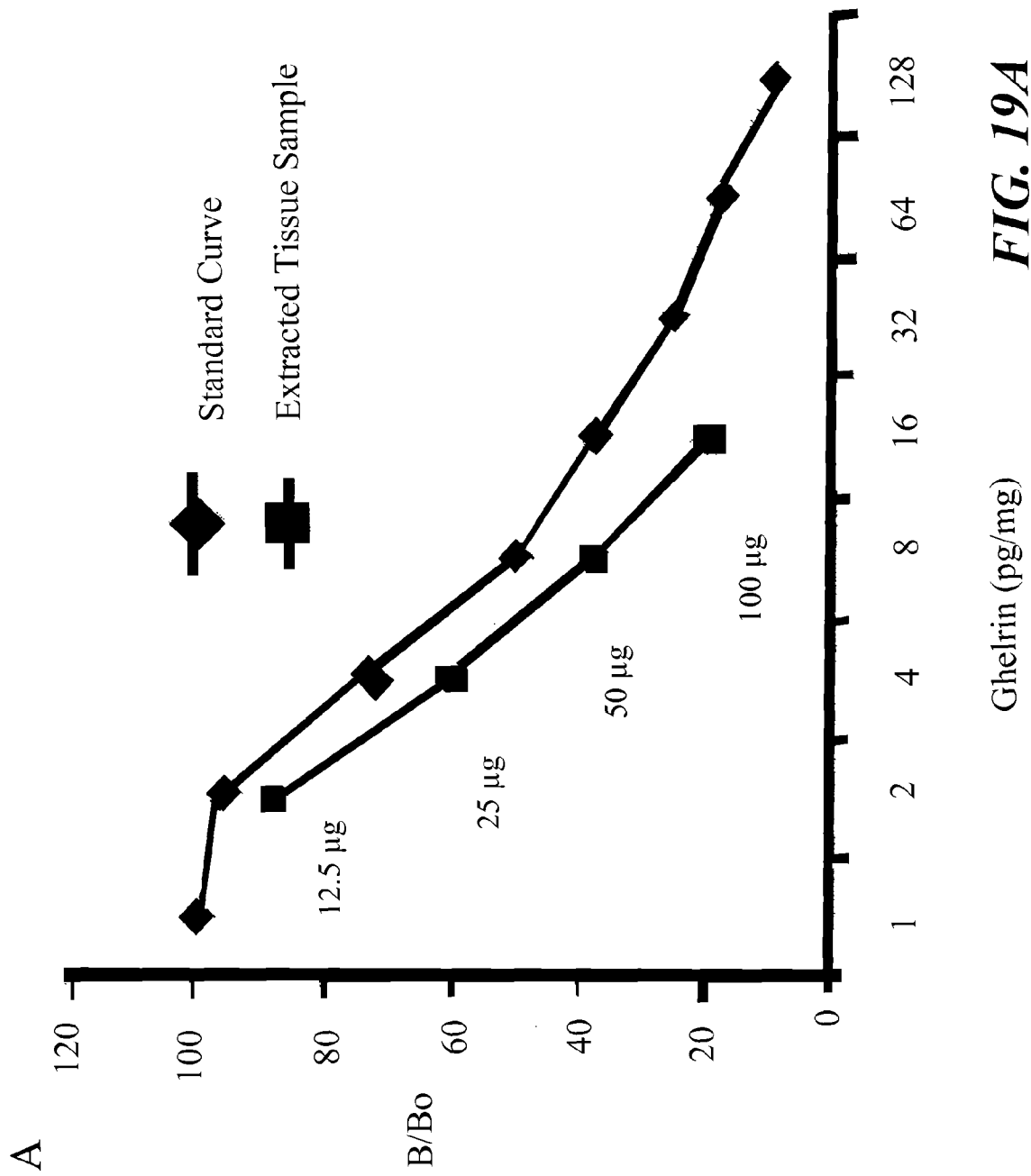
Figure 19B:
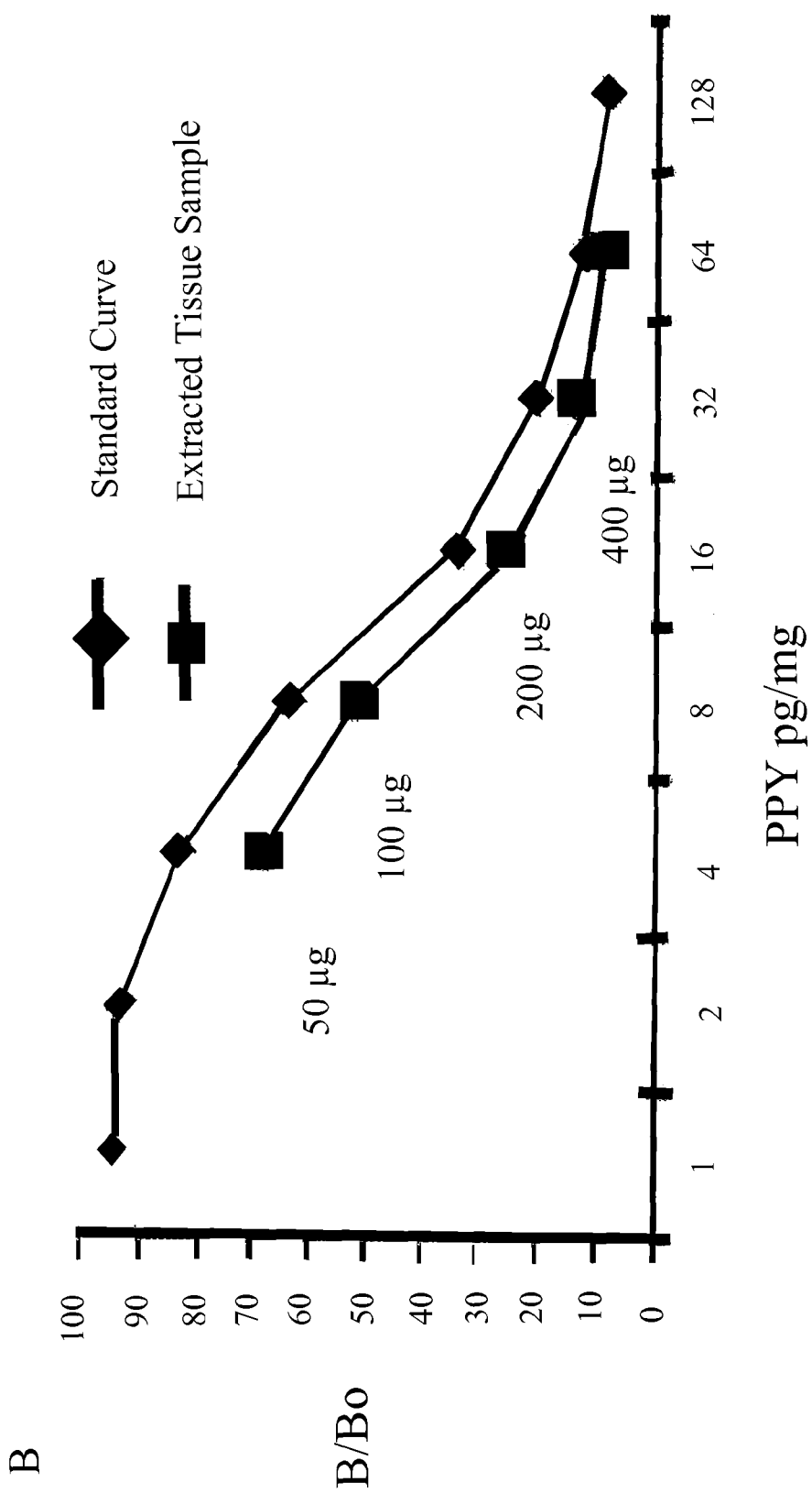
Figure 19C:
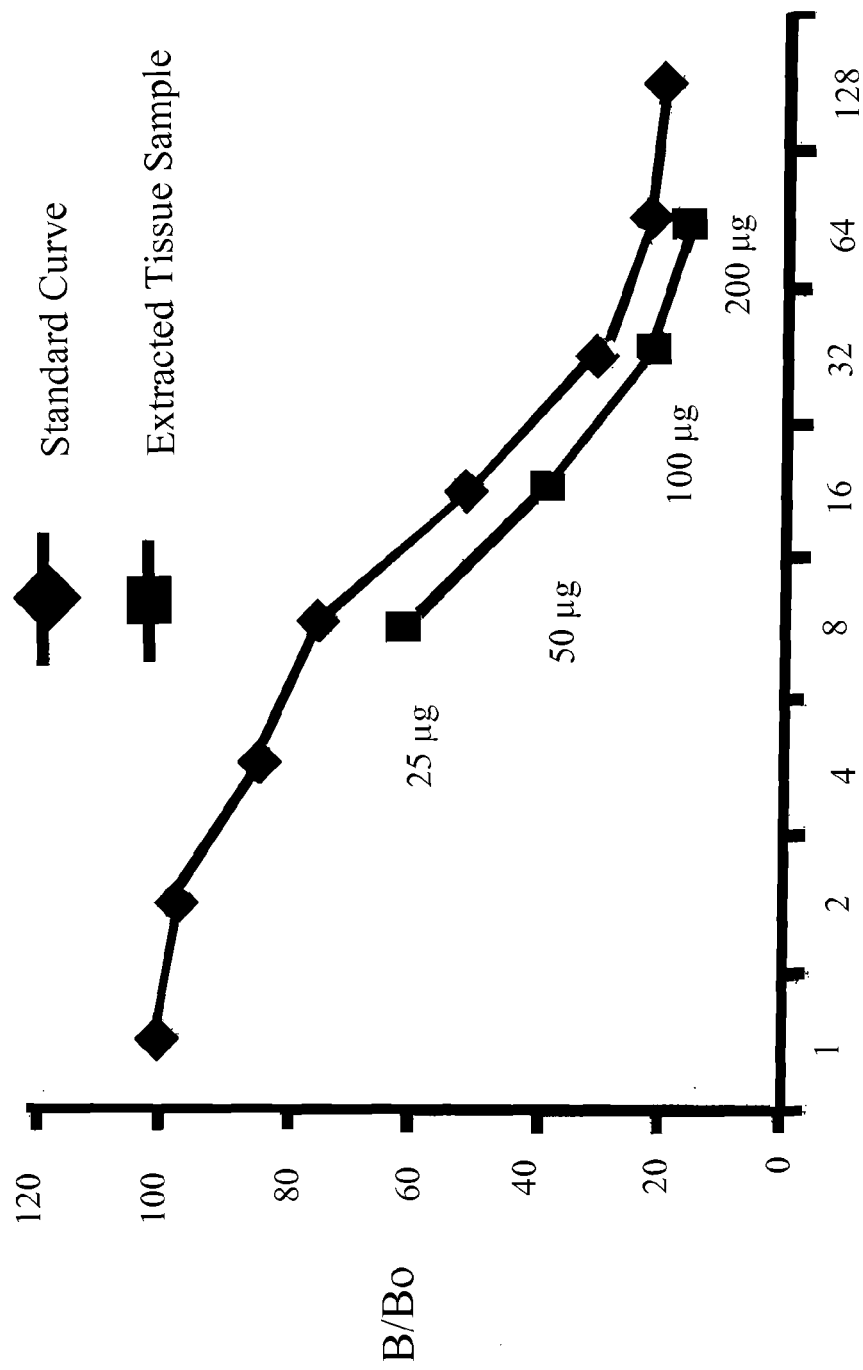

FIG. 19 shows competition of $^{125}I$ peptides binding to peptide antibodies by gastric fundus tissue extracts, duodenum tissue extracts and distal colon tissue extracts. $^{125}I$ peptides were incubated with peptide antibodies with different dilutions of tissue extracts and the peptides standard. Pg, pictograms; B, bound; B, total bound. A: ghrelin, B: CCK-8, C: PYY.

Figure 20:
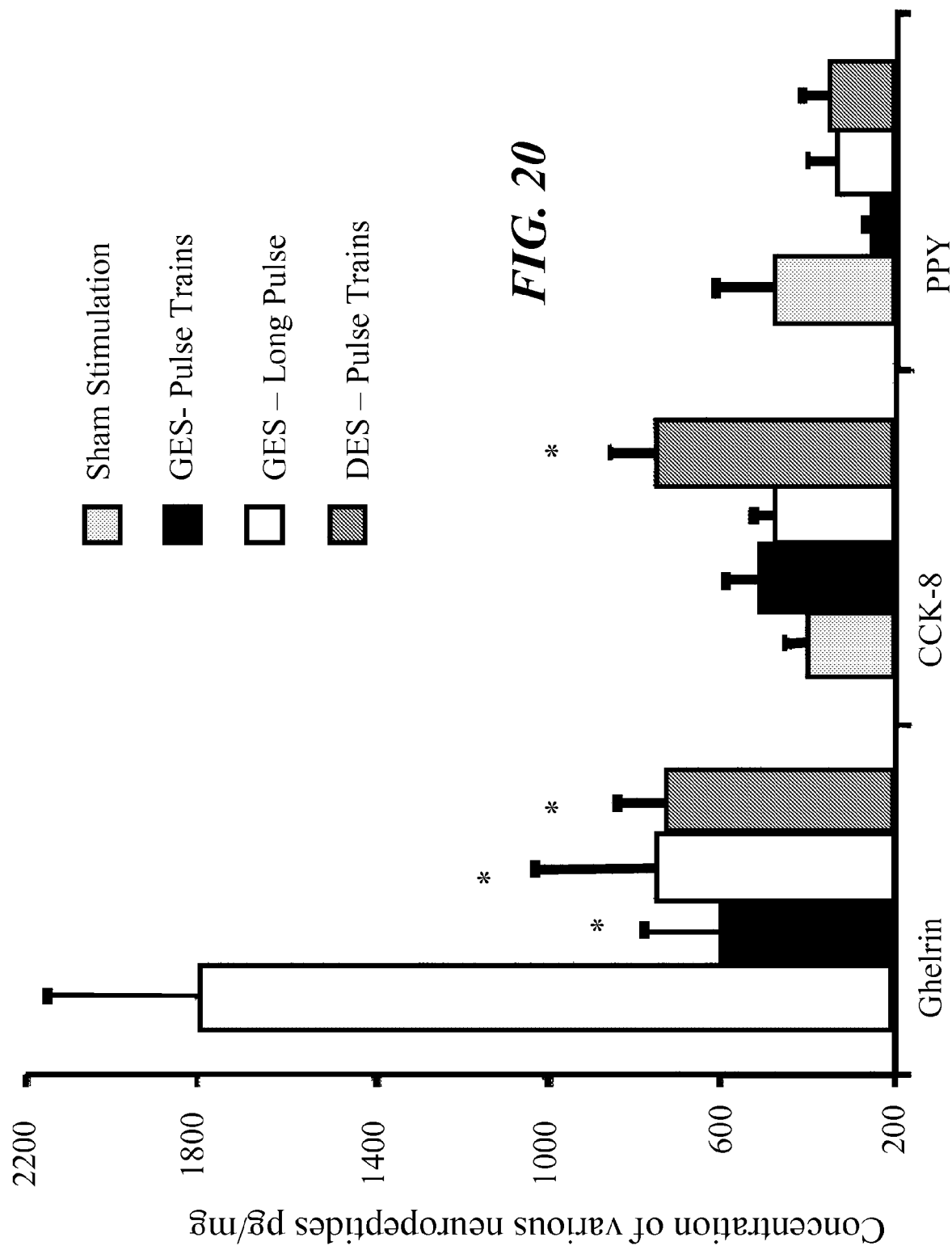

FIG. 20 demonstrates concentrations of ghrelin in the gastric fundus tissue, CCK-8 in duodenum tissue and PYY in distal colon tissue after gastrointestinal electrical stimulation with different parameters and different locations. Values are mean±SE. *p<0.05.

FIG. 21A-F shows various electrode leads with radially spaced arms in various configurations inserted into and through the hollow bore of a needle.

Figure 22:
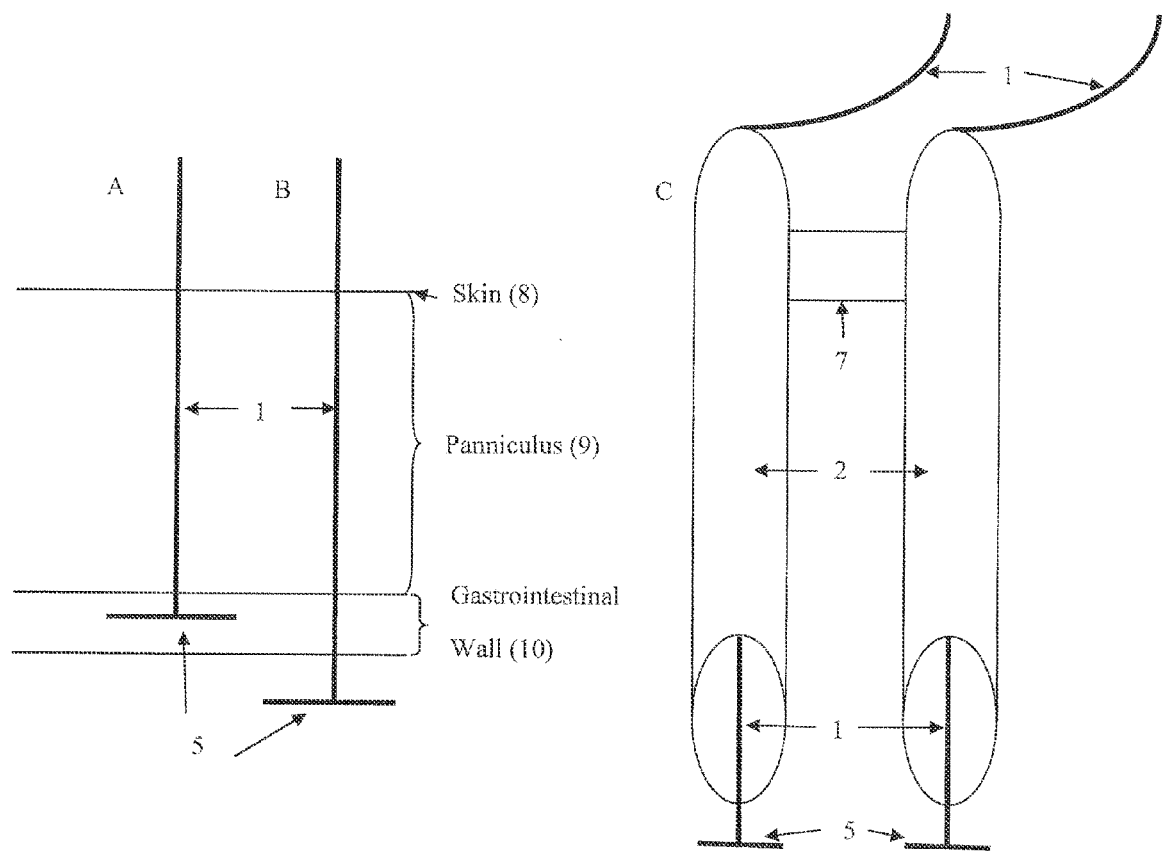

FIG. 22 A, B shows electrode leads with radially spaced arms inserted through the skin, panniculus and gastrointestinal wall after removal of insertion needles.

FIG. 22C shows bridged insertion needles.

FIG. 23A-D shows methods and devices for using a needle with a guide rod for electrode leads with radially spaced arms.

Figure 24:
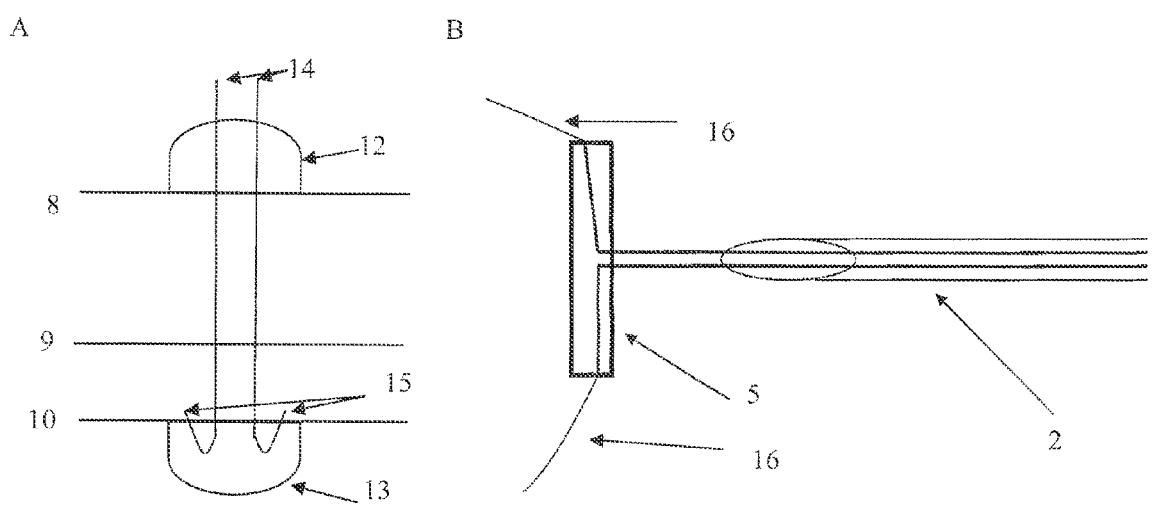

FIG. 24A shows a method of placing gastrointestinal leads with a percutaneous endoscopic gastronomy type device.

FIG. 24B shows conductive wire through an electrode lead with an insertion axis and a plurality of radially spaced arms.

LIST OF REFERENCE NUMERALS 1 electrode lead with an insertion axis
2 needle
3 hollow bore
4 entrance tip
5 first or a single pair of radially spaced arms
6 second or additional pair of radially spaced arms
7 bridge
8 skin
9 panniculus
10 gastrointestinal wall
11 guide rod
12 skin bolster
13 gastric bolster
14 plurality of electric leads
15 lead ends
16 conductive wire
17 second needle

DETAILED DESCRIPTION OF THE ILLUSTRATIVE EMBODIMENTS a. Introduction

The current disclosure concerns methods of regulating gastrointestinal action in a subject through the use of electrical stimulation. Electrical stimulation of the gastrointestinal tract has been proposed to treat motility related disorders and other gastrointestinal diseases. A number of forms of electrical stimulation are known to exist for therapeutic purposes. Electrical pacing of the gastrointestinal tract is generally defined as a periodic electrical stimulation that captures and/or controls the frequency of the pacesetter potential or slow wave activity of the intestinal organ (including in a retrograde direction). Electrical contractile stimulation generally refers to stimulation that directly causes or results in muscular contraction associated with the gastrointestinal tract.

There have been a number of reports on gastric electrical stimulation for the treatment of gastrointestinal motility disorders in both dogs and humans (U.S. Pat. Nos. 5,423,872, 5,690,691, and 5,836,994; PCT No. PCT/US1998/026506; Bellahsene et al., 1992; Mintchev et al., 1998; Mintchev et al., 1999; Mintchev et al., 2000; Chen et al., 1998; Chen et al., 1995c). These disorders are characterized by poor contractility and delayed emptying and the aim of electrical stimulation in this setting is to normalize the underlying electrical rhythm and improve these parameters. Gastric emptying plays an important role in regulating food intake. Several studies have shown that gastric distention acts as a satiety signal to inhibit food intake (Phillips and Powley 1996) and rapid gastric emptying is closely related to overeating and obesity (Duggan and Booth 1986). Obese subjects have a more rapid emptying rate than non-obese subjects (Wright et al., 1983). In general, this is done by antegrade or forward gastric (or intestinal) stimulation. Previous work on antegrade gastrointestinal stimulation has been focused on its effects on gastric myoelectrical activity, gastric motility, and gastric emptying, (Lin et al., 1998; Eagon and Kelly 1993; Hocking et al., 1992; Lin et al. 2000a; McCallum et al., 1998; Miedema et al., 1992; Qian et al., 1999; Abo et al., 2000; Bellahsene et al., 1992).

The mechanism by which gastric electrical stimulation for the treatment of obesity is achieved is not clear but involves impairment of physiological gastric electrical activity, or slow waves. Gastric electrical stimulation indices gastric distention, reduces gastric accommodation and inhibits stomach peristalsis in the fed state. The stimulation-induced gastric distention activates the stretch receptors and, thus, increases satiety before the meal. The reduced gastric accommodation is anticipated to increase satiety during gastric emptying and therefore increase satiety between meals. Gastric electrical stimulation modulates neuronal activities in the brain via alterations in gastric motility. Gastric electrical stimulation also modulates satiety hormones. Satiety signals are, for the most part, regulated by peptides synthesized and released from specialized enteroendocrine cells in the gastrointestinal tract. Gastrointestinal neuroendocrine communications between the periphery and the brain regulate energy balance and ingestive behaviors by acting as modulating gastrointestinal satiety signals. The vagus nerve is the dominant nerve of the gastrointestinal tract (see, e.g., Berthoud et al., "Morphology and distribution of vagal afferent innervation of rat gastrointestinal tract," Soc. Neurosci. Abstr., 17 (2), 1365, 1991). Visceral sensory information is transmitted to the brain through the afferent vagus nerve. Gastrointestinal peptide hormones are integral contributors to the numerous peripheral signals that regulate food intake and energy balance. Gastrointestinal peptide hormones such as ghrelin, obestatin, cholecystokinin-8 (CCK-8) and peptide YY (PYY) that are synthesized and released from the gastrointestinal tract have multi-potential capabilities through a complex interplay from mechanoreceptor and chemoreceptor signaling events to ultimately regulate satiety and appetite. These hormones can interact locally with specific receptors on vagal afferent axons passing to the brain. These gut peptides can also be released directly into the bloodstream, allowing their delivery to distant sites of action to relay information regarding nutritional status.

b. Terminology

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings and/or examples making apparent to those skilled in the art how the several forms of the disclosure may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition.

Figure 1:
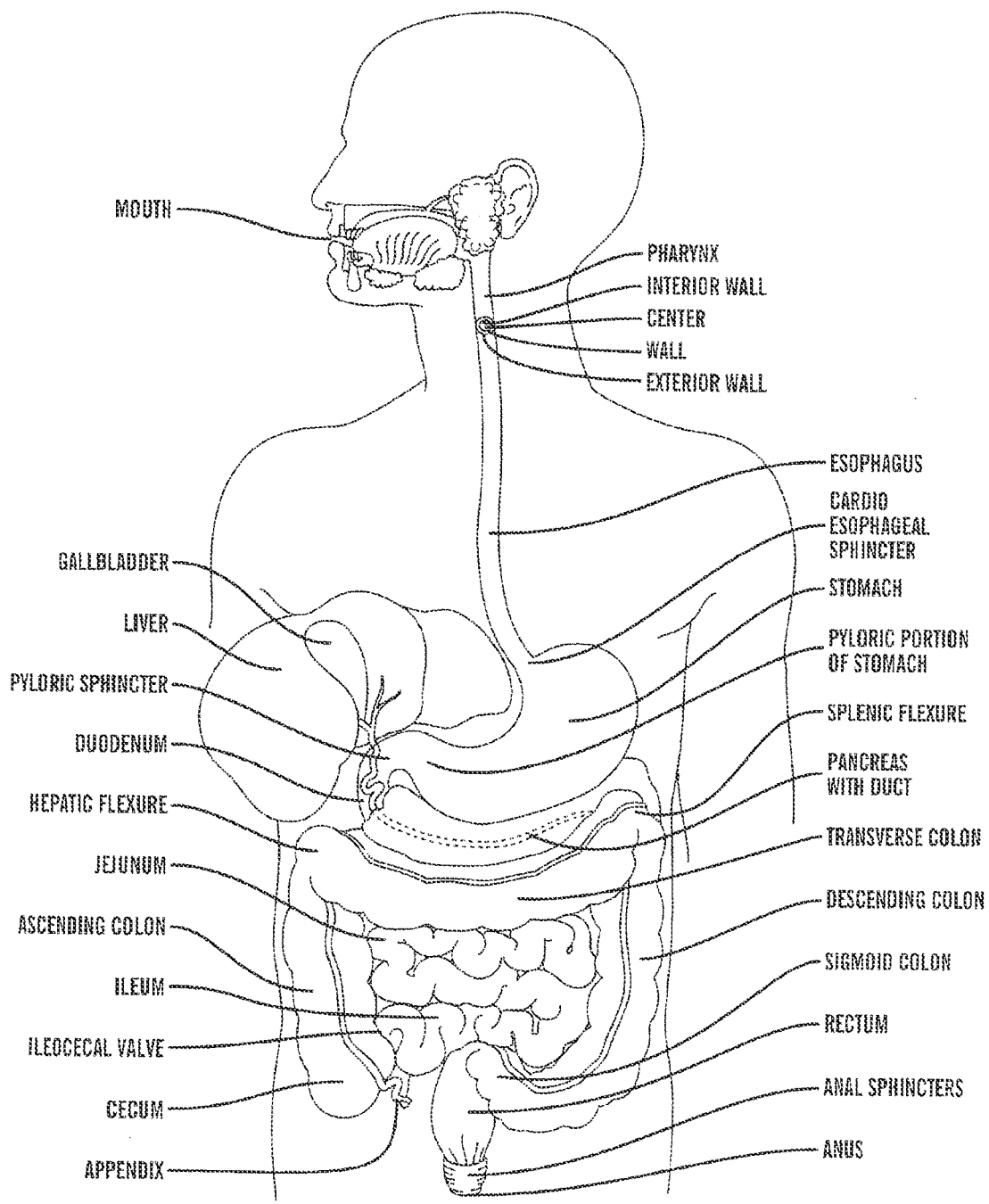
FIG. 1 is a general diagram of the gastrointestinal tract of a human subject.

The term "gastrointestinal tract" (GI tract) in certain instances may refer to the "gut" or the "alimentary canal" that is a continuous, coiled, hollow, muscular tube that winds through the ventral body cavity (FIG. 1). It is open to the external environment at both ends. In a human, the organs of the gastrointestinal tract ("gastrointestinal organs") generally include the mouth, pharynx, esophagus, stomach, small intestine (duodenum, jejunum, and ileum), and large intestine (cecum, appendix, colon, rectum, and anal canal). The large intestine leads to the terminal opening, or anus.

The term "gastrointestinal wall" in certain instances may refer to the continuous, coiled, hollow, muscular tube that is the gastrointestinal tract. The wall generally defines the center (lumen) of the GI tract (the hollow portion of the tube). The wall has a thickness defining an interior wall adjacent to the center of the GI tract and an exterior wall (see FIG. 1 insert).

The term "gastrointestinal action" in certain instances may refer to any GI actions which are generated by electrical activity. Thus, gastrointestinal action includes, for example, gastrointestinal electrical activity, gastrointestinal contractile activity (such as stomach contractile activity), gastrointestinal motility, gastric emptying, gastrointestinal pressure, gastrointestinal impedence, and afferent nerve activity (including vagal nerve, sympathetic nerves, and spinal nerves).

The term "subject" in certain instances may refer to an animal, including a human. For such non-human animal subjects, the gastrointestinal tract, as used herein, refers to that non-human animal's known GI tract and GI organs.

The term "optimum level" in certain instances may refer to a pre-determined target, which is determined based on the desired outcome. For example, in RGES (see below), the definition of optimization is based on an optimal combination of efficacy, safety and feasibility. That is, the optimal RGES settings are those that result in a significant reduction in food intake (efficacy) but do not induce undesired symptoms, such as nausea or vomiting (safety) with minimal energy (maximally feasible for an implantable device). Iterative adjustments of stimulation parameters are made to achieve this result. For any particular gastrointestinal action, an "optimum level" or desirable level can be determined by monitoring the appropriate GI action. As another example, an appropriate amount of GI pressure at the esophageal sphincter can be determined which prevents reflex of stomach juices into the esophagus, while still allowing the passage of food items into the stomach. With this predetermined "optimum level", a stimulatory electrode can be established with a sensor to maintain this optimum level. The optimum level is thus fact and subject specific, but readily determinable with routine experimentation, taking into account the goal of an optimal combination of efficacy, safety and feasibility.

The term "total gastrointestinal action", in certain instances may refer to the sum total of levels of any naturally occurring gastrointestinal action and levels of any non-naturally occurring gastrointestinal action. Naturally occurring gastrointestinal action refers to spontaneous gastrointestinal action that is present in a subject prior to a particular treatment. Non-naturally occurring gastrointestinal action refers to non-spontaneous gastrointestinal action generated by the hand of man or otherwise caused to occur by the particular treatment of the subject. It is important to note that the non-naturally occurring gastrointestinal action which is generated and which is non-spontaneous GI action may in fact be identical (in a physiological sense, for example) to a naturally occurring GI action once it has been generated. For example, a subject may have a naturally occurring level of stomach electrical activity of "X". A stimulatory electrode is positioned to generate a non-naturally occurring level of stomach electrical activity of "Y". The total gastrointestinal action, which is stomach electrical activity in this example, is therefore "X+Y".

The term "stimulatory electrode" in certain instances may refer to a conductor of electricity through which current enters a medium (a subject), whereas the term "sensor" can refer to a conductor of electricity through which current leaves a medium (a subject). Typically, for gastrointestinal uses, the stimulatory electrodes and sensors are constructed of insulated wires such as are used for cardiac pacing wires. The stimulatory electrode is electrically connected (i.e., conductively connected) to a source of electrical current (often referred to as a pacemaker where a set pattern of electrical current is delivered), and the sensor is electrically connected to a device for determining the level of electrical current "sensed" by the sensor (an electrical recorder, for example). The stimulatory electrode is thus used to "generate" electrical current and the sensor is thus used to "detect" electrical current. Note that the stimulatory electrode can be used to "generate" electrical current, which is itself a defined "gastrointestinal action", but the generation of electrical current can also produce other gastrointestinal actions (such as, for example, stomach contraction or esophageal pressure). The language "generating" GI action is thus intended to cover both concepts, i.e. the generation of the initial electrical current and the ultimate gastrointestinal action which is "generated" as a result of the current (i.e. the contraction or pressure).

The engaging means for the electrode in certain instances may refer to any suitable means that would allow for the successful engagement of the electrodes to the mucosa. These include but are not limited to sutures, barbs, expandable hooks, suction based fasteners arranged at the distal tip of the electrodes, and/or the like, as would be understood by one of ordinary skill in the art.

The term "differs from" may refer to a statistically significant variation between two compared values, and therefore does not always require a difference in orders of magnitude. It should be apparent that where small values are compared, statistically significant variations can likewise be very small, and where large values are compared, statistically significant variations can be large. Conversely, "substantially equals" refers to a statistically insignificant variation between two compared values. Synchronization or synchronized refers to applying the long pulse and/or short pulse electrical stimulation substantially concurrently with the occurrence of the gastric slow wave of the subject.

The term "operatively connected" in certain instances may refer to the connection between the stimulatory electrode and the sensor, and indicates that the operation of one is connected to the operation of the other. In particular, the sensor connects to a device which determines the level of electrical current sensed by the sensor. A representation of that level is then fed to the source of electrical current that is electrically connected to the stimulatory electrode. The source of electrical current is provided with a programmable computer circuit that enables the level from the sensor to determine, or dictate, the operation of the source (i.e., electrical current is generated by the source and fed through the stimulatory electrode in response to and an in relation to the amount of the level of electrical activity sensed by the sensor). Thus, the "operatively connected" stimulatory electrode and sensor enable the retrograde feedback concept to occur.

Figure 9:
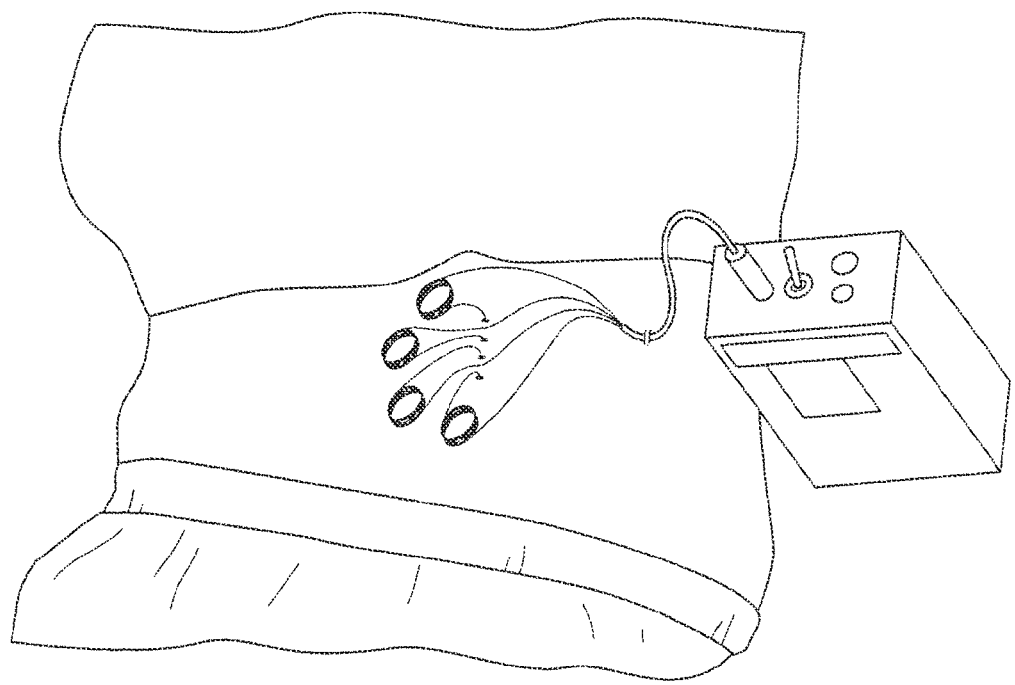
FIG. 9 illustrates a typical portable pacemaker in use.
Figure 10:
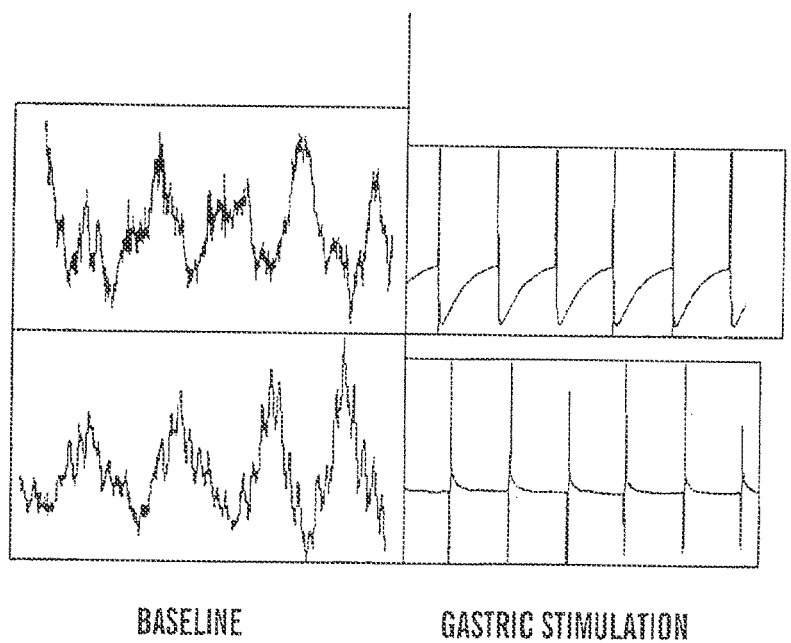
FIG. 10 illustrates gastric pacing in a rat.

The term "positioning" a stimulatory electrode or a sensor in certain instances may refer to the placement of a stimulatory electrode or sensor on or in a subject. In the example of gastrointestinal pacing, the teflon coated wires which are the stimulatory electrode and the sensor may be "positioned" as show in FIGS. 9 and 16. Placement or positioning of stimulatory electrodes can be accomplished by laparoscopic, endoscopic or surgical means. In general, laparoscopic placement of electrodes is performed by inserting a scope through one trocar or sheath and the electrode through one or more other trocars or sheaths. The trocars are sleeves which are inserted through a body opening which may be a surgically made opening or portal through the skin, muscle and peritoneal membrane. Often the body cavity, such as the abdominal peritoneal area is inflated with low pressure carbon dioxide. An insufflation pressure of about 12 millimeters of mercury or less is maintained during the operation by a sealing membrane located in the trocar opening comprising a thin rubber material having a small diameter hole of approximately 3 millimeters therein. The electrodes are inserted through the membrane hole which stretches to accommodate the larger size thereby forming and effective seal.

The term "Electrical field stimulation" in certain instances may refer to the generation of an "electrical field", which indicates that the area of distribution of the electrical current from the stimulation encompasses the entire area between and/or surrounding two or more stimulatory electrodes, and "field" is used to imply that the two or more stimulatory electrodes are positioned at least about three centimeters apart (thus the term "field" to differ from prior stimulations where the two electrodes of a pair are positioned in close proximity to one another and do not generate a "field").

Electrical stimulation in certain instances may refer to an electrical signal, which includes a train of pulses. A train of pulses refers to a method in which the stimulus is composed of repetitive trains of short pulses derived from a combination of two signals, a) a continuous short pulse with high frequency (in the order of 5 to 150 Hz), and b) control signal to turn the pulses on or off, such as "X" seconds on and "Y" seconds off. The addition of "X" and "Y" then determines the frequency of the pulse train. A frequency approximately equal to the physiologic frequency of stimulation will be performed using trains of pulses. The train will be set on for a period of 0.1 s to 5 seconds and set off for a period of 0 to 10 min. The pulses within a train have a frequency of 5 to 150 Hz width of 0.1 to 2 ms and amplitude of O.1 mA to 10 mA or the corresponding voltages that will produce the described current. The methods of providing electrical field stimulation to a gastrointestinal organ are disclosed in WO/2001/076690 (GASTROINTESTINAL ELECTRICAL STIMULATION) which is hereby incorporated by reference herein. A discussion of trains of short pulse electrical stimulation is provided in Zhang et al., *Current treatments of Gastroenterol.*, 9: 351-360 (2006), which is hereby incorporated by reference herein.

The term "long pulse" electrical stimulation in certain instances may refer to an electrical signal which has a long width, such as in the order of from about 1 to about 900 milliseconds, and has a frequency equal to or a few times higher than the physiologic frequency of the gastric slow wave of the subject. For treating gastrointestinal motility disorders, the frequency of stimulation is typical equal to the frequency intrinsic slow waves; whereas for treating obesity, it is usually a higher than the physiological frequency of the gastric slow waves.

The term "short pulse" electrical stimulation in certain instances may refer to an electrical signal which has a short width, such as in an order of from about 50 to about 999 microseconds, or about 100 to about 300 microseconds and having a frequency from about 5 Hz to about 500 Hz.

The term "synchronization or synchronized" as it relates to long pulse or short pulse may refer to applying the long pulse and/or short pulse electrical stimulation substantially concurrently with the occurrence of the gastric slow wave of the subject.

The term "periodically" in certain instances may refer to evenly or unevenly spaced time intervals.

The term "device" in certain instances may refer to any suitable item which can readily be and is desirable to be placed in the GI tract. Such devices can include, for example, stimulatory electrodes and sensors for use in the RGES method of the subject disclosure. Such devices could also include a small balloon to be used to provide pressure within the esophagus or small/large intestine. A small gauge for measurement of pressure could be a device in accordance with the subject disclosure.

The term "visceral pain" in certain instances may refer to pain or discomfort that is centered in the upper abdomen and/or the lower abdomen, for example, pain associated with dyspepsia or pain due to irritable bowel syndrome. For example visceral pain may be caused by distention or other noxious stimulation of a gastrointestinal organ. Likewise, the term "reducing visceral pain" refers to reducing or eliminating one or more of the symptoms of visceral pain. Methods of measuring the reduction of visceral pain in a non-human subject may include measuring a number of behavioral responses to visceral pain before and after gastrointestinal electrical stimulation is provided. In animals the responses measured include rapid breathing, nausea, vomiting, burping, licking lips, hi a human subject, the reduction and/or elimination of symptom of visceral pain is measured by evaluation of the subject by, for example verbal expression of intensity of pain on a scale such as 0-10. Although not meaning to be bound by theory, gastrointestinal pain of a subject is largely mediated via the sympathetic (spinal cord) pathway. Gastrointestinal electrical stimulation, as used in the present disclosure, alters sympathetic nerves, such as the spinal afferent neurons. Accordingly, gastrointestinal electrical stimulation treats or reduces pain of a subject by blocking the sympathetic pathway of the subject.

c. Satiety Hormones

The mechanism by which gastric electrical stimulation for the treatment of obesity is achieved is not clear but involves impairment of physiological gastric electrical activity, or slow waves. Gastric electrical stimulation indices gastric distention, reduces gastric accommodation and inhibits stomach peristalisis in the fed state. The stimulation-induced gastric distention activates the stretch receptors and, thus, increases satiety before the meal. The reduced gastric accommodation is anticipated to increase satiety during gastric emptying and therefore increase satiety between meals. Gastric electrical stimulation modulates neuronal activities in the brain via alterations in gastric motility. Gastric electrical stimulation also modulates satiety hormones. Satiety signals are, for the most part, regulated by peptides synthesized and released from specialized enteroendocrine cells in the gastrointestinal tract. Gastrointestinal neuroendocrine communications between the periphery and the brain regulate energy balance and ingestive behaviors by acting as modulating gastrointestinal satiety signals. The vagus nerve is the dominant nerve of the gastrointestinal tract (see, e.g., Berthoud et al., "Morphology and distribution of vagal afferent innervation of rat gastrointestinal tract," Soc. Neurosci. Abstr., 17 (2), 1365, 1991). Visceral sensory information is transmitted to the brain through the afferent vagus nerve. Gastrointestinal peptide hormones are integral contributors to the numerous peripheral signals that regulate food intake and energy balance. Gastrointestinal peptide hormones such as ghrelin, obestatin, cholecystokinin-8 (CCK-8) and peptide YY (PYY) that are synthesized and released from the gastrointestinal tract have multi-potential capabilities through a complex interplay from mechanoreceptor and chemoreceptor signaling events to ultimately regulate satiety and appetite. These hormones can interact locally with specific receptors on vagal afferent axons passing to the brain. These gut peptides can also be released directly into the bloodstream, allowing their delivery to distant sites of action to relay information regarding nutritional status.

Acute gastric electric stimulation with selected stimulation parameters significantly modulates gastric peptide hormones related to satiety and appetite in the gastrointestinal tissues. Gastric electrical stimulation (pulse trains and long pulse) can significantly decrease the ghrelin concentrations in the gastric fundus. Electric stimulation of the duodenum may significantly increase the CCK-8 concentrations in the duodenum. Neither gastric electric stimulation nor electric stimulation of the duodenum appear to alter the concentration of gastric obestatin or distal colon PYY.

Gastrointestinal electrical stimulation has increased satiety and decreased food intake with resultant weight loss in clinical and animal studies. Gastric pacing in animals caused altered eating behavior and weight loss. Additionally, specific stimulation of the duodenum may result in inhibitory effects on gastric motility/secretion, fat absorption, gastric emptying and food intake, yielding weight loss in animals and humans.

Gastrointestinal electrical stimulation has been demonstrated to impact a variety of complex pathophysiologic mechanisms, including inhibition of the intrinsic gastric electrical activity and gastrointestinal motility, direct effects on the central nervous system, and hormonal modulation of satiety and/or appetite. Gastrointestinal electrical stimulation alters the plasma levels of selected gastrointestinal satiety-related peptides and also alters the expression of neuropeptides in neurons of the hypothalamus. Long term treatment with IGS reduces blood levels of CCK and somatostatin, and basal levels of plasma GLP-1 and leptin with no effect on plasma ghrelin levels. Acutely, two hour gastrointestinal electrical stimulation decreases plasma levels of insulin and glucose in dogs. Recently, studies have shown that 2 hour treatment of gastrointestinal electrical stimulation increases the expression of oxytocin and decreases the expression of ghrelin in the hypothalamus in rats.

Gastrointestinal electrical stimulation has been reported to change eating behaviors in animals and induce meal-related satiety in obese patients, may operate through direct modulation of the peptide hormones that regulate GI satiety signals. These interactions are largely mediated by the gut-brain peptides such as ghrelin, obestatin, peptide YY (PYY) and CCK-8 through negative and positive feedback loops that maintain energy homeostasis. Previous studies have identified CCK-8, PYY 3-36 and obestatin, anorexigenic peptides and ghrelin, an orexigenic peptide, as promising therapeutic targets in the battle against obesity.

Ghrelin increases can induce weight gain and adiposity by stimulating food intake and decreasing fat use or energy expenditure. Obestatin is a new ghrelin-associated peptide isolated from the rat stomach. Contrary to the appetite-stimulating effects of ghrelin, it suppresses food intake and decreases body weight gain. Cholecystokinin-8 (CCK-8) is an important GJ satiety signal; Peptide YY (PYY-3-36) is also a gut-derived hormone with reported anorectic properties. The gastric fundus ghrelin levels were significantly decreased by both GES and DES with all the studied parameters. A reduction of ghrelin and its subsequently reduced food intake would induce a state of negative energy balance, which may well contribute to the weight loss resulting from gastrointestinal electrical stimulation. This finding suggests that the inhibitory effect of electrical stimulation on food intake may be partly due to its influence on inhibiting ghrelin synthesis in the stomach.

Ghrelin is the only GI hormone known to increase food intake; it affects all aspects of the energy homeostasis system in a concerted manner to promote weight gain. Ghrelin plays a role in determining food intake from meal to meal and therefore it would be desirable to have an acute or rapid impact on its tissue levels. Expression and secretion of ghrelin are increased by fasting and are reduced by feeding. Previous studies have shown that acute ghrelin blockade in adult animals decreases spontaneous food intake leading to weight loss in the longer studies.

Total gastrectomy in mice, which decreased the total ghrelin level by 80%, caused reductions in body weight, fat mass and lean mass. Gastric bypass surgery typically suppresses or at least constrains ghrelin levels. It is possible that an emerging anti-obesity treatment, intermittent stimulation parameters by implantable gastrointestinal electric stimulation devices and/or those electrical stimulation devices specifically targeting the duodenum may lead to persistently diminished ghrelin levels; this may in turn contribute to appetite reduction and durable success of weight management.

A significant increase in duodenal CCK-8 concentration has been observed with electrical stimulation of the duodenum. CCK-8 was the first gut hormone found to inhibit food intake. CCK-8 is produced by mucosal endocrine cells in the duodenum and released after eating. Its effects on feeding appear to depend upon local actions near the site of release in stimulating vagal afferent fibers rather than on distant sites relying on humoral transport. In this study, electric stimulation of the duodenum may directly increase duodenal CCK-S concentrations where CCK-S is produced and/or released. Gastrointestinal signals that influence the brain to stop an ongoing meal are collectively called satiety signals. CCK-8 appears to be a short-term, meal-reducing satiety signal. Following its release, CCK-8 elicits multiple effects on the gastrointestinal system; it inhibits ingestion and eventually brings a meal to termination. As a neuromodulator and/or neurotransmitter in both the central nervous system and the periphery, this brain-gut peptide plays a role in the regulation of gastrointestinal responses to nutrient ingestion and forms a negative feedback loop for the control of feeding behaviors in animals and humans. A direct control that inhibits meal size can function by amplifying satiety signals or by some combination of these actions. Factors that increase CCK-8 levels may have a potential in the treatment of obesity.

Obestatin levels in the stomach tissue and PYY levels in the distal colon have not been demonstrated to be affected by acute electrical stimulation. Obestatin, a 23-amino acid peptide encoded by the ghrelin gene and isolated from the rat stomach, opposes ghrelin's effects on food intake. It is not considered a meal-related signal since serum levels of obestatin were found to be constant in fasting and refeeding with food or water containing dextrose. It is possible that direct acute electrical stimulation may primarily affect meal-related satiety signals.

PYY may be an important anorexigenic substance. It is mainly synthesized and secreted by the ileum and large intestine. Gastrointestinal electric stimulation may activate or inhibit local enteroendocrine cells to synthesize gut peptides.

Acute electrical stimulation of the stomach or duodenum decreases appetite-stimulating gut hormones and increases appetite-inhibiting gut hormones in gastric and duodenal tissues. Gastrointestinal stimulation decrease ghrelin levels in the gastric fundus. Electric stimulation of the duodenum may increase CCK-8 levels in the duodenum. Alterations in the synthesis and secretion of these satiety-related peptides may contribute significantly to the altered eating behaviors associated with acute gastrointestinal electric stimulation in experimental and clinical studies. Manipulation of hormonally related satiety by electrical stimulation provides an emerging and promising treatment of obesity. Dual electrical stimulation of the gastrointestinal organs via the stimulatory electrodes can be provided in a phased sequential manner. A particular advantage of using multiple site, phased electrical stimulation is that lower levels of current are likely to be satisfactory since the phased relationship of the signals will be additive in effect on the organs. Hence, the dual stimulation provided by discrete electrodes, positioned along the afferent vagal neural pathways of the stomach and the duodenum may be preferably controlled to sequentially provide pulses of increasing frequency and amplitude. The pulsing of electrodes may be phased relative to one another. For example the second pair of electrodes may lag the pulse administered by the first pair of electrodes or vice-versa. This is but one example of the phased administration of the electrical stimulation. Similar phased regimen of administering electrical stimulation may be used for more than two pair of electrodes relative to each other.

d. Aspects of the Disclosure

Particular aspects of the present disclosure concern a method for regulating gastrointestinal action in a subject. Such a method may comprise determining an optimum level of total gastrointestinal action in a subject which may itself include either or both naturally occurring and non-naturally occurring action and positioning one or more electrodes, such as stimulatory electrodes, relative to the subject so that the electrode can generate non-naturally occurring gastrointestinal action.

Optionally the method above may additionally include positioning a sensor relative to the subject so that the sensor senses the level of total gastrointestinal action. In certain aspects, the sensor may be operatively connected to the electrode. Optionally, the method may include periodically detecting the level of total gastrointestinal action with the sensor. Still further, the method may include periodically generating non-naturally occurring gastrointestinal action with the electrode. In certain aspects, the generation of non-naturally occurring gastrointestinal action may take place when the detected level of total gastrointestinal action differs from the optimum level. Optionally, the generation of non-naturally occurring gastrointestinal action may take place until the detected level of total gastrointestinal action substantially equals the optimum level.

Certain aspects of the disclosure concern methods for reducing weight in a subject having a stomach. Such a method may comprise determining an optimum level of total stomach electrical activity, including either or both natural and non-natural electrical activity. Optionally, such a method may further comprise positioning an electrode, such as a stimulatory electrode, relative to the subject so that the electrode can generate non-naturally occurring stomach electrical activity. Optionally, such a method may also comprise positioning an electrical activity sensor relative to the subject so that the electrical activity sensor senses the level of stomach electrical activity, which may include either or both naturally and non-naturally occurring electrical activity. Optionally, the electrical activity sensor may be operatively connected to the electrode. Still further, such a method may comprise periodically detecting the level of total stomach electrical activity, which may include either or both naturally and non-naturally occurring electrical activity, with the electrical activity sensor. Optionally, such a method may further comprise periodically generating non-naturally occurring stomach electrical activity with the electrode when the detected level of total stomach electrical activity differs from the optimum level. Optionally, such a method may take place until the detected level of total stomach electrical activity substantially equals the optimum level.

Certain aspects of the disclosure concern methods of providing electrical field stimulation to a gastrointestinal organ. Such a method may comprise positioning a first electrode in a gastrointestinal organ and positioning a second electrode in the gastrointestinal organ. The electrodes may be stimulatory electrodes. Optionally, the electrodes may be spaced apart from one another. Optionally, the second electrode may be placed 1, 2, 3, 4, 5, 6, 7, 8, 9 or 10 mm or 20, 30, 40, 50, 60, 70, 80, 90 mm or 1, 2, 3, 4, 5, 6, 7, 8, 9 or 10 cm or some range therein from the first electrode. In certain cases, the second electrode may be preferably placed at least about two centimeters from the first electrode. Optionally, the method may further comprise electrically stimulating the gastrointestinal organ simultaneously through the first and the second stimulatory-electrodes, wherein one of the first and the second stimulatory electrodes has a positive polarity and wherein the other one of the first and the second stimulatory electrodes has a negative polarity, thereby providing electrical field stimulation to the gastrointestinal organ between the first and the second stimulatory electrodes.

Certain aspects of the disclosure concern methods of providing electrical potential gradient in a gastrointestinal organ. Such a method may comprise positioning a first electrode in a gastrointestinal organ; positioning a second stimulatory electrode in the gastrointestinal organ. The electrodes may be stimulatory electrodes. Optionally, such a method further comprises the second electrode being positioned at a distance from the first electrode. Optionally, the second electrode may be placed 1, 2, 3, 4, 5, 6, 7, 8, 9 or 10 mm or 20, 30, 40, 50, 60, 70, 80, 90 mm or 1, 2, 3, 4, 5, 6, 7, 8, 9 or 10 cm or some range therein from the first electrode. In certain cases, the second electrode may be preferably placed at least about two centimeters from the first electrode. Optionally the method further comprises electrically stimulating the gastrointestinal organ simultaneously through the first and the second stimulatory electrodes. Preferably in such a method, voltage generated by the first electrode differs from voltage generated by the second electrode. Such a method may result in the providing of an electrical potential gradient in the gastrointestinal organ between the first and the second electrodes.

Certain aspects of the disclosure provide methods of stimulating the vagus nerve of a subject. Such a method may comprise positioning a electrode in a gastrointestinal organ of a subject. The electrode may be a stimulatory electrode. Optionally, such a method further comprises generating electrical current in the gastrointestinal organ of the subject with the electrode. Such a method may result in stimulating the vagus nerve of a subject when the electrical current in the gastrointestinal organ stimulates the nerve.

Certain aspects of the disclosure provide methods of treatment for obesity comprising positioning a plurality of electrodes along the vagus neural pathway. Such a method may comprise positioning a first pair of bipolar stimulatory electrodes in contact with the gastric cavity along the afferent vagus neural pathway. Optionally, such a method further comprises positioning a second pair of bipolar stimulatory electrodes in contact with the intestinal cavity along the afferent vagus neural pathway. Still further, such a method may comprise administering electrical stimulation. Optionally, wherein the method comprises electrical stimulation, it may be effective at least in part, in activating the vagal afferents to modulate gastrointestinal peptide satiety hormones in the individual. Optionally, when the use of two pairs of electrodes is contemplated, such a method further comprises administering a phased pulse regimentation of the electrical stimulation which progresses from the first pair of electrodes to the second pair of electrodes. Optionally, the first pair of electrodes is positioned in contact with the distal antrum of greater curvature of the gastric cavity and the second pair of electrodes is positioned in contact with the duodenum. Optionally, such a method further comprises the placement of the electrodes. Such a method may comprise placement of the electrodes by laproscopic, endoscopic or surgical procedures, through the bore of a needle or some combination thereof. Such a method may further comprise electrical stimulation in repetitive pulse trains. Optionally, such a method further comprises the pulse trains having an operating frequency of 1 to 60 pulses/minute. Optionally, such a method further comprises one or more pulses or each pulse having a pulse width of about 10 milliseconds to about 1000 milliseconds. Optionally, such a method further comprises one or more pulses or each pulse having an amplitude of about 1 to about 15 mA. Optionally, such a method comprises the electrical stimulation having a train on-time of 2 s and off-time of 3 s. Optionally, such a method further comprises the administration of the electrical stimulation a single time or multiple times. Optionally, such a method further comprises administration of electrical stimulation preceding a meal, concurrent with a meal, following a meal or some combination thereof.

Certain aspects of the disclosure concern methods for treating a subject for an eating disorder wherein the eating disorder is selected from the group consisting of obesity, compulsive eating and bulimia. Such a method may comprise positioning a first pair of bipolar stimulatory electrodes in contact with the gastric cavity. Optionally, such a method may further comprise positioning a second pair of bipolar stimulatory electrodes in contact with the intestinal cavity. Optionally such a method may comprise administering electrical stimulation. Optionally, in such a method the electrical stimulation is effective, at least in part, in activating vagal afferents to modulate gastrointestinal peptide satiety hormones in the individual. Optionally the gastrointestinal peptide satiety hormones are hormones selected from the group consisting of consisting of ghrelin, obestatin, CCK-8 and PYY.

Certain aspects of the disclosure provide methods of placing a device in the gastrointestinal tract of a subject. Such a method may comprise placing the device from the exterior of the subject. Optionally, such a method further comprises inserting at least part of a needle, such as an end of a needle, from the exterior of a subject into the gastrointestinal tract of the subject. Optionally, such a method further comprises a needle having an interior bore. In such a method, the gastrointestinal tract of the subject may be considered to have center defined by a wall. The wall of the gastrointestinal tract may be considered to have a thickness defining an interior wall adjacent to the center and an exterior wall. The method may further comprise inserting a needle, such as a needle having an interior bore, through the wall of the gastrointestinal tract and into the center of the gastrointestinal tract. The method may further comprise inserting a device through the interior bore of the needle. Optionally, the method contemplates that they device may have an interior wall engaging means. As noted above, the interior wall may be considered the interior wall of the gastrointestinal tract. In methods wherein a needle with an interior bore and a device with an interior wall engaging means is contemplated, the method may further comprise inserting the device at least until the interior wall engaging means extends beyond the interior bore of the needle. Optionally, such a method further comprises removing the needle. Optionally, such a method further comprises retracting the device until the interior wall engaging means engages the interior wall of the gastrointestinal tract of the subject. Such a method may result in placing the device in the gastrointestinal tract of the subject.

Certain aspects of the disclosure provide methods of placing a device in the gastrointestinal wall of a subject. Such a method may comprise the placing of a device in the gastrointestinal wall of a subject from the exterior of the subject. Optionally, such a method further comprises inserting at least part of a needle, such as an end of a needle, from the exterior of a subject into the gastrointestinal tract of the subject. Optionally, such a method further comprises a needle having an interior bore. In such a method, the gastrointestinal tract of the subject may be considered to have center defined by a wall. The wall of the gastrointestinal tract may be considered to have a thickness defining an interior wall adjacent to the center and an exterior wall. The method may further comprise inserting a needle, such as a needle having an interior bore, into the wall of the gastrointestinal tract. Optionally, in such a method the needle may be inserted until the end of the needle is positioned in the thickness of the wall between the interior wall and the exterior wall. The method may further comprise inserting a device through the interior bore of the needle. Optionally, in such a method, the device may have an engaging means. Optionally, such a method further comprises inserting the device until the engaging means extends beyond the interior bore of the needle into the thickness of the wall. Optionally, such a method further comprises removing the needle. Optionally, such a method further comprises retracting the device. Optionally, such a method further comprises retracting the device until the engaging means engages the thickness of the wall. Such a method may thereby place the device in the gastrointestinal wall of the subject. Optionally the device may comprise an electrode, such as a stimulatory electrode. Optionally the device may comprise a sensor such as an electrical sensor. Optionally the device may comprise both an electrode and a sensor. Optionally, the device may comprise a plurality of electrodes. Optionally the device may comprise a plurality of sensors. Optionally the device may comprise a plurality of electrodes and one sensor. Optionally the device may comprise a plurality of sensors and one electrode. Optionally the device may comprise a plurality of electrodes and sensors.

Certain aspects of the disclosure provide methods of endoscopic placement or visualization of one or more electrode and/or sensor. Such a method can comprise using an endoscope for a variety of applications such as but not limited to: 1) visualization and insertion of electrodes and/or sensors with an endoscope 2) endoscopic visualization to guide insertion of the electrodes and/or sensors, 3) endoscopic insertion of electrodes and/or sensors wherein the observation of the placement is done with a colonoscope or laproscopically and 4) using a plurality of endoscopes for placement of electrodes or sensors (e.g. one endoscope to observe placement of an electrode and another endoscope to place the electrode and/or sensor). Optionally such a method may comprise the use of a single electrode and a single sensor or a plurality of electrodes and sensors or some combination thereof. Optionally, such methods further consist of a subject being sedated prior to or during the endoscopic visualization or placement of the electrode. Optionally, such methods further consist of inserting an endoscope or endoscopes in the gastrointestinal tract via the mouth. Optionally, in methods wherein observation of the placement of one or more electrode and/or sensor is contemplated, the methods may further comprise the insertion of a needle into the gastrointestinal tract from the exterior of the subject. Optionally, the methods further comprise a needle penetrating the gastrointestinal tract to the interior of the gastrointestinal tract or to the thickness of the wall of the gastrointestinal tract. In methods wherein a needle is contemplated, the needle may be a hollow needle with a hole in the middle such as a needle having an hollow interior bore. In other methods, a laproscope or trocar is contemplated to access the exterior of the gastrointestinal tract.

Certain aspects of the disclosure provide methods of colonoscopic placement or visualization of one or more electrode and/or sensor. Such a method can comprise using an colonoscope for a variety of applications such as but not limited to: 1) visualization and insertion of electrodes and/or sensors with a colonoscope 2) colonoscopic visualization to guide insertion of the electrodes and/or sensors, 3) colonoscopic insertion of electrodes and/or sensors wherein the observation of the placement is done with an endoscope or laproscopically and 4) using a plurality of colonoscopes for placement of electrodes or sensors (e.g. one colonoscope to observe placement of an electrode and another colonoscope to place the electrode and/or sensor). Optionally such a method may comprise the use of a single electrode and a single sensor or a plurality of electrodes and sensors or some combination thereof. Optionally, such methods further consist of a subject being sedated prior to or during the colonoscopic visualization or placement of the electrode. Optionally, such methods further consist of inserting a colonoscope or endoscopes in the gastrointestinal tract via the mouth. Optionally, in methods wherein observation of the placement of one or more electrode and/or sensor is contemplated, the methods may further comprise the insertion of a needle into the gastrointestinal tract from the exterior of the subject. Optionally, the methods further comprise a needle penetrating the gastrointestinal tract to the interior of the gastrointestinal tract or to the thickness of the wall of the gastrointestinal tract. In methods wherein a needle is contemplated, the needle may be a hollow needle with a hole in the middle such as a needle having an hollow interior bore. In other methods, a laproscope or trocar is contemplated to access the exterior of the gastrointestinal tract.

Certain aspects of the disclosure contemplate placement of a device endoscopically through the esophagus and into the stomach where it is implanted in the stomach wall. Optionally, the method comprises preparing an opening in the gastrointestinal tract from the interior of the stomach to access the wall of the gastrointestinal tract for implanting the device. Optionally, the method comprises creating a cavity in the wall of the gastrointestinal tract. Optionally, the method further comprises placing the device through the opening into the wall of the gastrointestinal tract. Optionally, the method further comprises closing the cavity. According to one variation, after preparing the opening in gastrointestinal tract, a pocket or cavity is prepared in the gastrointestinal tract to receive the device. Optionally, a knife, needle or cutting instrument may be used to prepare an opening in the wall of the gastrointestinal tract. Optionally, such a method further comprises injecting a material or solution into the opening for implanting the device, to form a bleb or blister in the gastrointestinal wall. Optionally, such a method may comprise the use of a tissue dissector to prepare a cavity. Optionally, the tissue dissector may be a blunt dissector, for example, a blunt tool, an expandable compliant or non-compliant balloon, or another mechanically expanding device, or a cutting blade. The dissector may also be a device using an energy source to break down or cut tissue such as an electrosurgical cutting or coagulating device, or an ultrasonic or laser device.

In certain aspects of the disclosure wherein placement of a device is contemplated, a device may comprise a Teflon™-insulated wire may be extended via the hole of the needle. Optionally the insulated wire may be peeled off at the distal portion. Optionally, the exposed or peeled off portion of the inserted Teflon™-insulated wire serves as an electrode. In methods where insertion of a needle is contemplated, the needle may be removed after the insertion of the wire. In methods where a wire is contemplated, the wire may further comprise an engaging means. The engaging means may allow for engagement of the wire with the interior wall of the gastrointestinal tract or the thickness of the wall of the gastrointestinal tract when the wire is pulled from the exterior. Such an engaging means may prevent the wire from being further pulled out of the interior of the gastrointestinal tract or the wall of the gastrointestinal tract.

In certain aspects of the disclosure wherein a device is contemplated, the device may comprise sensors for sensing various parameters of the gastrointestinal tract. Optionally, such a device may comprise sensors which may operatively connected to an electrical stimulator. Optionally, such a device may comprise a mechanical sensor that senses, for example, stomach wall contractions. Optionally, such a device may be implanted in the gastrointestinal wall. Optionally such a device may include a pressure sensor that is arranged to measure pressure change due to contractions of surrounding tissue. Alternatively, electrical sensors may detect changes in impedance due to changes in wall thickness from smooth muscle contractions. Other examples of such sensors may include, for example, pH sensors, impedance sensors, pressure sensors, strain gauges, and temperature measuring devices such as a thermocouple.

In certain aspects of the disclosure wherein a device is contemplated, the device may comprise one or more electrical stimulators for electrically stimulating various portions of the gastrointestinal tract. Optionally, such a device may comprise one or more electrical stimulators which may be programmed to deliver stimulation in response to sensing electrical parameters or other sensed parameters. Optionally, such a device may be user controlled, where the recipient of the device or treating practitioner is able to externally activate the device, for example by using an external unit which delivers a control signal via telemetry. Optionally, a temperature sensor may be used, for example, to determine when food has been ingested, by a change in temperature. Optionally, the device may begin stimulating the stomach upon detecting sudden change in temperature. Optionally, pressure sensors may be used to sense motility patterns, e.g. presence, strength or frequency of contractions. Optionally mean pressure shifts may be observed to identify fundal contractility. Optionally, the stimulation device may also use sensed parameters to program or reprogram the device stimulation program. For example, by measuring impedance changes through a circuit coupled to the electrodes (e.g., delivering a constant current or voltage across the electrodes to determine impedance) or determining the contractile behavior of the stomach using a strain gauge, in response to stimulation pulses, the effectiveness of the stimulation pulses may be monitored and adjusted to provide optimal response. Optionally, the stimulation program may also include an automatic adjustment in response to changes in pressure measurement.

In certain aspects of the disclosure, wherein the placement of an electrical stimulator is contemplated by the methods disclosed herein, the electrical stimulator may extend throughout the thickness of the wall of the gastrointestinal tract. For example, the electrical stimulator can be placed in the stomach of the gastrointestinal tract and can therefore be so placed as to extend throughout the thickness of the wall of the stomach.

Certain aspects of the disclosure contemplate the placement of a device into the wall or through the wall of the gastrointestinal tract. As will be apparent, the device may comprise an electrode or a sensor or a plurality of electrodes and sensors or a single electrode and a plurality of sensors or a plurality of electrodes and a single sensor.

In certain aspects of the disclosure wherein a device is contemplated, the device may comprise an engaging means wherein the engaging means itself comprises a plurality of radially extendable arms positioned at an axis perpendicular, acute or obtuse to the insertion axis of the stimulator or sensor. The stimulator or sensor is inserted until the axis of the plurality of radially extendable arms extends beyond the interior bore of the needle, at which point the arms radially extend. The electrical stimulator is retracted until the radially extended arms engage the interior wall of the gastrointestinal tract. Optionally, the device may have 2, 3, 4, 5, 6, 7, 8, 9 or 10 radially extendable arms or more. Optionally each radially extendable arm may be positioned to the same angle. Without being limited to the particular example, each radially extendable arm may be positioned perpendicular or 90° from the insertion axis or 120° from the insertion axis or some angle between about 1° and 178° from the insertion axis. Alternatively, each radially extendable arm may be positioned to different angles. Without being limited to the particular example, one radially extendable arm may be positioned at an angle of about 1° from the insertion axis, another radially extendable arm may be positioned at an angle of about 60° from the insertion axis, another radially extendable arm may be positioned at an angle of about 90° from the insertion axis and another radially extendable arm may be positioned at an angle of about 136° from the insertion axis. Optionally, the plurality of radially extendable arms may be in the same plane. Alternatively, one or more radially extendable arms may be in a different plane as compared to another arm or arms. Without being limited to the particular example, two radially extendable arms may be at the terminal end of the device comprising an insertion axis wherein the device is positioned with the terminal end towards the center of the gastrointestinal tract, while three radially extendable arms may be positioned some distance away, such as 2-20 mm from the terminal end of the device along the insertion axis.

In other aspects of the disclosure wherein a device is contemplated, the device may be made of a soft plastic polymer or other medically acceptable non irritating material. Optionally, the device may be compressible. Optionally, the device may further comprise a plurality of electrodes and/or sensors. Optionally the device may be fixed by suture to the gastrointestinal tract. Alternatively, the device may be held stationary with respect to the gastrointestinal tract by a locking mechanism which surrounds wires leading to the stimulators or sensors and may be placed on the exterior wall of the gastrointestinal tract or on the skin of a subject. An example of a device that may be fixed or locked can be found in U.S. Pat. No. 5,292,344.

Certain aspects of the disclosure provide a for a device comprised of biocompatible materials that allow it to remain in the environment of the gastrointestinal tract or within the gastrointestinal tract wall for the life of the device, e.g., several weeks, months or years. Optionally, the electrode(s) or sensor(s) may comprise corrosion resistant metals and alloys such as, e.g. platinum, iridium, gold, tantalum, titanium, stainless steel or alloys of one or more of these metals, e.g., a platinum/iridium alloy. Other non-conductive parts of the device may comprise inert polymers, for example, from the polyolefin family, e.g., HDPE (high density polyethylene), PP (polypropylene), UHMWPE (ultra high molecular weight polyethylene), or fluoropolymer such as PTFE (polytetrafluoroethylene) FEP (fluorinated ethylene propylene) and other members. PMP (polymethylpentene), polysulfone, PMMA (polymethylmethacrylate) may also be used. Softer materials may be used, such as, e.g., silicones, C-Flex, polyurethanes, co-polymer nylons (e.g. PEBAX).

In other aspects of the disclosure wherein a device is contemplated, the device may comprise one or more stimulators and/or electrodes. Optionally such a device may further comprise a first and second pair of attachment members that secure the device in the gastrointestinal tract wall. Optionally, the first attachment members of the device are the first to enter the gastrointestinal tract wall. In such a device the attachment members may comprise a flexible material. Optionally the attachment members may be considered tines. Optionally the first tines may be considered leading tines that define an obtuse angle with respect to travel of the insertion axis of the device. Optionally, the leading tines have a diameter of about 1 mm and a length of about 3 mm. Optionally the second tines may define an angle which is obtuse, perpendicular or acute with respect to travel of the insertion axis of the device. Optionally, wherein the second tines are at an obtuse angle with respect to travel of the insertion axis of the device, the second pair of tines may or may not penetrate the gastrointestinal tract wall. Alternatively, wherein the second tines are at an acute or perpendicular angle with respect to travel of the insertion axis of the device, the second pair of tines may not penetrate the gastrointestinal tract wall. Examples of a device of this type may be found in U.S. Pat. No. 6,542,776. Such a device may be inserted into the gastrointestinal tract through a trocar from the exterior of the subject. Alternatively, such a device may be inserted from the exterior of a subject through a needle with a hollow bore wherein the flexible tines are compressed to be at an obtuse angle during insertion through the needle and into the wall of the gastrointestinal tract but are uncompressed or less compressed when exiting the hollow bore of the needle. Optionally, wherein the second tines are also at an any angle relative to the insertion direction of the insertion axis of the device, they may be compressed inside of the hollow bore of a needle and uncompressed or less compressed when exiting the hollow bore of a needle.

In still other aspects of the disclosure wherein a device is contemplated, the device may be a device comprising stimulators and/or sensors and may be described in detail in U.S. Pat. No. 6,542,776. Such a device may comprise for example four electrodes which may be placed in contact with the interior or the exterior wall of the gastrointestinal tract. Optionally, such a device has electrodes supported by an electrode attachment member where the electrodes are in a plane with each other. One may envision four electrodes on a flat plate. Such an electrode attachment member may be attached to the gastrointestinal tract wall by sutures or staples. Optionally, the attachment member may have fixed tines at the point of placement of the attachment member to the wall of the gastrointestinal tract. Such fixed tines may be inserted into the wall of the gastrointestinal tract in lieu of or in addition to sutures or staples in order to place the electrode attachment member. Optionally, the electrode attachment member further comprises an insertion axis extending through the electrode attachment member with a plurality of radially spaced arms as described above to place the electrode attachment member. Optionally, the electrode attachment member may be inserted to the body cavity or through the hollow bore of a needle. Optionally, the electrode attachment member may be constructed from a flexible material such as, e.g., silicone elastomer or similar material. The base materials for the electrodes which may act as stimulators and/or sensors may be comprised of platinum, platinum-iridium alloys, titanium and the like. The electrodes may optionally be in an uncoated state or may be coated with materials such as iridium oxide or titanium nitride or the electrodes may be platinized or carbonized. Optionally, the electrode attachment member has a substantially circular configuration. Alternatively, the electrode attachment member may be in any suitable configuration such as for example, square, oval, rectangular, etc. Optionally, the electrodes may be distributed around the distal surface equidistantly from the center of the distal surface.

In certain aspects of the disclosure wherein a device is contemplated, the device may be that which is disclosed in U.S. Pat. No. 7,076,306 which is hereby incorporated by reference in its entirety. In certain aspects of the disclosure wherein a device is contemplated, the device may be a distributed microsystem setup in which an implanted microsystem is sutured or otherwise attached to the wall of the gastrointestinal tract. Such a device may be found in U.S. Pat. No. 7,720,539 which is hereby incorporated by reference. Optionally, such a device may incorporate a screw mechanism which may screw into the wall of the gastrointestinal tract. Such a device may be found in U.S. Pat. No. 7,711,437 which is hereby incorporated by reference. In certain aspects of the disclosure wherein a device is contemplated, the device may include an expandable member that fixes electrodes in contact with the gastrointestinal tract wall. Optionally such a device is radially expandable. Optionally such a device may be able to expand radially when passed through the hollow bore of a needle. Optionally such a device may be inserted into the thickness of the wall of the gastrointestinal tract. Such a device may be found in U.S. Pat. No. 7,676,270 which is hereby incorporated by reference. Other examples of electrical stimulation devices that may be used according to the present disclosure are found in U.S. Pat. Nos. 7,599,736, 7,477,994, 7,363,084, 7,310,557, 7,203,551, 7,177,693 and 7,016,735 which are hereby incorporated by reference. Other examples can be found in U.S. Pat. Pub. Nos. 20070049793 and 20050251219 which are hereby incorporated by reference.

In certain aspects of the disclosure wherein a plurality of radially extendable arms is contemplated, the arms may be affixed to the insertion axis of the device. Optionally, arms may be affixed via a hinge mechanism. Optionally, the arms may be affixed via flexible resilient wires to the insertion axis.

In certain aspects of the disclosure wherein placement of a device is contemplated, the methods may comprise a gastrointestinal wall tunneling instrument. Optionally, such an instrument may further comprise an elongate tubular member having proximal and distal ends and a lumen extending therethrough and an elongate expandable member located at the distal end of the tubular member. The expandable member may have proximal and distal ends wherein the proximal end of the expandable member is connected to the distal end of the tubular member. The expandable member may be everted, such that the distal end of the expandable member is positioned within the lumen of the tubular member. An example of this type of method and instrument can be found in PCT/US2008/067642 and is herein incorporated by reference.

Figure 21:
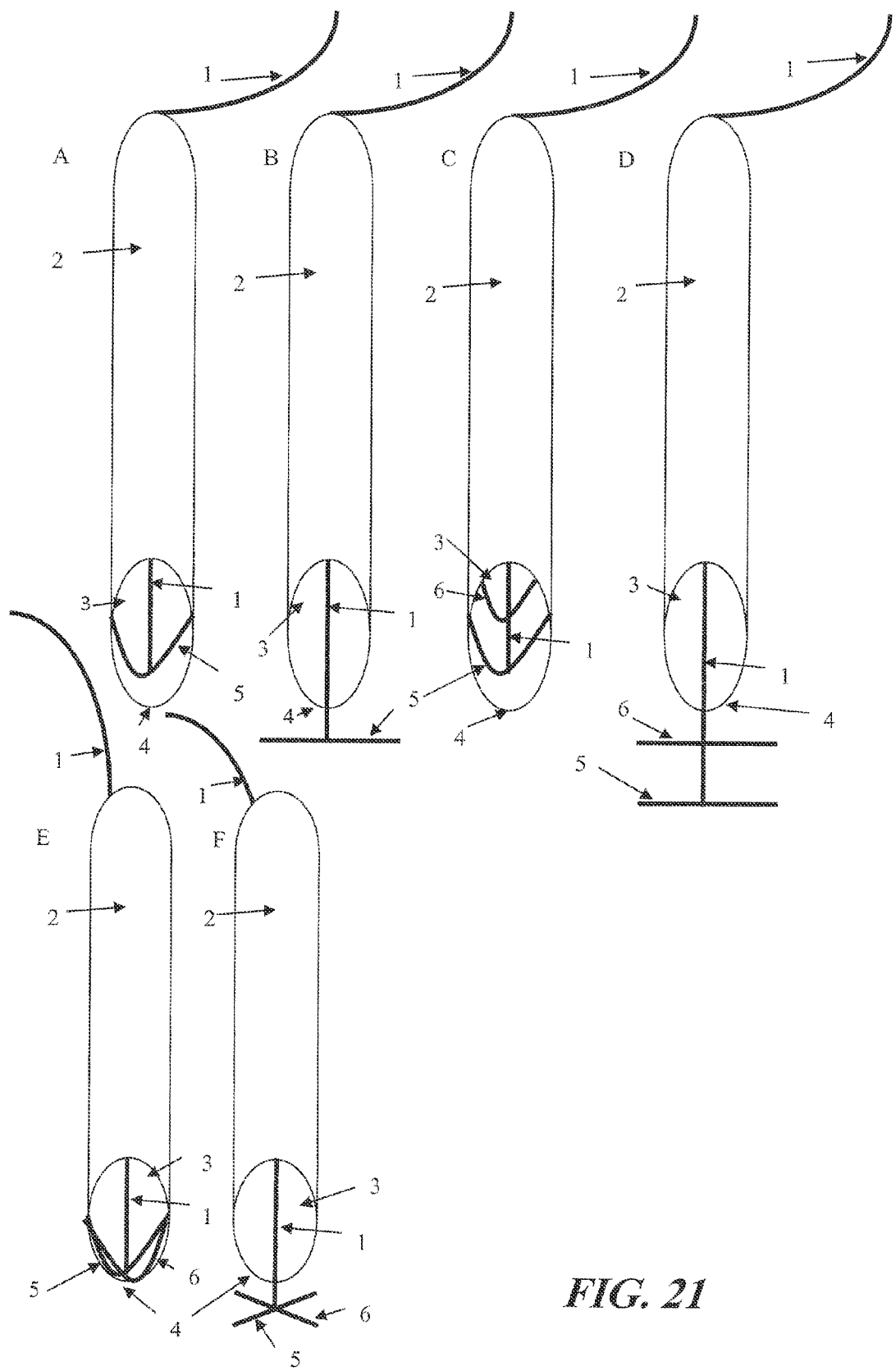

Certain aspects of the disclosure may pertain to a method of placing a device and an implantable device as demonstrated in FIG. 21. Referring to FIG. 21A, an electrode lead with an insertion axis 1 is inserted into a needle 2 with a hollow bore 3. The needle has an entrance tip 4 which may be inserted through the skin and into or through the wall of the gastrointestinal tract. The electrode lead 1 may have a first or a single pair of radially spaced arms 5. Optionally, such arms 5 are in an angular position which is more acute than when passed through the needle as shown in FIG. 21A. Referring to FIG. 21B the radially spaced arms 5 are in an angular position which is less acute than or perpendicular to the electrode lead with an insertion axis 1 when passed through the needle. Referring to FIG. 21C the lead 1 may have a second or additional pair of radially spaced arms 6 at a distance from the first pair of radially spaced arms 5. Referring to FIG. 21C, each pair of radially spaced arms 5 and 6 may be retracted to an angle more acute than when passed through the needle 2. Referring to FIG. 21D, the first pair of radially spaced arms 5 and the second or additional pair of radially spaced arms 6 may be in an angular position which is less acute or perpendicular when passed through the hollow bore 3 of the needle 2. Optionally, referring to FIG. 21E the lead 1 may have a second or additional pair of radially spaced arms 6 in the same plane from the first pair of radially spaced arms 5. Referring to FIG. 21E, each pair of radially spaced arms 5 and 6 may be retracted to an angle more acute than when passed through the needle 2. Referring to FIG. 21F, the first pair of radially spaced arms 5 and the second or additional pair of radially spaced arms 6 may be in an angular position which is less acute or perpendicular when passed through the hollow bore 3 of the needle 2. It is also contemplated that a lead 1 may have a plurality of radially spaced arms in an odd numbered configuration, such as for example three arms instead of the first or single pair of radially spaced arms 5 or the second or additional pair of radially spaced arms as referenced throughout FIG. 21.

Certain aspects of the disclosure concern placement of a device as shown in FIGS. 22A and B. Referring first to FIGS. 21A and 21B, an electrode lead with an insertion axis 1 and radially spaced arms 5 may be inserted through a needle 2 comprising a hollow bore 3 wherein the entrance tip of the needle 4 may be inserted through the skin and into or through the gastrointestinal wall which may alternatively be considered the wall of the gastrointestinal tract. Referring to FIG. 22A, the needle 2 with the hollow bore 3 is removed after insertion of the electrode lead with an insertion axis 1 comprising radially spaced arms 5 such that the lead extends through the skin 8, the panniculus 9 and into the gastrointestinal wall 10. Alternatively, referring to FIG. 22B, the lead extends through the skin 8, the panniculus 9 and through the gastrointestinal wall 10.

Figure 23:
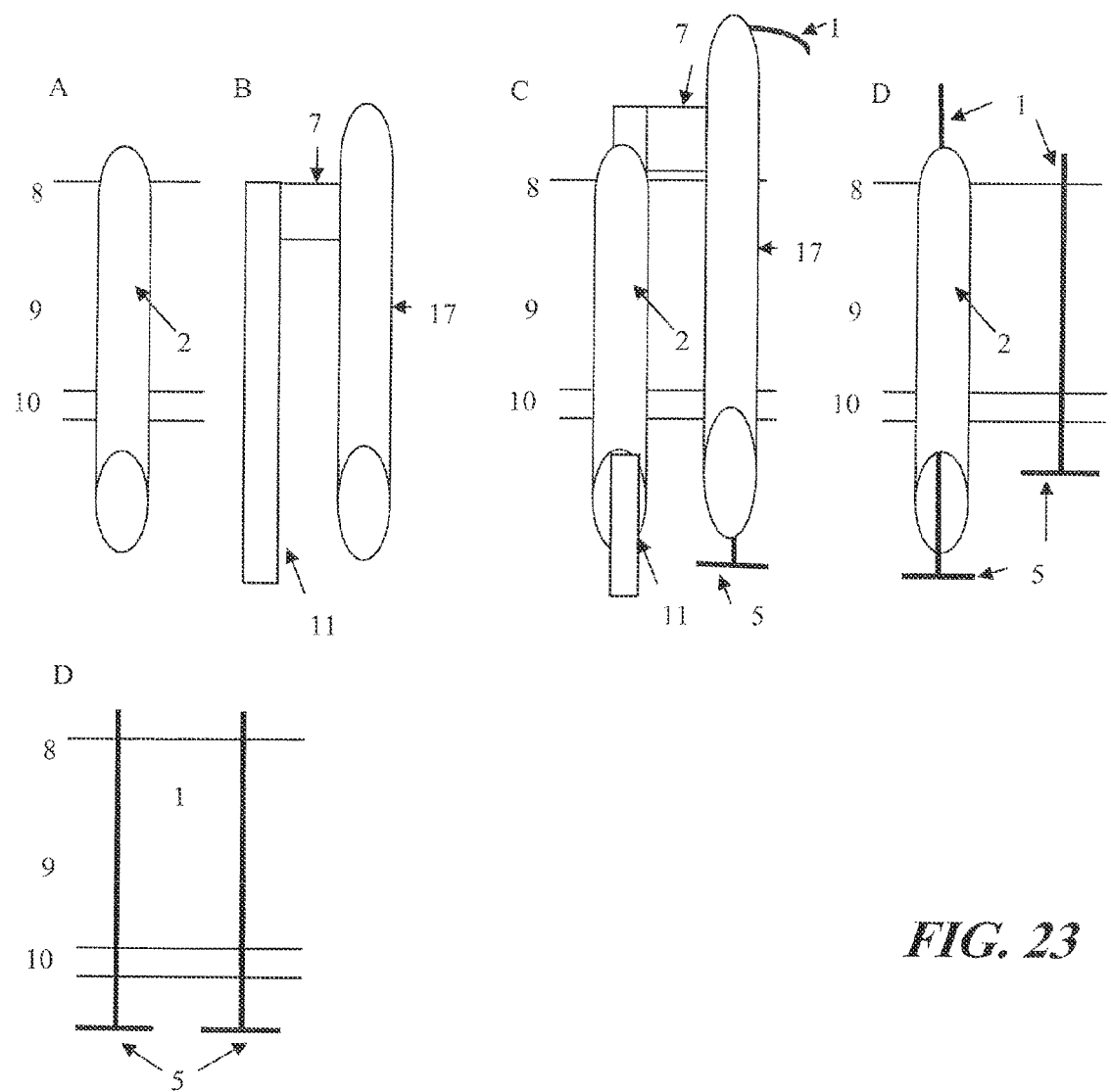

Certain aspects of the disclosure pertain to optimal spacing of a plurality of electrodes in the wall of the gastrointestinal tract or through the gastrointestinal tract. Referring to FIG. 22C a plurality of needles 2 may be connected via a bridge 7 such that a plurality of electrode leads with insertion axis 1 comprising radially spaced arms 5 are spaced an optimal distance from each other. The bridge may be any length that achieves optimal spacing. Optionally, the bridge 7 may allow separation of the needles 2 by a distance of 1, 2, 3, 4, 5, 6, 7, 8, 9 or 10 mm or 1, 2, 3, 4, 5, 6, 7, 8, 9 or 10 cm or some distance therein. Alternatively, referring to FIG. 23A, a needle 2 may first be inserted through the skin 9, the panniculus 9 and either into or through the gastrointestinal wall 10. A second needle 17 as shown in FIG. 23B may include a bridge 7 connected to a guide rod 11. Referring to FIG. 23C, the guide rod 11 may be inserted into the needle 2 and an electrode lead with an insertion axis 1 comprising radially spaced arms 5 may be inserted into the second needle. The guide rod 11 is inserted through the first needle 2 as the second needle is inserted through the skin 8, the panniculus 9 and into or through the gastrointestinal wall 10. Referring to FIG. 23C, the second needle 17 may be removed leaving in place an electrode lead with an insertion axis 1 comprising radially spaced arms 5 which may be located in the gastrointestinal tract or in the gastrointestinal wall 10. Also referring to FIG. 23C, a second gastrointestinal lead with an insertion axis 1 and a plurality of radially spaced arms 5 may now be inserted in the first needle where the guide rod was previously located. Referring to FIG. 23D, the first needle may be removed so that there is more than one electrode lead with an insertion axis 1 and a plurality of radially spaced arms 5 extending through the skin 8, the panniculus 9 and into or through the gastrointestinal wall 10.

Optionally, in certain aspects of the disclosure where placing of a device is concerned, the device may be a percutaneous endoscopic gastronomy type device. Referring to FIG. 24A, the device may comprise a skin bolster 12 attached or abutting the skin 8 and a gastric bolster 13 attached to or abutting the inside of the gastrointestinal wall 10. A plurality of electric leads 14 may be inserted through the skin bolster 12, through the panniculus 9 and through the gastrointestinal tract wall. The electric leads may be insulated and the lead ends 15 exposed and used as electrodes.

In certain aspects of the disclosure wherein an electrode lead with an insertion axis 1 comprising a plurality of radially spaced arms 5, the lead 1 and the arms 5 may be insulating a conductive wire 16 to serve as an electrode. Referring to FIG. 24B, an electrode lead with an insertion axis 1 comprising a plurality of radially spaced arms 5 which has been inserted through a needle 2 may have a conductive wire to serve as an electrode 16.

Certain aspects of the disclosure concern various means for maintaining the electrodes in position. Such other may include for example, anchors, sutures, anti-rotation mechanisms and device shape design.

In certain aspects of the disclosure wherein a device is concerned, the device may be constructed of a size and shape such that it can be deployed through the mouth and esophagus with the aid of an endoscope. Optionally, the stimulator is of a generally small profile when delivered to the implant site.

Still further, the implant be constructed and/or implanted so that the device predictably maintains electrical contact with a muscle layer of the gastrointestinal tract wall. Optionally, the device may be constructed of a configuration or shape that prevents device rotation, or may be constructed so that device rotation or movement does not interfere with the electrode/muscle layer contact. Such a device may be found in PCT/US2002/013771 which is hereby incorporated by reference.

In certain aspects of the disclosure wherein placing a device is concerned, such methods may include a means for maintaining the device in proper orientation so that the electrodes, sensors or other transducers on the device maintain contact with a preferred area or layer of the gastrointestinal tract wall, for example, so that the electrodes, sensors or other transducers are preferentially facing a desired wall of the gastrointestinal tract within a submucosal space. An anti-rotation means may be provided that prevents rotation of the implant around axes that would move electrodes, sensors or transducers away from intimate contact with a desired area of the gastrointestinal wall, such as, e.g., a muscle layer or mucosal layer.

In certain aspects of the disclosure wherein placing a device is concerned, the shape of the device may, for example, have a broad aspect when viewing that side of the device intended to be in contact with a particular layer of the gastrointestinal tract wall (e.g., a muscle layer or mucosal layer); i.e., the top-view of the device has relatively large length and width dimensions with respect to the height dimension of the device given by its side-views. Optionally, the aspect ratio of the device, defined as the width of a side-view divided by the height of the device is larger than about 1, preferably larger than about 1.4 and more preferably larger than about 1.8.

In certain aspects of the disclosure wherein placing a device is concerned, an anti-rotation means may be provided that prevents rotation of the device about an axis parallel to an intended tissue plane of contact. A device in one variation is dimensioned so that the aspect ratio of the device viewed along an axis parallel to the intended plane of contact is greater than one and preferably greater than 1.4 and more preferably greater than 1.8.

The aspect ratio as used herein may be the width to height ratio of the aspect viewed along a particular axis. Alternatively, the anti-rotation device may comprise an extendible or expandable portion or member that extends into a position that prevents rotation of the electrodes away from contact with the muscle layer of the gastrointestinal tract wall.

In certain aspects of the disclosure wherein placing a device is concerned, an anti-rotation means may be provided that prevents rotation of the device about an axis parallel to a common plane on which the electrodes may lie. Accordingly, a device may be dimensioned so that the aspect ratio of the device viewed along an axis parallel to plane on which the electrodes may lie is greater than one and preferably greater than 1.4 and more preferably greater than 1.8. The device in this instance may be defined by a plane on which the electrodes lie.

In certain aspects of the disclosure wherein placing a device is concerned, the device may have a relatively small profile when placed through the wall or into the wall of the gastrointestinal tract and may be altered to have a different shape when implanted, to prevent rotation and/or provide optimal sensor/transducer/electrode contact with the gastrointestinal tract wall.

In certain aspects of the disclosure wherein the device is contemplated, the device may be designed to promote encapsulation or tissue ingrowth, e.g. by choice of material, coatings or surface texture. Optionally an electrode(s) or sensor(s) or surrounding area may be coated with a material such as P-15, which is a commercially available compound that promotes cellular adhesion and tissue ingrowth.

In certain aspects of the disclosure wherein the device is contemplated, the device or portions of the device may be constructed of or coated with substances that inhibit tissue ingrowth.

In certain aspects of the disclosure wherein electrical stimulation is contemplated, an electrical stimulation may refer to an electrical signal, which includes train of pulses, and repetitive pulses. A train of pulses may refer to a method in which the stimulus is composed of repetitive trains of short pulses derived from a combination of two signals, a) a continuous short pulse with high frequency (in the order of 5 to 150 Hz), and b) control signal to turn the pulses on or off, such as "X" seconds on and "Y" seconds off. The addition of "X" and "Y" then determines the frequency of the pulse train. A frequency approximately equal to the physiologic frequency of stimulation may be performed using trains of pulses. The train may be set with a train on time from 0.1 s to 10 s, train off time from 0 s to 10 s, and pulses in each train with amplitude of 0.1 mA to 2 OmA (or voltage equivalent), width of 0.1 ms to 20 ms and frequency of 0.1 Hz to 200 Hz. The electrical stimulation may comprise repetitive long train of pulses with a width of 5 ms to 2000 ms, amplitude of 0.1 mA to 2 OmA and frequency of 1 pulse/min to 60 pulses/min. Methods of providing electrical field stimulation to a gastrointestinal organ are disclosed in PCT/US2000/028128 (GASTROINTESTINAL ELECTRICAL STIMULATION) which is hereby incorporated by reference herein. A discussion of pulse-train electrical stimulation is provided in Zhang et al., Current treatments of Gastroenterol. 9: 351-360 (2006), which is hereby incorporated by reference herein.

EXAMPLES

The following examples are included to demonstrate preferred embodiments of the disclosure. It should be appreciated by those of skill in the art that the techniques disclosed in the examples which follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit or scope of the disclosure. The following Examples are offered by way of illustration and not by way of limitation.

Materials and Methods

Preparation of Dogs—Healthy female (males are excluded since they would wet the jacket during urination) hound-dogs are used in this study. The dog is chosen to be the model for this study because: 1) the patterns of gastric myoelectrical activity and motility in dogs are the same as those in humans; and 2) the canine model has been used for the investigation of gastrointestinal motility for many years, and experimental results indicated that this animal model is ideal for motility studies.

After an overnight fast, the dog is operated upon under anesthesia. Approximately thirty minutes prior to induction of anesthesia, the dog is pre-medicated with acepromazine maleate (2 ml subcutaneously) and atropine (1 mg subcutaneously). Anesthesia is induced with thiamylal sodium (30 ml/kg, intravenously). Following induction of anesthesia and endotracheal incubation, anesthesia is maintained for surgery using 1.5 to 2.0% isoflurane in oxygen-nitrous oxide (1:1) carrier gases delivered from a ventilator (15 breaths/min with a titred volume of about 15 ml/kg). The animal is monitored with the assessment of tissue color and pulse rate. Four pairs of bipolar recording electrodes (cardiac pacing wires) are implanted on the serosal surface of the stomach along the greater curvature at an interval of 4 cm (see FIG. 16). The most distal pair is 2 cm above the pylorus. The distance between the two electrodes in a pair is 0.5 cm. Teflon-insulated wires are brought out through the abdominal wall subcutaneously and placed under a sterilized dressing until needed for recording and stimulation studies. Three strain gauges are placed, one in the fundus, one in the proximal antrum, and the other in the distal antrum, for the measurement of fundic tone and antral contractions. The wires of these strain gauges are brought out the same way as the electrodes. An intestinal fistula is made in the duodenal (20 cm beyond the pylorus). The fistula is used for the assessment of gastric emptying of liquids.

Following completion of surgery, the anesthetic gases are discontinued, and ventilation is continued with oxygen until the dog regains airway reflexes and is extubated. After extubation, the dog receives medications for post operative pain control and is transferred to a recovery cage. All studies are initiated about ten days after surgery when the dogs have completely recovered. A dog jacket and protective plastic collar are worn all the time to protect the wires and cannula from being chewed out by the dog.

Measurement and Analysis of Gastric Slow Waves The gastric slow wave are measured from the implanted serosal electrodes using a multi-channel recorder (Acknowledge, Biopac Systems, Inc., Santa Barbara, Calif.). All signals are displayed on a computer monitor and saved on the hard disk by an IBM-compatible 486 PC. The low and high cutoff frequencies of the amplifier are set at 0.05 Hz and 10 Hz respectively. The data is sampled at 20 Hz. For the spectral analysis of the slow waves, all data is further lowpass filtered with a cutoff frequency of 1 Hz (Qian et al., 1999; Abo et al., 2000).

Percentage of Normal Slow Waves The percentage of normal slow waves is defined as the percent of time during which regular slow waves (3.5-7.0 cpm) are detected from the time-frequency analysis of the slow wave measurement. This parameter reflects the regularity of gastric slow waves and is computed using the time-frequency analysis method discussed below (see also Chen et al., 1993). In the outcome-based feedback-controlled RGES system, this parameter is on-line computed and used to control the strength of stimulation.

Percentage of Slow Wave Coupling This parameter represents the coordination or coupling of gastric slow waves measured from different regions of the stomach. It is defined as the percentage of time during which the recorded slow waves in different regions are coupled. A cross-spectral analysis method is used to calculate the percentage of slow wave coupling among the different channels. First time-frequency analysis is performed on each channel minute by minute and the frequency of each minute of the slow wave in each channel is determined. Secondly, the frequencies of the slow waves between any two channels are compared. The minute of the slow waves recorded on the two channels is defined as coupled if their dominant frequencies are both within the normal frequency range and their difference is <0.2 cpm.

Figure 16:
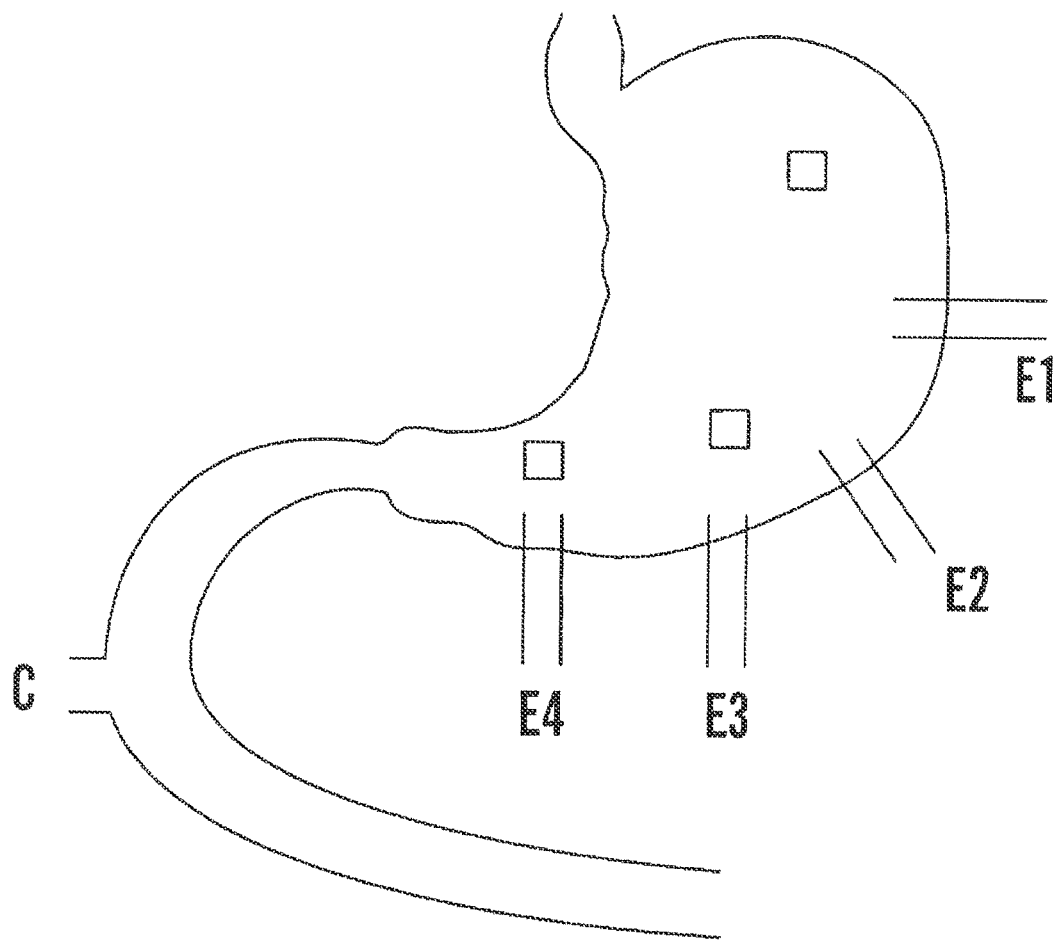
FIG. 16 illustrates the connection of electrodes to a dog stomach.

Measurement and Analysis of Gastric Contractions Gastric contractions in the fundus, proximal antrum and distal antrum are measured using the surgically implanted strain gauges as shown in FIG. 16. The recordings are made using the same multi-channel recorder used for the electrical recordings. Computerized software computes the frequency of contractions and the strength of contractions (area under the curve of each identified contraction).

Measurement and analysis of vagal activity. Regular electrocardiogram (ECG) is recorded using abdominal surface electrodes. R-R intervals are derived from the ECG using a method of fuzzy neural network. A signal, called heart rate variability (HRV), is derived after interpolation and sampling. Smoothed power spectral analysis is then performed on the HRV signal. Two parameters are computed from the power spectrum: LF (area under the curve in the low frequency band (0.04-0.15 Hz)) and HF (area under the curve in the high frequency band (0.15-0.50 Hz)). It is well established that the LF reflects mainly sympathetic activity and partial vagal activity, where the HF represents purely vagal activity (Lu et al., 1999). In addition, the ratio, LF/HF, represents sympatho-vagal balance.

Measurement of "Symptoms" in Dogs The symptoms of the dog during the experiment to be evaluated include salivation, licking tongue, murmuring (whine, growl, bark, yelp), and moving due to discomfort, and are scored by their severity and/or frequency. The severity is classified into 4 degrees, none (0), mild (1), moderate (2), and severe (3). For salivation, none is 0, seen around mouth is 1, sometimes drop is 2, and continuously drop is 3. For licking tongue and murmuring, none is 0, seldom/seen for <25% time of study is 1, often/seen for <50% time of study is 2, and severe/seen for >50% time of study is 4. For movement due to discomfort, none/same as baseline is 0, mild/seen but no need to soothe is 1, moderate/seen and need to soothe is 2, and severe/dog jumps, or moves constantly to interrupt study is 3. Vomiting is noted separately and scored as 4. A total symptom score is calculated.

Example 1

Antegrade Electrical Stimulation

Extensive experiments on antegrade gastric and intestinal electrical stimulation have been performed in both animals and humans. Unlike the retrograde stimulation proposed in this application, these studies were designed to normalize impaired gastrointestinal motility. The most important points learned from these experiments are: 1) electrical stimulation is able to entrain slow waves; 2) antegrade stimulation accelerates gastric emptying; and 3) no adverse effects have been noted in these previous studies, demonstrating safety of electrical stimulation.

Antegrade electrical stimulation entrains slow waves. A number of recent systematic studies have been performed and indicated that a complete entrainment of gastric slow waves is feasible in both humans and dogs (Lin et al., 1998; Lin et al., 2000a; McCallum et al., 1998; Qian et al., 1999; Abo et al., 2000; Lin et al., 2000b). The pulse width used for the entrainment of gastric slow waves in patients with gastroparesis was about 300 ms. However, complete entrainment is limited to a pacing frequency of slightly higher than the intrinsic frequency of the gastric slow wave. The entrainment was 100% when the pacing frequency was 10% higher than the intrinsic frequency and dropped to about 70% when the pacing frequency was 30% higher. In addition, the maximal driven frequency was about 4.3 cpm in patients with gastroparesis (Lin et al., 1998).

Figure 4A:
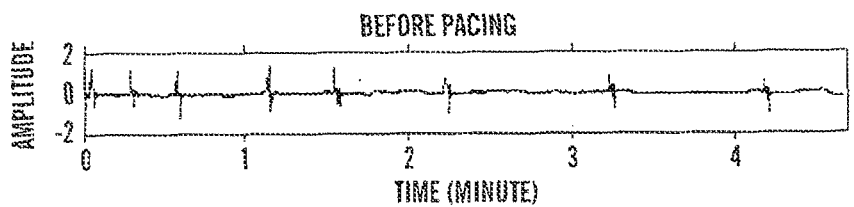
FIGS. 4A-4C illustrate normalization of bradygastria using gastric electrical stimulation.
Figure 4B:
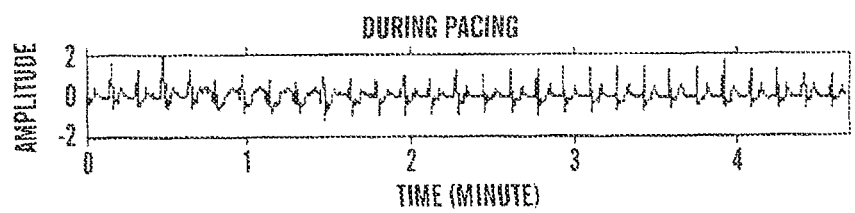
Figure 4C:
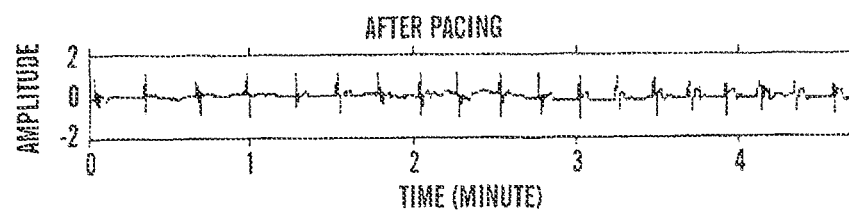

Antegrade electrical stimulation normalizes dysrhythmia. Entrainment of gastric slow waves using electrical stimulation with long pulses (in the order of milliseconds) makes it possible for the normalization of gastric dysrhythmia. Recent canine studies have also shown that gastric electrical stimulation was able to normalize gastric dysrhythmia induced by various pharmacological agents, such as vasopressin, glucagon and atropine (Qian et al., 1999). FIGS. 4A-4C show a typical example of impaired gastric slow waves (bradygastria, FIG. 4A) induced by atropine and normalized slow waves after gastric pacing (FIG. 4C).

In addition to gastric entrainment, it has also been shown that intestinal slow waves can be entrained using intestinal pacing with long pulses (Lin et al., 2000a; Lin et al., 2000b).

Figure 5:
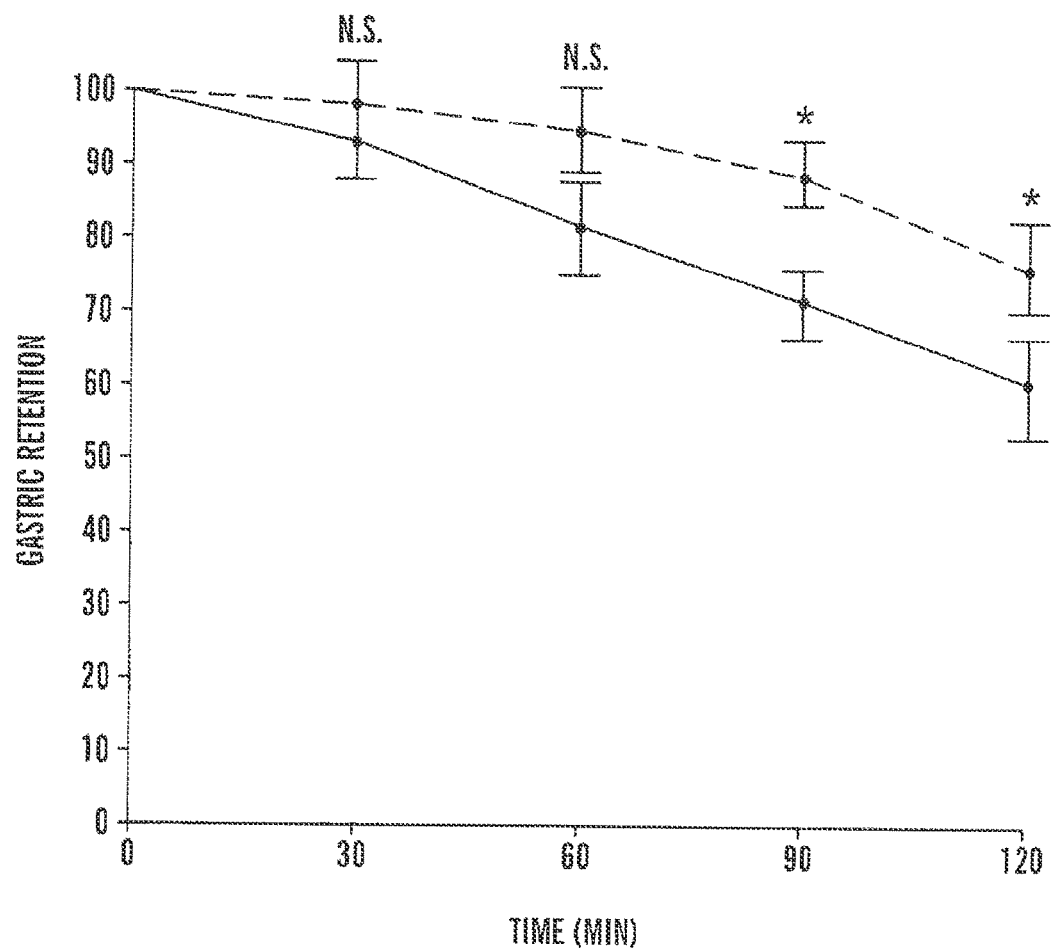
FIG. 5 illustrates the effect of gastric pacing on retention of a radionuclide solid meal.

Antegrade electrical stimulation accelerates gastric emptying in patients with gastroparesis. The effect of electrical stimulation on gastric emptying and symptoms in patients with severe gastroparesis has been investigated (McCallum et al., 1998). Electrical stimulation was performed via serosal electrodes implanted on the proximal stomach. A portable external pacemaker was built and used for stimulation for one month or more in each patient. A significant improvement was observed in both gastric emptying (FIG. 5) and symptoms of nausea, vomiting, bloating and etc.

Gastrointestinal electrical stimulation does not induce any adverse events. The above study not only suggested the therapeutic potential of antegrade gastric electrical stimulation for gastroparesis but also demonstrated the safety of gastric electrical stimulation in humans. No side effects or adverse events were noted in this clinical study. Chen and his colleagues have performed gastrointestinal electrical stimulation in more than 15 patients with gastroparesis and more than 30 dogs over the course of 7 years (Lin et al., 1998; Lin et al., 2000a; McCallum et al., 1998; Qian et al., 1999; Abo et al., 2000; Lin et al., 2000b). No adverse events have been observed in the patients. Some of the patients were studied for more than 4 months. Similarly, no gastrointestinal symptoms, such as vomiting or diarrhea, or other symptoms have been observed in dogs. Autopsy was performed in every dog that was sacrificed at the end of the study. No scars or muscle damage were noted in the gastric or intestinal area where stimulation electrodes were sutured. Some of the dogs have been studied for a period of 6 months or more.

Example 2

Retrograde Electrical Stimulation (RGES) for Treatment of Obesity and Other Gastrointestinal Tract Disorders This example places an artificial ectopic pacemaker in the distal antrum to partially or completely override regular gastric slow waves with a feedback control mechanism. Two pairs of bipolar electrodes are placed on the serosa along the greater curvature laparoscopically. The distal pair is about 2 cm above the pylorus and is used for electrical stimulation (serving as an artificial pacemaker), whereas the proximal pair is about 10 cm above the pylorus and is used for the measurement of gastric slow waves. The regularity of gastric slow waves is calculated from the proximal pair and the strength of electrical stimulation applied on the distal pair is determined based on the regularity of gastric slow waves measured from the proximal pair. The targeting regularity is set up in the initial trial period such that the intake of food is reduced but the subject is free of any symptoms other than early satiety. Once this value is determined, the value is used to automatically control the strength of electrical stimulation.

Figure 2:
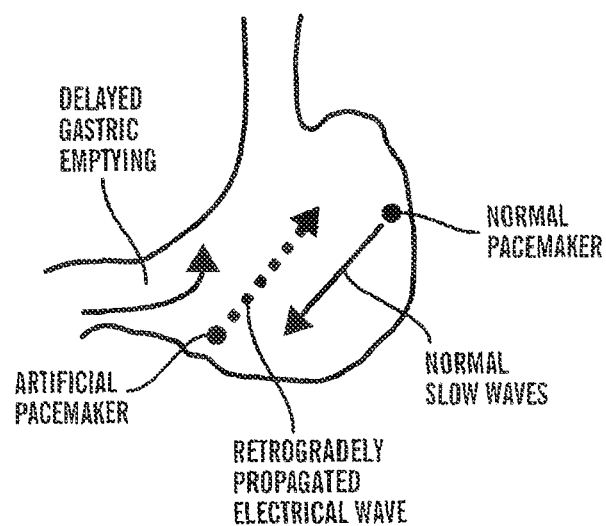
FIG. 2 illustrates the retrograde electrical stimulation (RGES) of the stomach to retard the propulsive activity of the stomach and slow down gastric emptying.

The principle of RGES is the opposite of what has been described for patients with impaired gastric emptying. RGES employs retrograde pacing with the aim of retarding the propulsive activity of the stomach and slowing down gastric emptying (FIG. 2). By slowing down gastric emptying of ingested food from the stomach, a sense of feeling full (satiety) results, leading to a reduction in food intake and subsequent weight loss.

Figure 3:
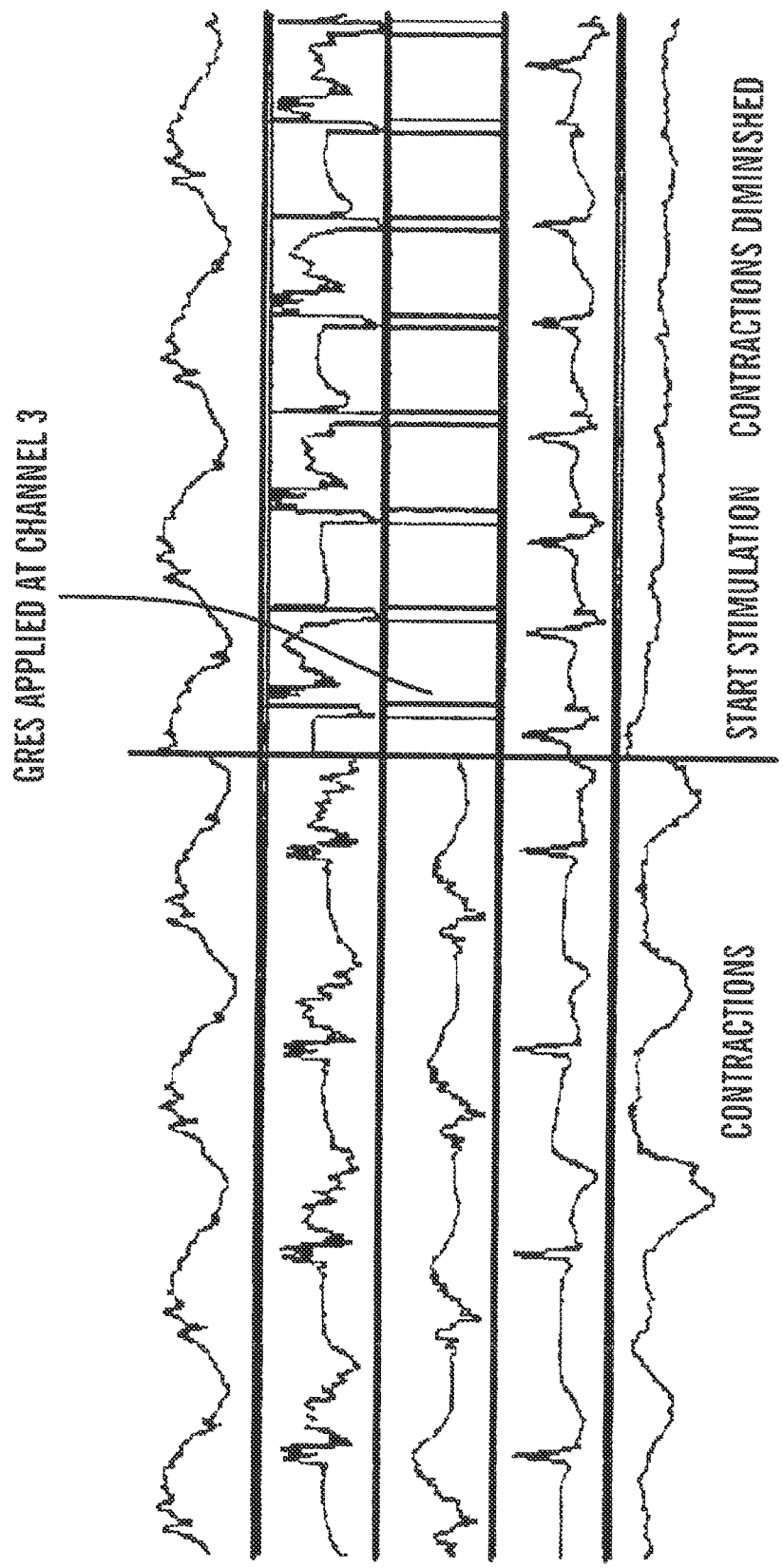
FIG. 3 illustrates the effects of RGES at a tacygastrial frequency on gastric slow waves and contractions in a healthy dog.

The rationale behind RGES at a tachygastrial frequency is to electrically induce tachygastria in the distal stomach, in effect producing an artificial ectopic pacemaker. This artificial pacemaker has two functions: 1) it interrupts the normal distal propagation of regular slow waves; and 2) it paces the gastric slow waves in the distal stomach at a tachygastrial rhythm. Both of these effects result in an absence of contractions in the distal stomach (see FIG. 3) and cause delayed gastric emptying. This results in increased satiety and decreased food intake. This method allows adjustment of the strength of electrical stimulus, and hence the degree of impairment in the gastric slow wave and its propagation. Thus, with proper settings, the amount of food intake can be finely tuned.

RGES at a "physiological" frequency reduces food intake. A study was performed to investigate the effects of RGES on gastric emptying and food intake. The study was performed in 10 healthy dogs with chronically implanted 4 pairs of serosal electrodes along the greater curvature: the 3 proximal pairs recorded gastric slow waves and the most distal pair (2 cm above the pylorus) provided retrograde stimulation. Each dog was studied in 3 sessions, without electrical stimulation (session 1), with strong retrograde stimulation to induce vomiting or noticeable symptoms (session 2) and with mild retrograde stimulation that does not induce vomiting or clearly noticeable discomfort (session 3). Electrical stimulation was performed at a frequency 10% higher than the intrinsic frequency of gastric slow waves measured at baseline. The dogs were given unlimited access of food during the study. All observable symptoms were noted and graded.

Figure 6:
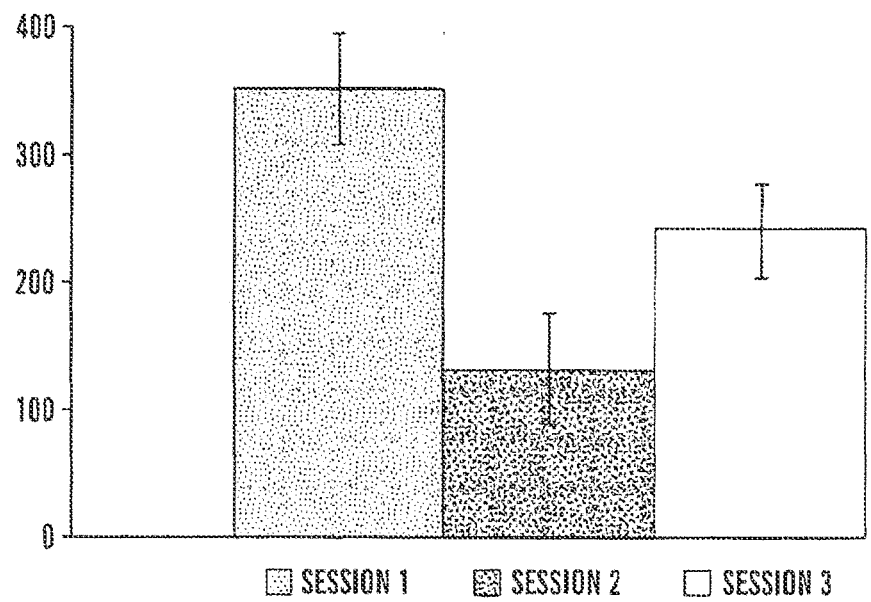
FIG. 6 illustrates food intake in separate sessions with varying amounts of electrical stimulation.
Figure 7:
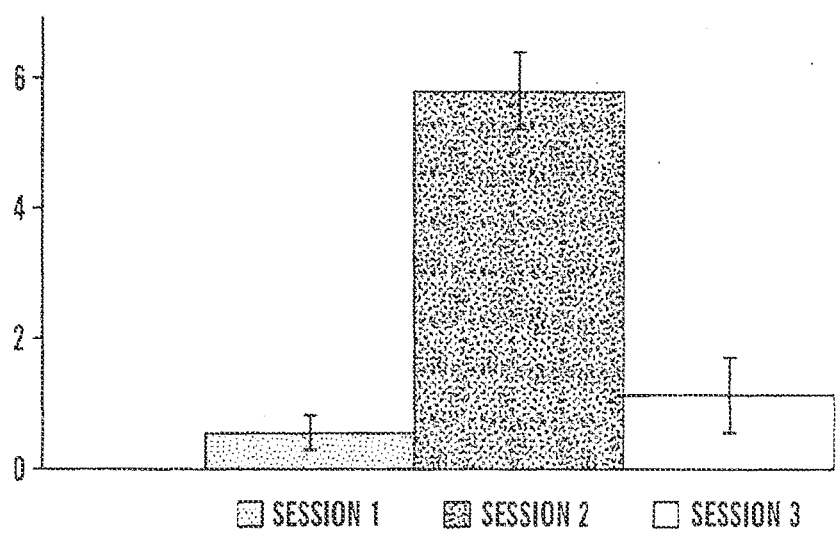
FIG. 7 illustrates symptoms seen in the separate sessions of FIG. 6.

RGES resulted in a significant reduction in food intake (FIG. 6). With strong retrograde stimulation (session 2), eight dogs vomited and all dogs showed various symptoms (see Materials and Methods). On the other hand, with mild stimulation (session 3), while inducing no vomiting and no significant increase in the score of other observable symptoms, food intake was significantly reduced (FIG. 7).

This study demonstrates that RGES with appropriate stimulus is able to reduce food intake without inducing discomfort or vomiting.

Figure 8A:
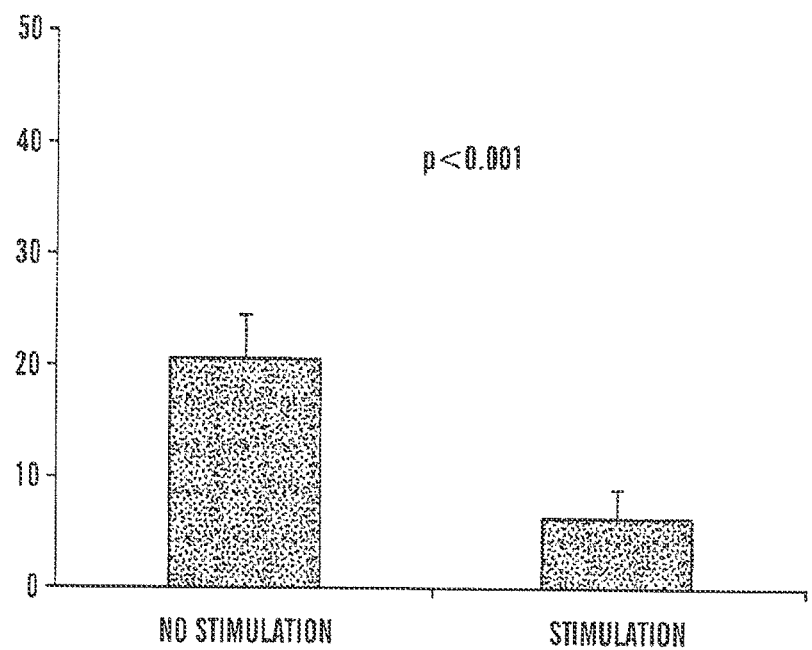
FIGS. 8A and 8B illustrate the effect of RGES at the normal frequency on gastric emptying and slow wave coupling.
Figure 8B:
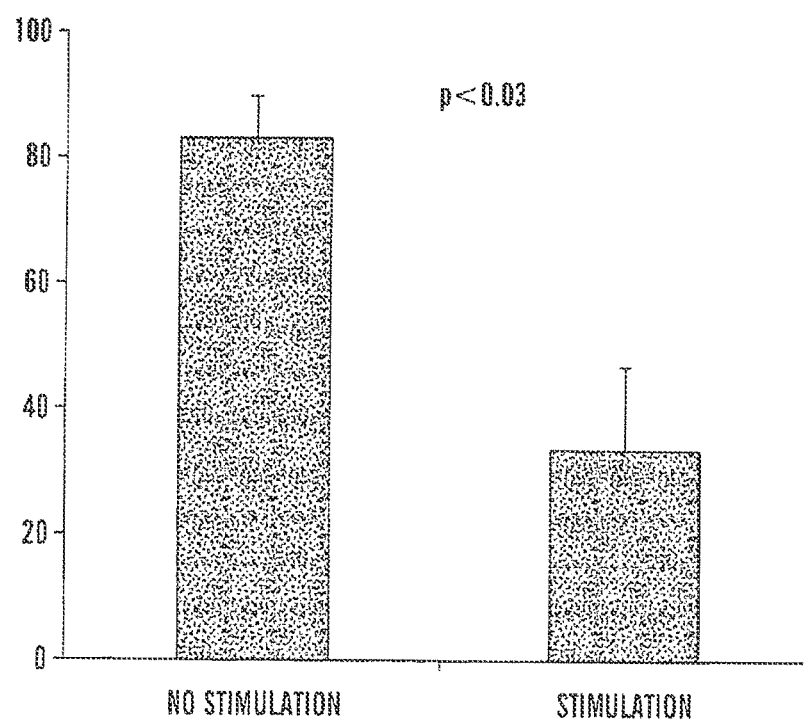

RGES at a "physiological" frequency also impairs slow wave propagation and delays gastric emptying. In addition to the above study, the effect of RGES at a normal frequency on gastric slow waves and gastric emptying was investigated in a separate study (Lin et al., 1999). The experiment was performed in 6 dogs implanted with gastric serosal electrodes as before and equipped with a duodenal cannula for the assessment of gastric emptying (see Materials and Methods). After the ingestion of a liquid meal, electrical stimulation was performed via the distal electrodes with a frequency of 10% higher than the intrinsic frequency of the gastric slow wave. It was found that gastric emptying (30 minutes after eating) was significantly delayed with RGES in comparison with the control session (FIG. 8A). This was accompanied by a significant impairment in gastric slow wave coupling (see Materials and Methods) (FIG. 8B).

This study suggests that the reduction in food intake observed in the feasibility study presented above is attributed to the impairment in gastric emptying and gastric slow wave propagation.

RGES at a tachygastrial frequency inhibits gastric contractions. While RGES at a physiological frequency is effective in delaying gastric emptying and reducing food intake, it is limited in its practical utility because of the high level of energy required. The stimulation pulse width used is about 300-500 ms which is about one thousand times higher than that in cardiac pacing, implying a substantial amount of energy consumption. To overcome this energy consumption issue, RGES at a tachygastrial frequency can be used to achieve the same effects as above. A lower, and possibly much lower, energy is required for RGES at a tachygastrial frequency than for RGES at a normal frequency. RGES at tachygastrial frequency is even more efficient because it not only impairs distal propagation of gastric slow waves but also induces tachygastria in the stomach and further reduces gastric contractions.

In a further experiment, a dog was implanted with 4 pairs of gastric serosal electrodes along the greater curvature and a strain gauge close to the most distal pair of electrodes (2 cm above the pylorus). RGES was performed using the third pair of electrodes (6 cm above the pylorus) at a frequency of 11 cpm (the intrinsic frequency in the dog was about 6 cpm) and a pulse width of 50 ms. As shown in the left half of FIG. 3, normal distally propagated slow waves (top 4 tracings) and regular gastric contractions (bottom tracing) were observed at baseline. After stimulation (right half of FIG. 3), the frequency of gastric slow wave in channel 4 was increased and gastric contractions were diminished. This experiment was repeated several times in the same dog with the same results.

In the RGES procedure, each dog undergoes gastrointestinal pacing during at least 3 separate sessions. These include a "control" session (no stimulation), a "pacing" session (electrical stimulation resulting in a complete entrainment of gastric slow waves in at least one channel adjacent to the stimulation electrodes is called "pacing"), and one or more "optimization" sessions with stimulation energy reduced from the pacing session. Two consecutive sessions are at least 3 days apart.

The protocol for the control session (no electrical stimulation) is as follows (sequentially): a 30-min baseline recording, 30-min with access to unlimited regular solid food (the same food used in daily care of the animal) and water, 60-min postprandial recording after the removal of the food and water.

The protocol for the pacing session is composed of 30-min baseline recording, 15-min RGES, 30-min with access to unlimited food and water with RGES, 60-min postprandial recording with RGES after the removal of food and water. Electrical stimulation parameters are chosen to completely entrain gastric slow waves in the channel adjacent to the stimulation electrodes. Based on the experiments, the following parameters are able to entrain gastric slow waves: stimulation frequency—13 cpm (the normal frequency in the dog is about 5-6 cpm); pulse (square wave) width—500 ms; and pulse amplitude—4 mA (constant current is used in all experiments). A small adjustment is necessary for each particular dog and this is done at the beginning of stimulation by visually inspecting whether the paced slow waves are phase-locked with the stimulus.

The protocol for the optimization sessions is the same as the "pacing" session. However, electrical stimulation is performed with a reduced energy. More than one session is required to optimize the performance of GRES by changing stimulation parameters. The definition of optimization is based on an optimal combination of efficacy, safety and feasibility. That is, the optimal RGES settings are those that result in a significant reduction in food intake (efficacy) but do not induce undesired symptoms, such as nausea or vomiting (safety) with minimal energy (maximally feasible for an implantable device). Iterative adjustments of stimulation parameters are made to achieve this result.

Measurements made during the entire experiment include: food intake, all observable "symptoms", gastric myoelectrical activity, gastric contractions (including fundic tone), gastric compliance, and electrocardiogram. A detailed description of the measurements and analyses of these parameters is provided under the Materials and Methods section.

Analysis of variance (ANOVA) is performed to study the difference in food intake and symptom score (quantitative analysis is described under Materials and Methods) among the control, pacing and stimulation sessions. Effects of RGES on gastric slow waves and gastric contractions is also assessed.

The "pacing" session results in a substantial reduction of food intake but moderate to severe symptoms, such as vomiting. The optimal stimulation session results in a similar reduction of food intake with absolutely no vomiting, and no significant increase in other symptoms in comparison with the control session. The ideal result is a significant and substantial reduction in food intake with absolutely no uncomfortable symptoms and minimal consumption of energy (comparable with that in cardiac pacing).

By contrast with conventional methods of electrical stimulation, this RGES system contains two important additional elements: detection of the outcome of stimulation; and automated control of stimulation based on a pre-determined target (or "prescription"). The pre-determined target is the percentage of impairment of slow waves (=100%-% normal 3.5-7.0 cpm slow waves) measured by the sensing electrodes.

Figure 12:
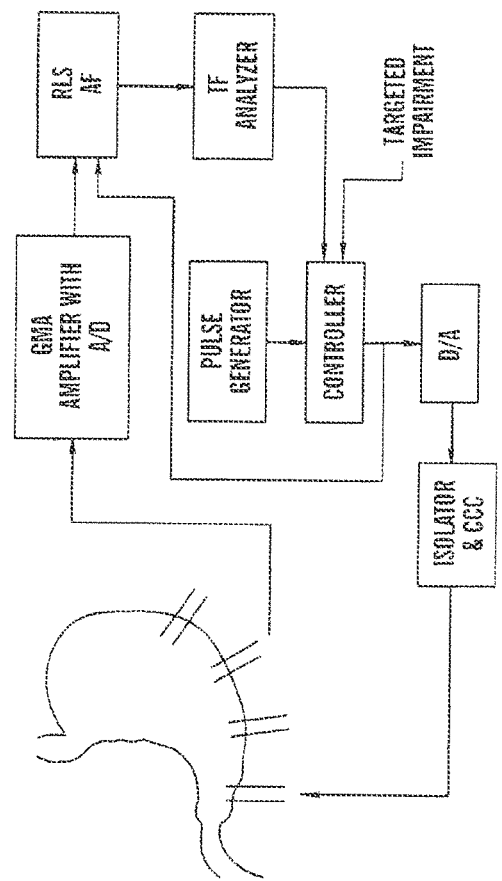
FIG. 12 is a block diagram of a typical RGES system.

FIG. 12 presents the block diagram of the system. The gastric slow wave is recorded with cutoff frequencies of 0.5 to 12 cpm by the sensing electrodes placed in the middle stomach and digitized at a frequency of 1 Hz (60 cpm). The digitized signal is subjected to digital signal processing. Since the recording of gastric slow waves may contain stimulation artifacts, the recording is first processed for the cancellation of stimulation artifacts with an adaptive filter using the recursive least squares (RLS) algorithm. Time-frequency analysis is performed on the artifacts-free gastric recording by the time-frequency analyzer and the percentage of normal gastric slow waves (or the percentage of impairment) is computed from the time-frequency representation. This percentage of impairment is then compared with the targeted impairment by a digital controller. If the computed percentage is within the range of .+−0.5% of the target, the stimulation is maintained without any modification. If the computed percentage of impairment is lower than the target minus 5%, the stimulation energy or pulse width is increased by 10% or a smaller or larger step to be determined by experiments. If the computed percentage of impairment is higher than the target plus 5%, the pulse width is reduced by 10% or a smaller or larger step to be determined by experiments. The digital stimulus is converted into an analog signal by a D/A converter. A constant current control circuit is used to guarantee that constant current is delivered to the stimulation electrodes placed 2 cm above the pylorus.

Maximal and minimal thresholds for pulse width are determined by experiments and pre-set. An alarm is set off if one of the thresholds is reached and the stimulation is switched to a fixed parameter mode (using optimized parameters derived as discussed above). The maximal threshold is used to protect the subject from being hurt with excessive stimulation. The minimal threshold is introduced to protect the system from being ineffective and would be reached in two instances: 1) if the system malfunctions; and 2) if the percentage of normal gastric slow waves before stimulation in the subject is below the targeted impairment. Five minutes after stimulation with the fixed mode, the automatic system is turned on again.

The RGES system has the following advantages: 1) the stimulation is not fixed but dynamically modulated by the outcome of stimulation. It is much easier to optimize the performance in individual subjects than by the somewhat random process of using fixed parameters; 2) the physician can actually "prescribe" the "dosage" of treatment. For example, a higher "dosage" (higher percentage of impairment) may be "prescribed" at the beginning of treatment to loose sufficient weight, followed with a lower "dosage" to maintain weight loss.

Cancellation of stimulation artifacts. Electrical stimulation artifacts are often superimposed on the gastric slow wave recording. These artifacts must be cancelled before the time-frequency analysis of the gastric slow wave. Otherwise, the computed percentage of impairment or normal 3.5-7.0 cpm slow waves would be inaccurate. Similar problems have been encountered and adaptive filtering has been applied for the cancellation of respiratory artifacts superimposed on the abdominal surface recording of gastric slow waves (Chen et al., 1989) or intestinal slow waves (Chen and Lin 1993).

Figure 13:
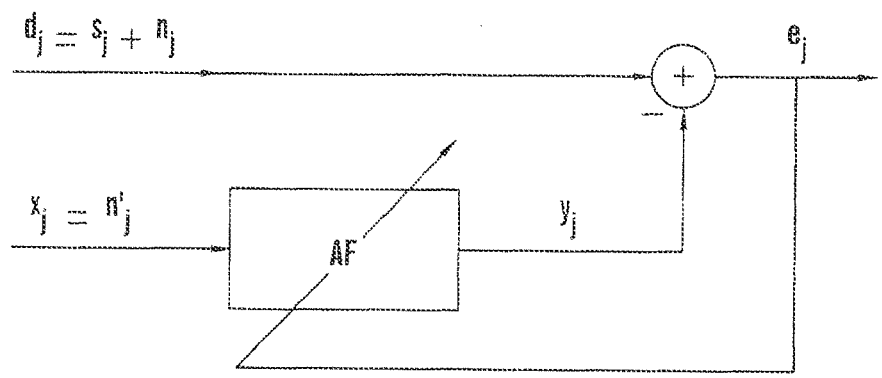
FIG. 13 is a block diagram of an adaptive filter.

The similar technique of adaptive filtering is used with RGES to cancel the stimulation artifacts. As shown in FIG. 13, $d_j$ represents the measurement of gastric slow waves by the sensing electrodes. It contains gastric slow waves ($s_j$) and stimulation artifacts ($n_j$). A reference signal $x_j$ is obtained directly from the stimulator. It is clear that this reference signal is closely correlated with the stimulation artifact, $n_j$, but may have a different phase and amplitude. An adaptive filter (AF) is used to adjust the amplitude and phase of the reference signal such that its output $y_j$ is identical to stimulation artifacts, $n_j$. Consequently, the subtracted output $e_j$ would be artifacts-free.

Various algorithms available for the adaptive filter can be used in this method, including least mean squares algorithm and recursive least squares (RLS) algorithm. The selection of the algorithm is based on the performance and the computational feasibility for an implantable device. An RLS algorithm is a good choice.

Time-frequency analysis of gastric slow waves. Numerous methods are available in the literature for time-frequency analysis (Akay 1995). Short-time Fourier transform (STFT) is among the early works in this area. A sliding window with a short length is used in the STFT and the signal inside the window is assumed to be stationary. Wigner developed another approach (Wigner 1932) which was later adapted to signal processing by Ville (1948). In this case, a quadratic distribution of the time and frequency characteristics of the signal is derived. The major drawback of this representation is in its interpretation. That is, the representation not only contains the signal components but also interference terms, called cross-terms, generated by the interaction of these signal components with each other. Many suggestions have been made to improve the Wigner-Ville distribution, all using some kind of filtering process to enhance the signal components and to attenuate the interference terms. The exponential distribution proposed by Choi-Williams was one of them (Choi and Williams 1989). Cohen (1992) unified the quadratic time-frequency representations. He showed that most of them belonged to a general class, in which each member was generated by the choice of an appropriate kernel function. In the early 1980s, a theory that unified a set of ideas about analyzing a signal at different resolutions was proposed and was called wavelet representation (Rodet 1985; Grossman and Morlet 1984). An interesting characteristic of this method relies on its ability to behave like a mathematical microscope, that is, it can zoom in on short-lived signal components. The wavelet transform (WT) is a signal decomposition on a set of basis function, obtained by dilations, contractions, and shifts of a unique function, the wavelet prototype. A basic distinction between WT and STFT is that while the basic functions of the latter consist of a function of constant width translated in time and filled in with high-frequency oscillations, the former has a frequency-dependent width. In other words, it is narrow at high frequencies and broad at low frequencies. This gives the WT the ability to zoom-in on transitory phenomena, which are usually short-lived components of a signal.

Each of the above mentioned methods has been applied to the time-frequency representation of the gastric slow wave measured from electrogastrography. The STFT method was first introduced and is still being used by various investigators (Chen and McCallum 1995). With the EGG (electrogastrogram, abdominal surface measurement of gastric slow waves) signal sampled at 1 Hz, the STFT is typically performed with a window length of about 4 minutes and a shift of 1 minute between two consecutive Fourier transforms. The disadvantage of this method is its low temporal resolution. Abnormal slow waves with a brief duration cannot be reliably detected.

The Wigner distribution and the exponential distribution were investigated (Lin and Chen 1994). The unmodified Wigner distribution was found inappropriate for the time-frequency analysis of the EGG due to inherent interference terms resulting from noises and interference present in the EGG. The exponential distribution provided much better performance than the Wigner distribution but was not satisfactory, especially when the EGG signal was noisy (Lin and Chen 1994). Its performance in the analysis of the gastric slow wave measured from the implanted serosal electrodes is expected to be better since the serosal recording does not contains much noise or artifacts. The WT method was recently applied in an attempt to identify contraction-related spike potentials in the EGG. However, no convincing data have been provided, suggesting that spike potentials are present in the EGG and that they can be detected using the WT method. In addition to these methods, a so-called adaptive spectral analysis method was developed which is based on the autoregressive moving average (ARMA) model and was implemented using an adaptive ARMA filter (Chen et al., 1990).

The various methods for the time-frequency analysis (or running spectral analysis) of the cutaneously recorded gastric slow waves (Chen et al., 1990; Chen et al., 1993; Lin and Chen 1994; Lin and Chen 1995; Wang et al., 1998; Lin and Chen 1996), or electrogastrography (EGG), are summarized as follows:

Autoregressive Moving Average (ARMA) Modeling with Adaptive Filtering Gastric slow waves can be detected non-invasively using abdominal surface electrodes, a method called electrogastrography. The cutaneous measurement and display of gastric slow waves is called an electrogastrogram (EGG). The EGG contains elements of both gastric signal and noise (or interference) such as respiratory and motion artifact. Spectral analysis methods are used to derive clinically useful parameters from the EGG. Time-frequency analysis methods have been developed or applied for the quantitative assessment of the regularity of gastric slow waves. The most frequently used parameter, the percentage of normal slow waves, was first proposed by Chen (Chen and McCallum 1995; Chen et al., 1995a). It is defined as the percentage of time during which normal gastric slow waves (2-4 cpm in humans and 3.5-7.0 cpm in dogs) is detected from the time-frequency analysis of the EGG. This same parameter is used to provide feedback control of the strength of RGES in the subject method.

The first method of time-frequency analysis developed by Chen was called adaptive spectral analysis (Chen et al., 1990). It is based on an autoregressive moving average (ARMA) model and implemented using an adaptive ARMA filter. The parameters of the adaptive ARMA filter are adapted each time when a new sample is available using the least mean square (LMS) algorithm. The instantaneous frequency of the signal is computed from the filter parameters based on the ARMA model. This method has been refined and used for numerous years (Chen and McCallum 1995; Chen et al., 1995a; Chen et al., 1993; Lin and Chen 1996; Chen and McCallum 1991). It is adaptive, robust and relatively simple in computation.

Choi-William Exponential Distribution The second method for the time-frequency analysis of the EGG was the Choi-William exponential distribution (Lin and Chen 1994). This method was introduced by Choi and Williams (1989). It is a new distribution with an exponential-type kernel, which they called exponential distribution. This method was initially developed to solve the problem of cross-terms generated by the Wigner distribution. An optimal performance may be obtained for a particular application by a tradeoff between cross-term suppression and auto-term reduction. Experimental data with the EGG show that this method provides a good performance when the EGG has a high signal-to-noise ratio. The performance is not satisfactory when the EGG is corrupted with noises and interference.

Overcomplete Signal Representation Traditionally, a signal is represented using an expansion of a particular orthogonal basis, such as Fourier basis, discrete cosine basis and wavelet basis, and the number of expansion is chosen such that the representation is unique. This representation is called complete signal representation. In contrast to complete signal representation, overcomplete signal representation uses a higher number of bases than the number of frequency components of the signal. Most recently, the concept of overcomplete signal representation has been applied for the time frequency analysis of the gastric slow wave and two algorithms have been proposed for the optimization of the overcomplete signal representation. One algorithm is the fast algorithm of matching pursue and the other is based on an evolutionary program (Wang et al., 1998). In addition, the so-called minimum fuel model was utilized and a special neural network was developed for it to optimize overcomplete signal representation.

Selection of the Time-Frequency Analysis Method Selection of the time-frequency analysis method to be used in the RGES system is based on the following criteria: 1) reliability and robustness; 2) accuracy; and 3) feasibility. A comparison among various time-frequency analysis methods was previously made (Lin and Chen 1995). The adaptive spectral analysis method is probably the best for this RGES system. It is reliable and robust. Its accuracy has been validated in several different studies (Chen et al., 1993 80; Chen and McCallum 1991). It uses the least mean square (LMS) algorithm (simple in computation), which makes it very feasible to be incorporated into an implantable stimulator. Other methods, such as STFT, exponential distribution and WT, can be investigated in comparison with the adaptive spectral analysis method. The over-complete signal representation method is probably too complicated for an implantable device (Wang et al., 1998).

Adaptive Spectral analysis is based on the autoregressive moving average (ARMA) model. In this method, it is assumed that a signal $S_n$ (n: time instant) can be generated by exciting an ARMA process using a random time series, $n_n$. Mathematically, it can be written as follows:

$$S_n = -\sum_{k=1}^{p} a_k s_{n-k} + \sum_{k=1}^{q} c_k n_{n-k} + n_n$$

where $a_k$ (k=1, 2, ..., p) and $c_k$, (k=1, 2, ... q) are called the ARMA parameters. The power spectrum of the signal, $s_n$, can be calculated from these ARMA parameters.

Figure 14:
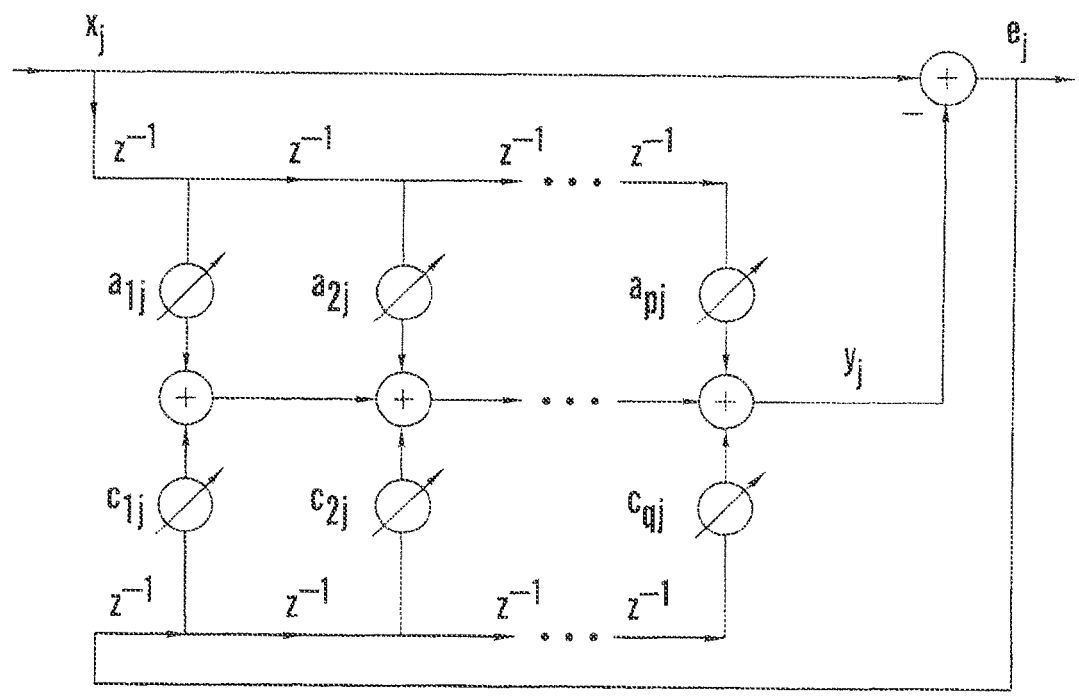
FIG. 14 details the structure of the adaptive ARMA filter.

To model a real signal $x_n$, one simply proceeds in the opposite direction. By constructing a so-called adaptive ARMA filter (see FIG. 14, $z^{-1}$ stands for one sample delay), the output signal, $y_n$, now can be made to approximate the input signal, $x_n$. It is expressed as:

$$y_n = \sum_{k=1}^{p} a_{k,n} x_{n-k} + \sum_{k=1}^{q} c_{k,n} e_{n-k}$$

where $a_{k,n}$ and $c_{k,n}$ are time-varying parameters and $e_n$ is the estimation error:

$$e_n = x_n - y_n$$

The ARMA parameters are initially set as zeros and iteratively adjusted by the least mean squares (LMS) algorithm, expressed as follows:

$$c_{k,n}+1 = c_{k,n} + 2\mu_c e_n e_{n-k} = k=1, 2, \ldots, q$$

$$a_{k,n}+1 = a_{k,n} + 2\mu_a e_n e_{n-k}, k=1, 2, \ldots, p$$

where step-sizes, $\mu_a$ and $\mu_c$ are small constants controlling the adaptation speed of the LMS algorithm (Chen et al., 1993). The algorithm states that the filter parameters at each successive time step, $a_{k,n+1}$ and $c_{k,n+1}$, are equal to their current values, $a_{k,n}$ and $c_{k,n}$, plus a modification term. The number of the filter parameters used is equal to q+p. The best value for q may be associated with specific applications. The value of p must be greater than or equal to the number of digitized points that span the longest rhythmic cycle of interest in a signal. For example, if the period of the rhythmic component of interest in a signal is 20 seconds (0.05 Hz or 3.0 cpm) and the sampling frequency is 2 Hz, the smallest value of p should be 40. This requirement of this large value is attributed to the nature of the LMS algorithm.

Once the adaptive filter converges, the power spectrum of the input signal $x_n$, can be calculated from the filter parameters. At any point in a time series, a power spectrum can be calculated instantaneously from the updated parameters of the model. Similarly, the power spectrum of the signal for any particular time interval can be calculated by averaging the filter parameters over that time interval.

Figure 15:
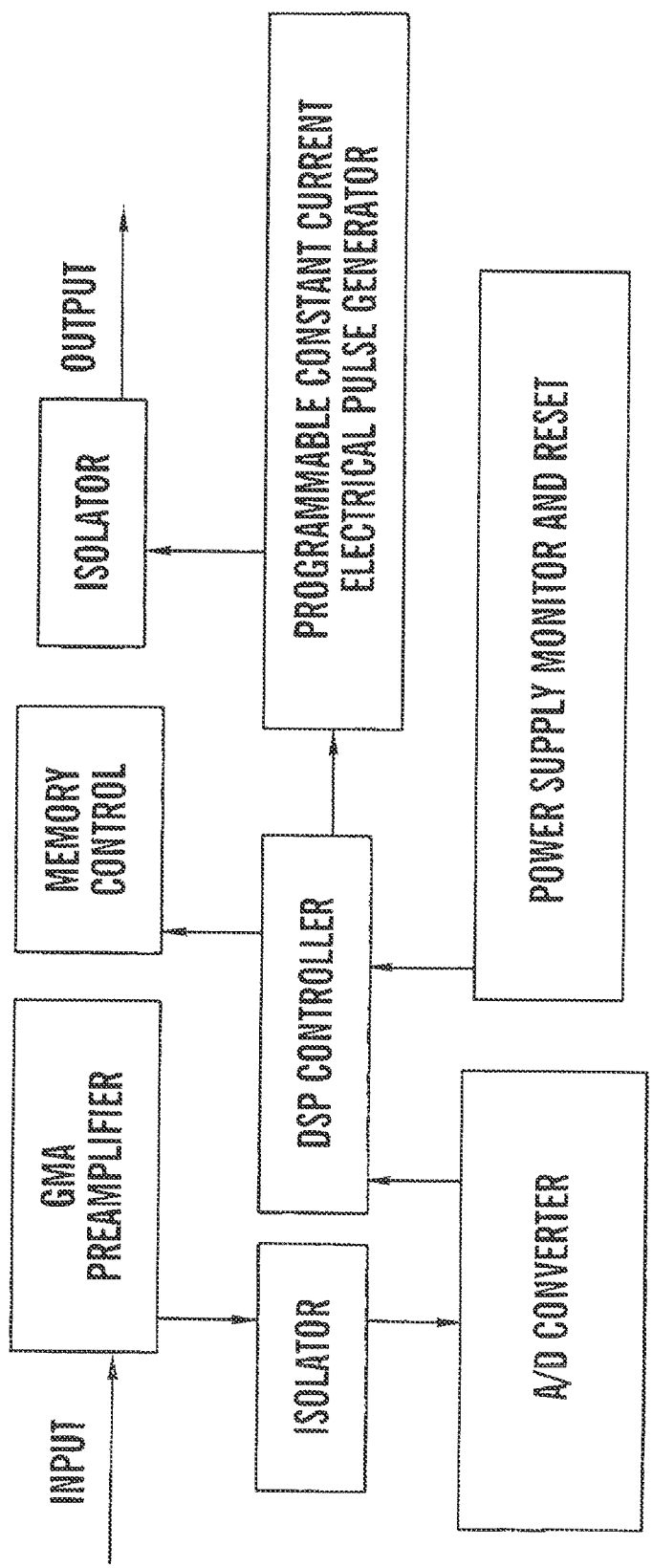
FIG. 15 is a block diagram of a portable stimulator.

The implementation of the RGES system in a portable device is shown in FIG. 15. It contains similar components as those shown in FIG. 13. A new element of the RGES stimulator is the addition of a DSP (digital signal processing) controller.

Example 3

Portable stimulators for gastric electrical stimulation are feasible and effective. A portable electrical stimulator was previously developed (Chen et al., 1995b) and used in more than 20 patients (see FIG. 9). The stimulator uses fixed parameters and delivers stimulation pulses with a frequency of 3 cpm, pulse width of 300 ms and pulse amplitude of 4 mA (constant current mode). The constant current is guaranteed with a load in the range of 300-1000 W. The stimulator is operated by a 9-volt battery with an easy access for replacement. A female pin is available to connect the stimulator with the stimulation electrode wire. There is a manual switch for turning on or off the stimulator. This stimulator has been used in a clinical research study (McCallum et al. 1998) with no malfunction or adverse events reported.

Example 4

Electrical Field Stimulation

This example illustrates the entrainment of gastric slow waves and the acceleration of gastric emptying using gastric electrical field stimulation. Two electrodes are placed on the serosa of the stomach. Unlike the bipolar or monopolar methods of the prior art, one electrode is placed in the proximal stomach and the other in the distal stomach. The proximal electrode has a positive polarity, and the distal one has a negative polarity. Electrical stimulation is performed via these two electrodes. The stimulation frequency is 10% higher than the natural frequency of the gastric slow waves. Instead of single pulses, a train of pulses with a frequency in the range of 1 to 50 Hz is used for each stimulus.

By placing the two stimulator electrodes in the gastric cardiac area close to the lower esophageal sphincter (LES), the methods can be used for the treatment of gastric esophageal reflux (by increasing the LES pressure) or achalasia (by relaxing the LES).

Example 5

Electrical Field Stimulation of the Vagus Nerve

Gastric Electrical Stimulation Affects Vagal Efferent Activity in Dogs

Figure 11:
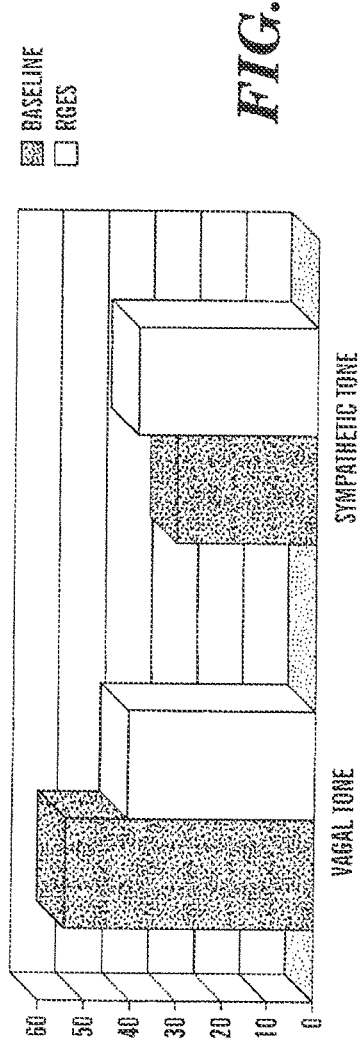
FIG. 11 illustrates the effect of RGES on vagal and sympathetic tone.

Evidence of an effect of gastric electrical stimulation on vagal activity is provided in this Example. These studies were performed in 5 healthy female hound dogs implanted with one pair of serosal electrodes on the greater curvature 2 cm above the pylorus. The experiment was performed in the fasting state after a complete recovery from surgery. The protocol consisted of 30-min baseline, 30-min stimulation and 30-min recovery. The stimulus was composed of a series of pulse trains. The pulse train was on for 2 seconds and off for 3 seconds. The pulse in each train had a frequency of 40 Hz, a pulse width of 200 us and an amplitude of 4 mA. A significant increase in the ratio of sympathetic and vagal activities (assessed using the spectral analysis of the heart rate variability signal as described) was observed with RGES ($0.93 \pm 0.49$ with GRES in comparison with $0.67 \pm 0.49$ ($p<0.04$) at baseline). This increase was attributed to an decrease in the percentage of vagal activity ($40.6 \pm 9\%$ vs. $54 \pm 12\%$, $p=0.06$) and an increase in the percentage of sympathetic activity ($39 \pm 12\%$ vs. $31 \pm 14\%$, $p<0.05$) (see FIG. 11) (Wang et al., 2000b).

In another experiment (Wang et al., 2000a), the effect of different stimulation frequencies on vagal efferent activity in 5 dogs was investigated using antegrade gastric electrical stimulation. It was found that stimulation at a physiological frequency enhanced vagal efferent activity, whereas stimulation at a tachygastrial frequency inhibited vagal efferent activity.

Example 6

Placement of Electrodes

This example illustrates a method for the placement of electrodes in the gut without any surgical intervention. Previous methods of electrode placement generally involve the implantation of electrodes on the serosa of the gut via open surgery or laparoscopic surgery. General anesthesia and hospital stay are necessary.

In this example, electrodes are placed via endoscopy without general anesthesia or hospital stay. First, the conscious patient is sedated and an endoscope is inserted into the stomach or small intestine via the mouth. This step is optional, and is for the purpose of observing the placement of the electrodes. Then, a sharp, long and small needle with a hole in the middle (the same needle used for the placement of percutaneous endoscopic gastrostomy tubes) is inserted into the stomach or small intestine. A teflon-isolated wire is then inserted into the stomach or small intestine via the hole of the needle under endoscopy. The teflon at the distal portion of the wire is peeled off so that the exposed portion of the wire serves as an electrode. There are barbs arranged circumferentially at the end tip of the wire. The needle is removed after the insertion of the wire. The wire is slowly pulled back until the barbs contact the mucosa and stop the wire from being further pulled out. The wire on the abdomen is attached to the abdominal skin and protected from infection. Various numbers of wires can be placed in this manner, without the need to hospitalize the patient. Therefore, the patient can be discharged after a few hours of recovery from sedation. The monitoring and electrical stimulation of the colon may also be done with the electrodes being placed in a similar manner but via colonoscopy.

Example 7

Figure 17:
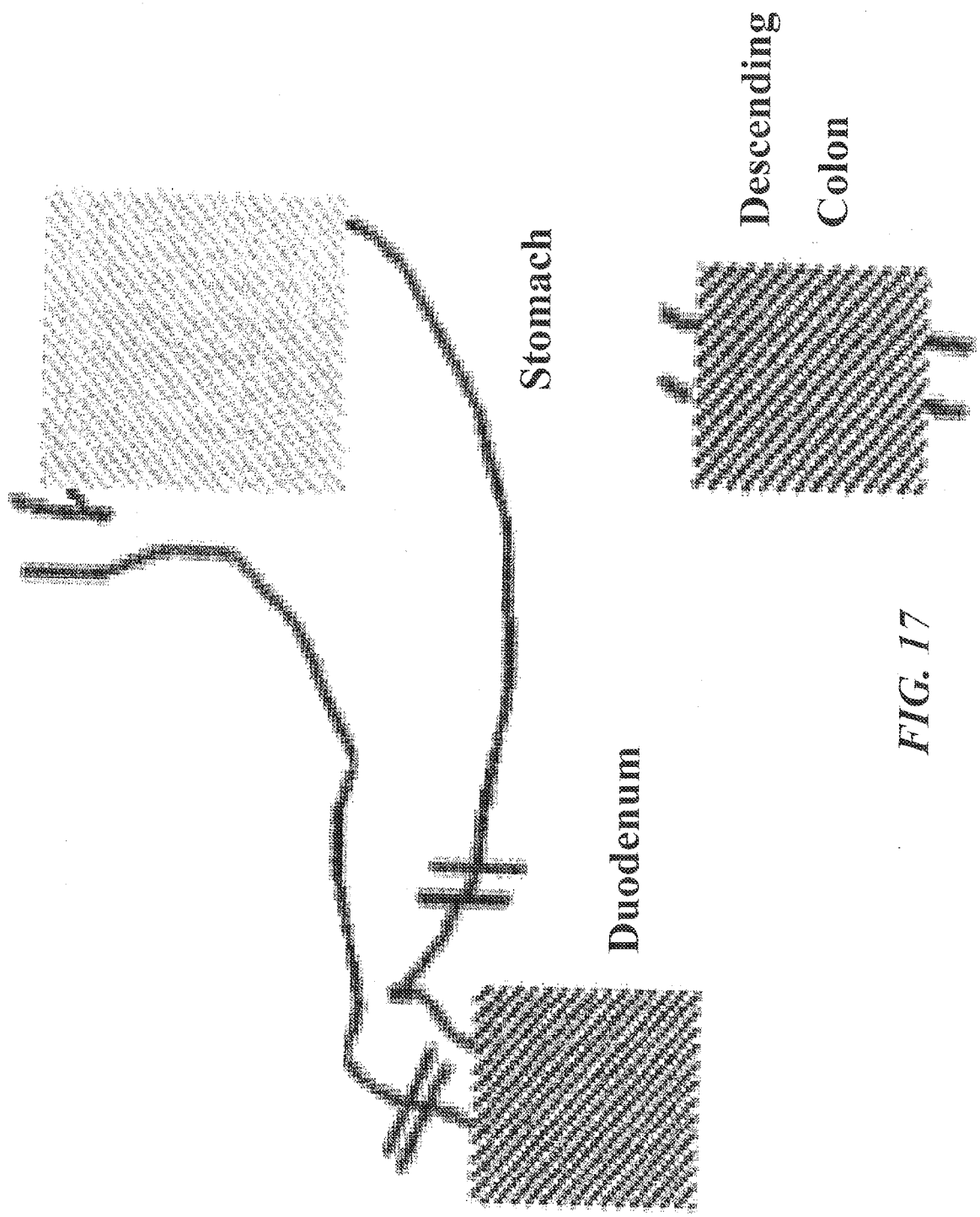
FIG. 17 illustrates experimental model for gastric and duodenal electrical stimulation. The pair of electrodes near the gastric greater curvature and the duodenum was used for gastric electrical stimulation and duodenal electrical stimulation, respectively. Tissues were harvested from the shaded regions as indicated.

Adult male Sprague-Dawley® rats (300-350 g, Harlan Sprague-Dawley, Houston, Tex.) were housed in wire-bottom cages in a temperature-controlled environment with a temperature of 22° C., 40% humidity and a 12-h light-dark cycle. Rats had free access to regular chow pellets and drinking water. There was one week of acclimatization prior to the initiation of these experiments. After an overnight fast, all rats underwent surgery under anesthesia. A midline laparotomy was performed and 1 pair of 28-gauge cardiac pacing wires (A&E Medical, Farmingdale, N.J., USA) were implanted either on the serosal surface of the stomach in the distal antrum of the great curvature 0.5 cm proximal to the pylorus or the duodenum 0.5 cm distal to the pylorus as shown in FIG. 17. The electrodes (stainless steel wire) in each pair were 0.3 cm apart, penetrated subserosa and were affixed to the gastric serosa by unabsorbable sutures. The connecting wires were tunneled subcutaneously through the anterior abdominal wall along the right side of the trunk, and led outside the skin to the back of the neck for attachment to the stimulator. The abdominal wall and skin were closed in a simple interrupt pattern. After surgery, all animals were able to ambulate and had unrestricted access to food and water. GIES was initiated 3 days after surgery and electrode implantation.

Rats were divided into 4 groups (8 rats per group): The first group was designated as the control group and was selected for sham stimulation, gastric electrodes were implanted and contacted to the stimulator but no electrical stimulation applied. The second group was subjected to GES with pulse trains. The third group was administered GES with long pulses; and a fourth group was administered DES with pulse trains. Three days after surgery, the rats were fasted at 4 p.m. and electric stimulation was initiated at 8 a.m. the next day for two hours. After stimulation, the rats were sacrificed immediately. Gastric fundus, duodenum and distal colon tissues were harvested and extracted for ghrelin, obestatin, CCK-8 and PYY3-36 radioimmunoassay (RIA) analysis, respectively. FIG. 17 demonstrates the shaded regions of the stomach and intestines that were harvested for this study.

Figure 18:
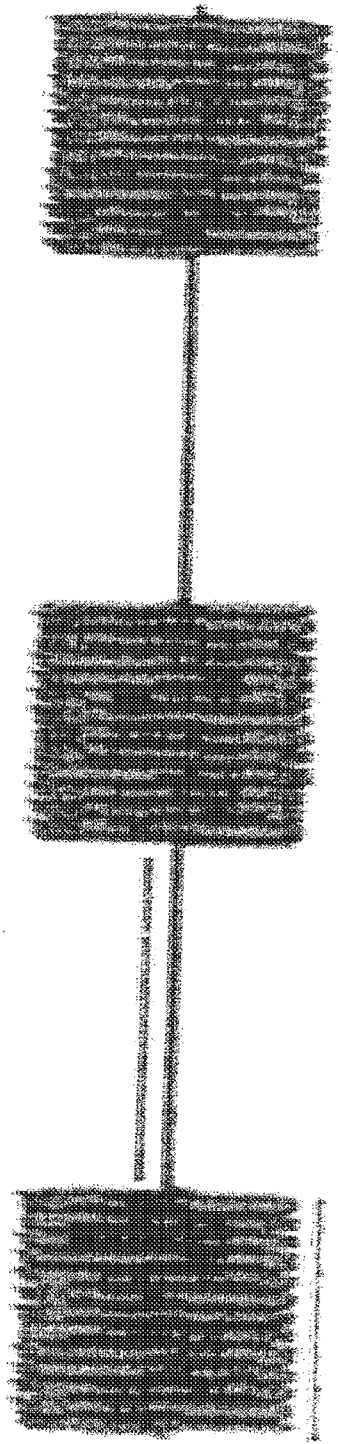
FIG. 18 illustrates experimental model for gastric and duodenal electrical stimulation. The pair of electrodes near the gastric greater curvature and the duodenum was used for gastric electrical stimulation and duodenal electrical stimulation, respectively. Stimulation parameters applied included.
Figure 18:
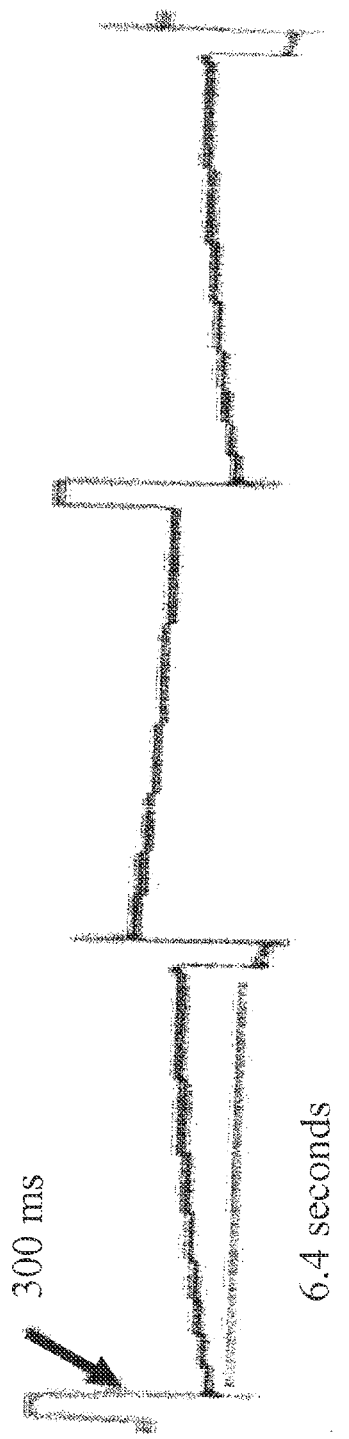

GES and DES were applied via the electrodes using an adjustable electrical stimulator (Model A31 0, World Precision Instruments, Sarasota, Fla., USA) at the distal antrum of greater curvature and the duodenum respectively. One stimulation parameter evaluated in this study was IGS-3 ms: modified IGS parameters used for obese patients: a pulse frequency of 40 Hz, a width of 3 ms and amplitude 6 mA, and train on-time of 2 s and off-time of 3 s as shown in FIG. 18. A pulse width of 0.3 ms is commonly used in clinical trials. Recent studies in our lab demonstrated that a pulse width of 3 ms was more effective in altering both gastric motility and central neuronal activities. A second stimulation parameter evaluated in this study was repetitive long pulses. A frequency of 9 pulses/min, a width of 300 ms and amplitude of 6 mA as shown in FIG. 18. GIES with these parameters was shown to reduce food intake and induce weight loss in Obese Zucker rats.

Tissues from the gastric fundus, duodenum and colon were quickly removed after the rats were sacrificed. They were diced and boiled for 15 min in a 5-fold of solutions that were adjusted to a final concentration of 1M AcOH and 20 mM HCL to deactivate intrinsic proteases. After cooling, the tissues were homogenized with a Polytron mixer and placed in a centrifuge at 13,000 rpm at 4 C for 20 min (per recommended RIA protocol for tissue preparation). Tissue sample supernatants were aspirated and protein levels were measured. Four grams of tissue samples were loaded on an equilibrated SEP-Pak C18cartridge (Phoenix Pharmaceuticals, Inc). Equilibration was performed by washing once with 1 ml of buffer B (60% acetonitril in 1% TFA) and three times with 3 ml of buffer A per manufacturers protocol. The peptides were then eluted from the columns with 3 ml of buffer B and collected in a 15-ml polystyrol tube, evaporated to dryness and subjected to ghrelin, obestatin, CCK-8 and PYY3-36 specific RIA31.

Ghrelin, obestatin, CCK-8 and PYY tissue concentrations were determined by a double-antibody radioimmunoassay (RIA) procedure. First, RIA was performed on serial dilutions of one normal tissue sample to determine the optimal titration concentrations to place our samples into the linear range of the assay. There was a good correlation between the tissue protein levels and the peptide hormone levels, as shown in FIG. 19. Based on pilot studies, variable concentrations of extracted protein preparations were needed from the gastric, duodenal and distal colonic regions for ghrelin, CCK-8 and PYY 3-36 quantization assays (25 ug, 50 ug and 100 ug, respectively, as shown in FIG. 19). Gastric obestatin could be detected only using 1 mg of tissue samples. Analyses were performed according to the manufacturer's recommendations (Phoenix, Pharmaceuticals, Inc; Belmont, Calif., USA). The tracer was radio-iodinated ($^{125}$I) rat peptide and the minimum detectable amount for ghrelin was 5.4 pg/tube with 5% inter- and 13% intra-assay coefficients of variation (CV). For obestatin, 10 pg/tube was detectable with 5-7% inter- and 10-12% intra-assay CV; CCK-8: 5.9 pg/tube was detectable with 5-7% inter- and 10-12% intra-assay CV; and PYY: 1 pg/tube was detectable with the intra-assay variation <8.42% and inter-assay variation <14.52%. Rabbit anti-rat peptide serum (100 ul) was added for the detection of each hormone.

After incubation for 16-24 hours at 4° C., ($^{125}$I) peptide (100 µl) was added to each assay tube and incubated for another 16-24 hours at 4° C. Then, 100 µl of goat anti-rabbit IgG serum and 100 µl normal rabbit serum were added to each assay tube. The precipitates were separated by centrifugation (3000 rpm, 20 min, 4° C.) and the radioactivities were counted using an auto-Gamma counting system (PACKARD Instrument Co, Meriden, Conn.). Each sample was assayed and a standard curve was obtained from the measurements in duplicate.

Statistical analysis was performed using SPSS 11.5 software. All data are represented as mean±SE. One-way analysis of variance (ANOYA) and unpaired Student's t-test were used to test for statistical significance compared to sham stimulation. A P value of <0.05 was considered significant.

FIG. 20 demonstrates that the gastric fundus ghrelin level was significantly decreased with both GES and DES. Gastric fundus ghrelin level was significantly decreased in the rats with GES with pulse trains compared to sham stimulation (597.9±195.3 pg/mg vs. 1789.0±362.8 pg/mg, p=0.012). Gastric fundus ghrelin level was also significantly decreased in the rats with GES of long pulses and with DES (754.6±282.6 pg/mg and 731.7±11 0.8 pg/mg respectively, p=0.039 and 0.037, respectively, compared to sham stimulation).

Gastric obestatin levels were not altered by any of the electrical stimulation methods. The obestatin concentration in the stomach was 18.4±1.8 pg/mg in the sham stimulation rats, 17.7±2.3 pg/mg in the rats with GES of pulse trains (P=O.78, vs. sham stimulation), 15.0±1.0 pg/mg in the rats with GES of long pulses (P=0.16, vs. sham stimulation) and 31.4±7.3 pg/mg in the DES session (P=0.12, vs. sham stimulation).

The duodenal CCK-8 concentration was significantly increased by DES but not GES. The CCK-8 level was significantly increased with DES compared to sham stimulation (762.6±98.8 pg/mg vs 413.3±42.1 pg/mg, respectively, p=0.013) as shown in FIG. 20. The duodenal CCK-8 levels were not significantly elevated with GES with pulse trains or GES of long pulses (510.4±86.0 pg/mg and 479.4±57.6 pg/mg respectively, p=0.36 and 0.4 respectively, compared to sham stimulation).

Distal colon PYY levels were not altered by GES or DES. The PYY concentration in the distal colon was 482.16±137.48 pg/mg in the sham stimulation rats and was not significantly altered using GES with pulse trains, GES of long pulses, or DES (259.3±17.5 pg/mg, 346.6165.9 pg/mg and 353.8±74.9 pg/mg respectively; p=0.15, 0.35 and 0.39 respectively, compared to sham stimulation) as shown in FIG. 20.

Although preferred embodiments have been depicted and described in detail herein, it will be apparent to those skilled in the relevant art that various modifications, additions, substitutions and the like can be made without departing from the spirit of the disclosure and these are therefore considered to be within the scope of the disclosure as defined in the claims which follow.

REFERENCES

PCT/US1998/026506
U.S. Pat. No. 5,292,344
U.S. Pat. No. 5,423,872
U.S. Pat. No. 5,690,691
U.S. Pat. No. 5,836,994
U.S. Pat. No. 6,542,776
U.S. Pat. No. 7,016,735

U.S. Pat. No. 7,076,306
U.S. Pat. No. 7,177,693
U.S. Pat. No. 7,203,551
U.S. Pat. No. 7,310,557
U.S. Pat. No. 7,363,084
U.S. Pat. No. 7,477,994
U.S. Pat. No. 7,599,736
U.S. Pat. No. 7,676,270
U.S. Pat. No. 7,711,437
U.S. Pat. No. 7,720,539
AACE/ACE Position Statement on the Prevention, diagnosis, and treatment of obesity. *Endocrine Practice,* 4:297-330 (1998).
Abo, M, et al., *Dig. Dis. Sci.,* 45:129-135 (2000).
Akay, M., Ed., Time frequency and wavelets in biomedical signal processing. IEEE Press, New York (1995).
Alpert, M A and M W Hashimi, *Am J. Med. Sci.,* 306:117-123 (1993).
Asakawa, A, et al., *Gastroenterology,* 116:1287-1292 (1999).
Balsiger, B M, et al., *Medical Clinics of North America,* 84 (2):477-489 (2000).
Bandini, L G, et al., *Am. J. Clin. Nutr.,* 52:421-425 (1990).
Bellahsene, B E, et al., *Am. J. Physiol.,* 262:G826-G834 (1992).
Benotti, P N and R A Forse, *Am. J. Surg.,* 169:361-367 (1995).
Bray, G A and F L Greenway, *Endocr. Rev.,* 20 (6):805-875 (1999).
Brolin, R E, et al., *Ann. Surg.,* 215:387-395 (1992).
Chen, J D Z and Z Y Lin, *Comp. Biol. Med.,* 23:497-509 (1993).
Chen, J D Z and R W McCallum, *Med. Biol. Eng. Comput.,* 29:339-350 (1991).
Chen, J D Z and R W McCallum, *Am. J. Gastroenterol.,* 88:1324-1336 (1993).
Chen, J D Z and R W McCallum, Electrogastrography: principles and applications. New York: Raven (1995).
Chen, J D Z, et al., *Med. Biol. Eng. Comput.* 27:57-63 (1989).
Chen, J D Z, et al., *Med. Biol. Eng. Comput.* 28:531-536 (1990).
Chen, J D Z, et al., *IEEE Trans. Biomed. Eng.,* 40:128-135 (1993).
Chen, J D Z, et al., *Dig. Dis.,* 13:275-290 (1995a).
Chen, J D Z, et al., *Proc. 17th Intl. Conf. IEEE Eng. Med. Biol. Soc. Canada,* (1995b).
Chen, J D Z, et al., *IEEE-EMBC and CMBEC, Theme 7: Instrumentation,* pp. 1691-1692 (1995c).
Chen, J D Z, et al., *J. Gastro. Hepato.,* 13 (Suppl.):5232-5236 (1998).
Choi, H-I and W J Williams, *IEEE Trans. ASSP* 37:862-871 (1989).
Cohen, L, in Time-Frequency Signal Analysis—Methods and Applications, Boashash, B, Ed., Melbourne, Longman-Cheshire, pp 3-42 (1992).
Colditz, G A, *Am. J. Clin. Nutr.,* 55 (Suppl 2):503S-507S (1992).
Consensus Development Conference Panel, Annals of Internal Medicine 15:956-961 (1991).
Despres, J P, *Nutrition,* 9:452-459 (1993).
Doldi, S B, et al., *Obesity Surgery,* 10 (2):171-173 (2000).
Douglas, N J, *Eur. J. Clin. Invest.,* 25:285-290 (1995).
Duggan, J P and D A Booth, *Science,* 231:609-611 (1986).
Eagon, J C and K A Kelly, *Am. J. Physiol.,* 265:G767-G774 (1993).
Enzi, G, *PharmacoEconom.,* 5 (Suppl 1):54-57 (1994).
Enzi, G, et al., *J. Int. Med. Res.,* 4:305-318 (1976).
Flegal, K M, et al., *Int. J. Obse. Relat. Metab. Disord.,* 22:39-47 (1998).
Frederich, R C, et al., *Nat. Med.,* 1:1311-1314 (1995).
Fried, M, et al., Hepatogastroenterology, 44:582-587 (1997).
Gortmaker, S L, et al., *N. Engl. J. Med.,* 329:1008-1012 (1993).
Greenway, F L, *Am. J. Clin. Nutr.,* 55 (Suppl 1):2035-2055 (1992).
Grossman, A and J Morlet, *SIAM J. Math. Anal.,* 15:723-736 (1984).
Hocking, M P, et al., Gastroenterol., 103:1811-1816 (1992).
House Committee on Small Business. Deception and Fraud in the Diet Industry: Hearing Before the Subcommittee on Regulation, Business Opportunities, and Energy, 101st Congress, 2nd Session. Washington, D.C.: Government Printing Office, 101-150 (1990).
Hvizdos, K M and A Markham, *Drugs,* 58 (4):743-760 (1999).
Institute of Medicine Food and Nutrition Board Committee to Develop Criteria for Evaluating the Outcomes of Approaches to Prevent and Treat Obesity. In: Weighing the Options: Criteria for Evaluating Weight-Management Programs. Thomas, P R, Ed., Washington D.C.: National Academy Press (1995).
Kissebah, A H, et al., *Med. Clin. North Am.,* 73:111-138 (1989).
Klein, S, *Clinical Perspectives in Gastroenterology,* 3:232-236 (2000).
Kuczmarski, R J, et al., *JAMA,* 272:205-211 (1994).
Kuczmarski, R J, et al., *Obes. Res.,* 5:542-548 (1997).
Lasagna, L, Phenylpropanolamine: a Review. New York: John Wiley & Sons (1988).
Le Riche, W H and A Csima, *Can. Med. Assoc. J.,* 97:1016-1020 (1967).
Lin, Z Y and J Chen, *IEEE Trans. Biomed. Eng.,* 41:267-275 (1994).
Lin, Z Y and J D Z Chen, *Med. Biol. Eng. Comput.,* 33:596-604 (1995).
Lin, Z Y and J D Z Chen, *Crit. Rev. Biomed. Eng.,* 24:1-72 (1996).
Lin, Z Y, et al., *Am. J. Physiol.,* 274 (1 Pt 1):G186-191 (1998).
Lin, X M, et al., *Gastroenterology.* 116:A970 (1999).
Lin, X M, et al., *Dig. Dis. Sci.,* 45:652-656 (2000a).
Lin, X M, et al., *Ann. of Biomedical Engineering,* 28:582-587 (2000b).
Lu, C L, et al., *Dig. Dis. Sci.* 44:857-861 (1999).
Martin, L F, et al., *South Med. J.,* 88:895-902 (1995).
McCallum, R W, et al., Gastroenterol., 114:456-461 (1998).
Miedema, B W, et al., *Surg.,* 111:143-150 (1992).
Mintchev et al., *Gut,* 43 (5):607-611 (1998).
Mintchev et al., *Journal of Medical Engineering & Technology,* 23 (1):5-9 (1999).
Mintchev et al., *Gastroenterology,* 118 (2):258-263 (2000).
Moran, T H and P R McHugh, *Am. J. Physiol.,* 242:R491-R497 (1982).
Morley, J E, *Endocr. Rev.,* 8:256-287 (1987).
Nakajima, T, et al., *Circulation,* 71:481-486 (1985).
Namnoum, A B, *Female Patient,* 18:33-44 (1993).
National Institutes of Health Consensus Development Panel on the Health Implications of Obesity. *Ann. Intern. Med.,* 103 (6 Pt 2):1073-1077 (1985).
Nightengale, M L, et al., *May. Clin. Proc.,* 66:773-782 (1991).
Phillips, R J and T L Powley, *Am. J. Physiol.,* 271:R766-R779 (1996).
Qian, L W, et al., *Am. J. Physiol. (Gastrointest. Liver. Physiol.,* 39) 276:G387-392 (1999).
Rodet, X, *Comput. Music J.,* 8:part 3 (1985).
Sagar, P M, *Br. J. Surg.,* 82:732-739 (1995).

Scopinaro, N, et al., *Int. J. Obes.*, 5:421-429 (1981).
Scopinaro, N, et al., *Surgery*, 119:261-268 (1996).
Sheldon, R J, et al., *Regul. Pept.*, 28:137-141 (1990).
Smith, I G, "Long-term weight loss with sibutramine (MERIDIA™), a once-daily serotonin and norepinephrine reuptake inhibitor." Abstract presented at the annual conference of the North American Association for the Study of Obesity; Cancun, Mexico (November 1997).
Sobal, J, et al., *Psychol. Bull.*, 105:260-275 (1989).
Stunkard, A J, *Am. J. Med.*, 100:230-236 (1996).
Sugerman, H J, et al., *Am. J. Clin. Nutr.*, 55 (Suppl 2):560S-566S (1992).
Telander, R L, et al., *Gastroenterology*, 75:495-501 (1978).
Thompson, P D, N. Engl. J. Med., 337:1772 (1997).
Tougas, G, et al., *Am. J. Gastroenterology*, 95:1456-1462 (2000).
Troiano, R P, et al., *Arch. Pediatr. Adolesc. Med.*, 149:1085-1091 (1995).
Van Itallie, T B, *Ann. Intern. Med.*, 103:983-988 (1985).
Ville, J, Cables et al., *Transmission*, 2A:61-74 (1948).
Wang, Z S, et al., *Ann. Biomed. Eng.*, 26:859-869 (1998).
Wang, Z S, et al., *Gastroenterology*, 118:A669 (2000a).
Wang, Z S, et al., *Gastroenterology*, 118:A1204 (2000b).
Wigner, E P, *Phys. Rev.*, 40:749-759 (1932).
Wolf, A M and G A Colditz, *Obes. Res.*, 6:97-106 (1998).
Wright, R A, et al., *Gastroenterology*, 84:747-751 (1983).
Yamada, T, et al., Eds., Textbook of Gastroenterology. Philadelphia: J. B. Lippincott Company (1995).
You, C H and W Y Chey, *Gastroenterology*, 86:1460-1468 (1985).

What is claimed is:

1. A method of regulating the appetite of an individual in need thereof comprising: administering electrical stimulation having a pulse width of 3 ms through a first pair stimulatory electrodes in contact with a gastrointestinal site along the afferent vagus neural pathway.

2. The method of claim 1, further comprising administering a phased pulse regimentation of said electrical stimulation which progresses from the first pair of electrodes to a said second pair of electrodes in contact with a second gastrointestinal tract site.

3. The method of claim 1, wherein the gastrointestinal tract site is a gastric cavity or a duodenal cavity.

4. The method of claim 1, further comprising measuring ghrelin or CCK-8.

5. The method of claim 1, wherein said individual suffers from obesity.

6. The method of claim 1, wherein the electrical stimulation has a pulse frequency of 40 Hz.

7. The method of claim 6, wherein the electrical stimulation has and an amplitude of 6 mA.

8. The method of claim 6, wherein the electrical stimulation has an on-time of 2 seconds and an off-time of 3 seconds.

9. The method of claim 1, wherein said individual suffers from compulsive eating, anorexia, or bulimia.

* * * * *